US010440332B2

(12) United States Patent
Olsson et al.

(10) Patent No.: US 10,440,332 B2
(45) Date of Patent: Oct. 8, 2019

(54) INSPECTION CAMERA DEVICES AND METHODS WITH SELECTIVELY ILLUMINATED MULTISENSOR IMAGING

(71) Applicants: Mark S. Olsson, La Jolla, CA (US); Alexander L. Warren, San Diego, CA (US); Nicholas A. Smith, Chula Vista, CA (US); Michael J. Martin, San Diego, CA (US); Scott A. Powell, San Diego, CA (US)

(72) Inventors: Mark S. Olsson, La Jolla, CA (US); Alexander L. Warren, San Diego, CA (US); Nicholas A. Smith, Chula Vista, CA (US); Michael J. Martin, San Diego, CA (US); Scott A. Powell, San Diego, CA (US)

(73) Assignee: SEESCAN, INC., San Diego, CA (US)

( * ) Notice: Subject to any disclaimer, the term of this patent is extended or adjusted under 35 U.S.C. 154(b) by 152 days.

(21) Appl. No.: 14/935,878

(22) Filed: Nov. 9, 2015

(65) Prior Publication Data
US 2016/0261829 A1 Sep. 8, 2016

Related U.S. Application Data

(60) Provisional application No. 62/077,152, filed on Nov. 7, 2014.

(51) Int. Cl.
*H04N 7/18* (2006.01)
*H04N 5/265* (2006.01)
(Continued)

(52) U.S. Cl.
CPC ............. *H04N 7/183* (2013.01); *G03B 15/03* (2013.01); *G03B 17/08* (2013.01); *G03B 17/561* (2013.01);
(Continued)

(58) Field of Classification Search
CPC .... H04N 7/183; H04N 5/2256; H04N 5/2251; H04N 5/265; G03B 37/005; G03B 37/04; G03B 17/55
(Continued)

(56) References Cited

U.S. PATENT DOCUMENTS 5,682,199 A * 10/1997 Lankford ........... A61B 1/00105
348/65
6,483,535 B1 * 11/2002 Tamburrino ....... A61B 1/00163
348/345
(Continued)

FOREIGN PATENT DOCUMENTS

WO 2014/100903 7/2014

OTHER PUBLICATIONS

International Searching Authority, "International Search Report" for PCT Patent Application No. PCT/US15/059730, dated Dec. 5, 2016, European Patent Office, Munich.
(Continued)

*Primary Examiner* — Zaihan Jiang
(74) *Attorney, Agent, or Firm* — Steven C. Tietsworth, Esq.; Heena Sharma

(57) ABSTRACT

Camera head apparatus, systems, and methods for providing wide angle/panoramic images and/or video of the interior of pipes or other cavities using multiple imaging and illumination modules are disclosed.

29 Claims, 47 Drawing Sheets

(51) Int. Cl.
*H04N 5/232* (2006.01)
*H04N 5/225* (2006.01)
*G03B 37/00* (2006.01)
*G03B 15/03* (2006.01)
*G03B 17/08* (2006.01)
*G03B 17/56* (2006.01)
*G03B 37/04* (2006.01)
*G01N 21/954* (2006.01)
*G03B 17/55* (2006.01)

(52) U.S. Cl.
CPC .......... *G03B 37/005* (2013.01); *G03B 37/04* (2013.01); *H04N 5/2251* (2013.01); *H04N 5/2252* (2013.01); *H04N 5/2256* (2013.01); *H04N 5/2258* (2013.01); *H04N 5/23238* (2013.01); *H04N 5/23293* (2013.01); *H04N 5/265* (2013.01); *G01N 21/954* (2013.01); *G03B 17/55* (2013.01); *G03B 2215/0542* (2013.01); *G03B 2215/0567* (2013.01); *G03B 2215/0571* (2013.01); *H04N 2005/2255* (2013.01)

(58) Field of Classification Search
USPC .......................................... 348/84, E07.085
See application file for complete search history.

(56) References Cited

U.S. PATENT DOCUMENTS

| | | | |
|---|---|---|---|
| 6,831,679 B1* | 12/2004 | Olsson | G01N 21/954 348/241 |
| 2007/0182842 A1* | 8/2007 | Sonnenschein | A61B 1/00124 348/340 |
| 2012/0069172 A1* | 3/2012 | Hudritsch | G01N 21/954 348/84 |
| 2013/0019684 A1* | 1/2013 | Krywyj | F16L 55/28 73/592 |
| 2014/0320631 A1 | 10/2014 | Olsson et al. | |
| 2015/0013791 A1* | 1/2015 | Banowetz | H02K 15/00 137/559 |
| 2015/0364107 A1* | 12/2015 | Sakariya | G06F 3/0412 345/174 |
| 2015/0374210 A1* | 12/2015 | Durr | A61B 1/041 600/111 |
| 2016/0255305 A1* | 9/2016 | Ritchey | H04N 5/2254 348/14.03 |

OTHER PUBLICATIONS

International Searching Authority, "Written Opinion of the International Searching Authority" for PCT Patent Application No. PCT/US15/059730, dated Dec. 5, 2016, European Patent Office, Munich.

* cited by examiner

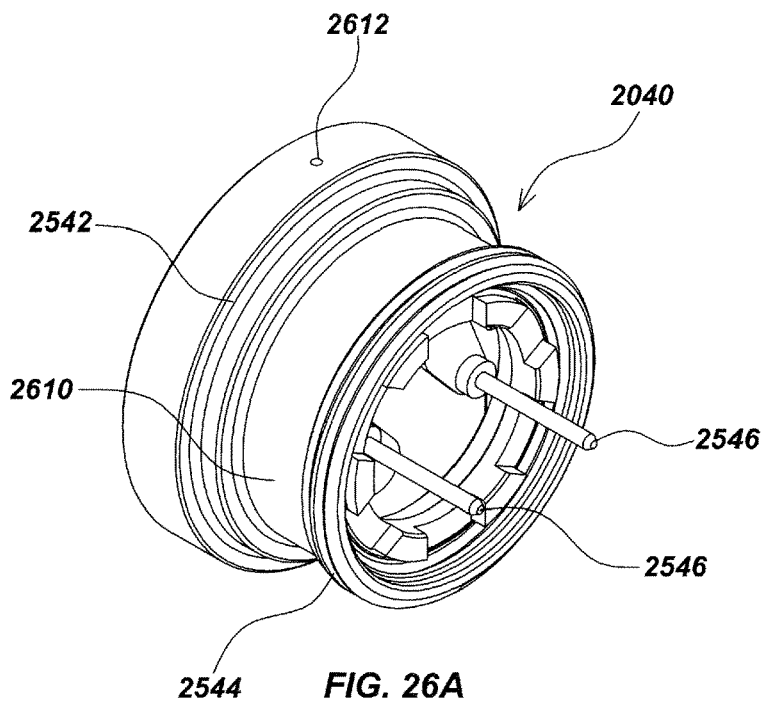
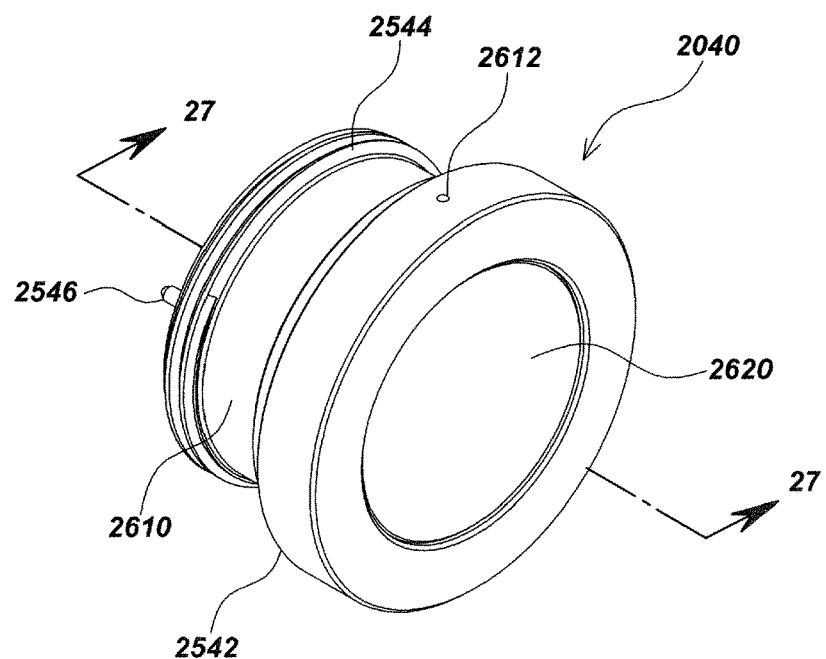
FIG. 26B

INSPECTION CAMERA DEVICES AND METHODS WITH SELECTIVELY ILLUMINATED MULTISENSOR IMAGING

CROSS-REFERENCE TO RELATED APPLICATIONS

This applications claims priority under 35 U.S.C. § 119(e) to U.S. Provisional Patent Application Ser. No. 62/077,152, entitled INSPECTION CAMERA DEVICES AND METHODS WITH SELECTIVELY ILLUMINATED MULTISENSOR IMAGING, filed Nov. 7, 2014, the content of which is incorporated by reference herein in its entirety for all purposes.

FIELD

This disclosure relates generally to apparatus, systems and methods for performing visual inspections within pipes and other conduits or voids. More specifically, but not exclusively, this disclosure relates to camera head apparatus, systems, and methods for providing wide angle/panoramic images and/or video of the interior of pipes or other cavities using multiple imaging and illumination modules.

BACKGROUND

Inspection cameras for use within pipes or other difficult to access voids are an essential tool in maintaining and repairing infrastructure. Such inspection cameras may be used to identify defects caused by, for example, ingress of roots; pipe cracks or breaks; corrosion; leakage; and/or other defects or blockages. Existing inspection cameras often use one or more light sources to illuminate the inside of the void being inspected to produce images and/or video of the inspected area. Inadequately illuminated inspection areas may make images and/or video dark and unusable at the quality and resolution needed to accurately and consistently identify problems in areas under inspected. Many existing inspection cameras fail to light the inspection area enough to produce images or video of sufficiently high quality or resolution. Other inspection cameras use high powered illumination devices that generate substantial heat. This heating can lead to overheating and failure of the camera or system in which the illumination device is used. Consequently, existing cameras and illumination devices often fail to adequately address overheating issues and/or fail to provide a desirable degree of illumination or sufficient resolution of generated images or video.

Accordingly, there is a need in the art to address the above-described as well as other problems.

SUMMARY

This disclosure relates generally to apparatus, systems and methods for performing visual inspections within pipes and other conduits or voids. More specifically, but not exclusively, this disclosure relates to camera head apparatus, systems, and methods for providing wide angle/panoramic images and/or video of the interior of pipes or other cavities using multiple imaging and illumination modules.

In one aspect, a camera head may include one or more imaging modules and one or more illumination modules disposed about or within a rounded or dome-shaped front element. Each imaging module may include one or more imaging elements/sensors for capturing images and/or video of a work area, such as the interior of a pipe or other conduit/void, and generating corresponding image or video output signals. In embodiments with two or more imaging modules, central optical axes of the imaging modules may be oriented such that they align to a common point or centroid within the camera head. Each illumination module may include one or more illumination elements, such as light emitting diodes (LEDs) or lasers, for illuminating a field of view imaged by the imaging modules. The camera head may further include one or more processing elements. Data corresponding to the images or video generated by the imaging modules may be provided to the processing element, where images or video from separate imaging modules may be combined or stitched together by the processing element to generate composite wide-angle images covering a wider field of view than that covered by individual imaging modules. The composite wide-angle images may be combined to form a wide-angle video file or stream or may be transmitted or stored individually for later signal processing or viewing. A generated video file or stream may be provided as an output from the processing element to a display element for rendering, and/or may be stored in a memory for later transmission, archiving, additional analysis, future viewing/playback and the like.

In another aspect, a pipe inspection system in accordance with aspects of the present disclosure may include a camera head having multiple imaging modules and/or multiple illumination modules, and the camera head may be coupled to a push-cable, allowing for insertion into and retrieval from a pipe and/or other conduit or void, either manually or via mechanically powered deployment/retrieval. A cable reel or other apparatus may be used for storing and dispensing the push-cable. A display element, such as an LCD or other display device, may be coupled to a proximal end of the push-cable. The camera head may be coupled to the other end of the push cable (distal end). The push-cable may include electrical and/or optical cabling to provide transmission of electrical power to the camera head as well as communication of data and/or images between the camera head and display element and/or other system devices, such as camera control units (CCUs). A processing element may be incorporated in the camera head and/or CCU to process images or video from the imaging module or modules, such as to generate high dynamic range (HDR) images, HDR video, stitched or tiled wide-angle images or video and the like. The display element may be incorporated in a CCU or other device, such as a notebook computer, tablet, smart phone, mobile base station, utility locator or other electronic computing device or system. The display element may display images, video and/or data provided from the camera head and/or other system devices and sensors. The display element may include or be a component of a dedicated camera control unit (CCU), notebook computer, tablet, smart phone and/or other computing device wirelessly and/or directly coupled via cabling to the cable reel, push-cable and/or camera head. Inspection systems may further include utility locating devices, mobile base stations, pipe sondes, notebook or other computer devices, tablets, smart phones and/or other devices or systems configured to operate with a camera head and/or other inspection system devices.

In another aspect, the illumination modules may include a light output or transmission window. The light output window may include a cavity on an inner side into which a light emitting diode or other illumination element or light source, such as a laser or other light output device, fits in close proximity with a surface of the light output window, such as in direct contact with all or a portion of the cavity of the light output window. The LED or other illumination element may be pressed against the surface of the window over a portion of the surface area within the cavity so as to minimize loss of light due to Fresnel reflections off the window, improve heat removal by conducting heat through the window, and/or allow the LED or other illumination element to seat further towards the outer environment of the camera head to maximize distribution of light into the work area.

In another aspect, an illumination module and/or camera head including one or more illumination modules may be configured efficiently draw heat away from the LEDs or other illumination elements as well as other components. Each illumination module may include a printed circuit board containing a thick flood of copper or other thermally conductive materials coupled to the LED or other illumination element, allowing heat to channel into the flood and away from the LED or other illumination element. The thermally conductive PCB flood may be positioned in thermal contact with the illumination module housing to distribute heat through other less heat sensitive components and/or to the exterior of the illumination module and/or camera head, and heat may then further dissipate to the external environment.

In another aspect, a method of manufacture for securing windows in a camera head or other device is described. The manufacturing method may be used to secure windows in both imaging modules and illumination modules. In the manufacturing method, a window may be secured in place within a housing by injecting epoxy or other adhesives into one or more aligned annular grooves formed on the window, a corresponding housing element, or both. The epoxy or other adhesive may form a barrier or seal so as to protect components within the illumination module, imaging module and/or elsewhere in the camera head or other device from exposure to harmful or corrosive external elements such a liquids, gases, dust and the like.

In another aspect, light output produced by the illumination modules of a camera head or other device may be controlled by being varied in conjunction with imaging operations performed by the imaging modules so as to enhance imaging module performance and corresponding image or video output signals. Light output may be increased at defined time intervals, allowing the imaging elements to produce enhanced resolution images during each of these intervals of increased light output, while reducing heat and/or energy consumption during other time intervals where light output is decreased or turned off. Between high light output intervals, the illumination elements (e.g., LEDs, lasers and the like) may be driven at a lowered power level (and corresponding lower output illumination level) to allow heat to dissipate from the camera head, illumination module or other device, thereby reducing overheating of internal components of the camera head or other device and/or reducing power consumption.

In another aspect, controlled varying of light output levels may be used to implement high dynamic range exposures of the inspection area by capturing multiple images at different output light levels and combining the images in a processing element to generate high dynamic range output images and/or video streams or files.

In another aspect, the imaging modules of a camera head or other device may be positioned with overlapping fields of view. In such embodiments, digital tiling and/or image stitching may be used to create one or more composite wide-angle images or video streams of an area being inspected (e.g., a pipe interior, underground cavity, machine interior, or other area or device being inspection). A camera head and/or CCU or other display element may further be configured to provide digitally simulated articulation within captured images and/or video.

In another aspect, the field of view of the optical element of each imaging module may project upon an active area on a corresponding imaging sensor such that the entire image circle captured by the imaging module's optical field of view fits onto the active area of the imaging sensor. (i.e., a circular optically imaged area is placed entirely within the rectangular or square imaging area of a rectangular or square imaging sensor).

In another aspect, a camera head may include inertial navigation sensors (INS) and/or other position or orientation sensors and/or may be configured to interpret motion utilizing motion tracking analysis to determine camera head movement/location.

In another aspect, an inspection system may include a utility locator device for capturing images or video of a ground surface corresponding to pipe inspection images or videos taken within the pipe or other cavity at a corresponding location (e.g., at a corresponding location of the pipe or cavity under the ground). Corresponding imagery may be used to generate combined inspection and locate mapping data, which may be displayed, stored in a memory, transmitted to another electronic computing device or system, or otherwise used, archived or analyzed.

In another aspect, mapping data or information generated by the various methods and devices disclosed herein, as well as other pipe or cavity inspection and locate data, may be associated, combined, transmitted and/or stored in a database or archive, which may be a cloud database or other database.

In another aspect, a utility locator device may display a map or maps with corresponding pipe inspection imagery and/or data. Various control actions, such as walking along the ground surface above inspection imagery location, reviewing a location electronically on a display element of the locator or other electronic computing device or system and the like may be used to view, scroll, send and/or otherwise review or analyze the pipe inspection image or video data.

In another aspect, a stand-alone illumination device may include one or more illumination modules.

In another aspect, a panoramic photosphere camera device may include a plurality of imaging modules. The photosphere camera device may further include one or more illumination modules.

In another aspect, a non-transitory processor readable media may include instructions for implementing methods and functions described herein, in whole or in part, on one or more processing elements in a camera head or other device or system.

Various additional aspects, features, devices, systems, and functionality are further described below in conjunction with the appended Drawings.

BRIEF DESCRIPTION OF THE DRAWINGS

The present application may be more fully appreciated in connection with the following detailed description taken in conjunction with the accompanying drawings, wherein:

FIG. 26A is a back to front isometric view of the illumination module embodiment of FIG. 25.

FIG. 26B is a front to back isometric view of the illumination module embodiment of FIG. 25.

DETAILED DESCRIPTION OF EMBODIMENTS

Overview

Figure 1:
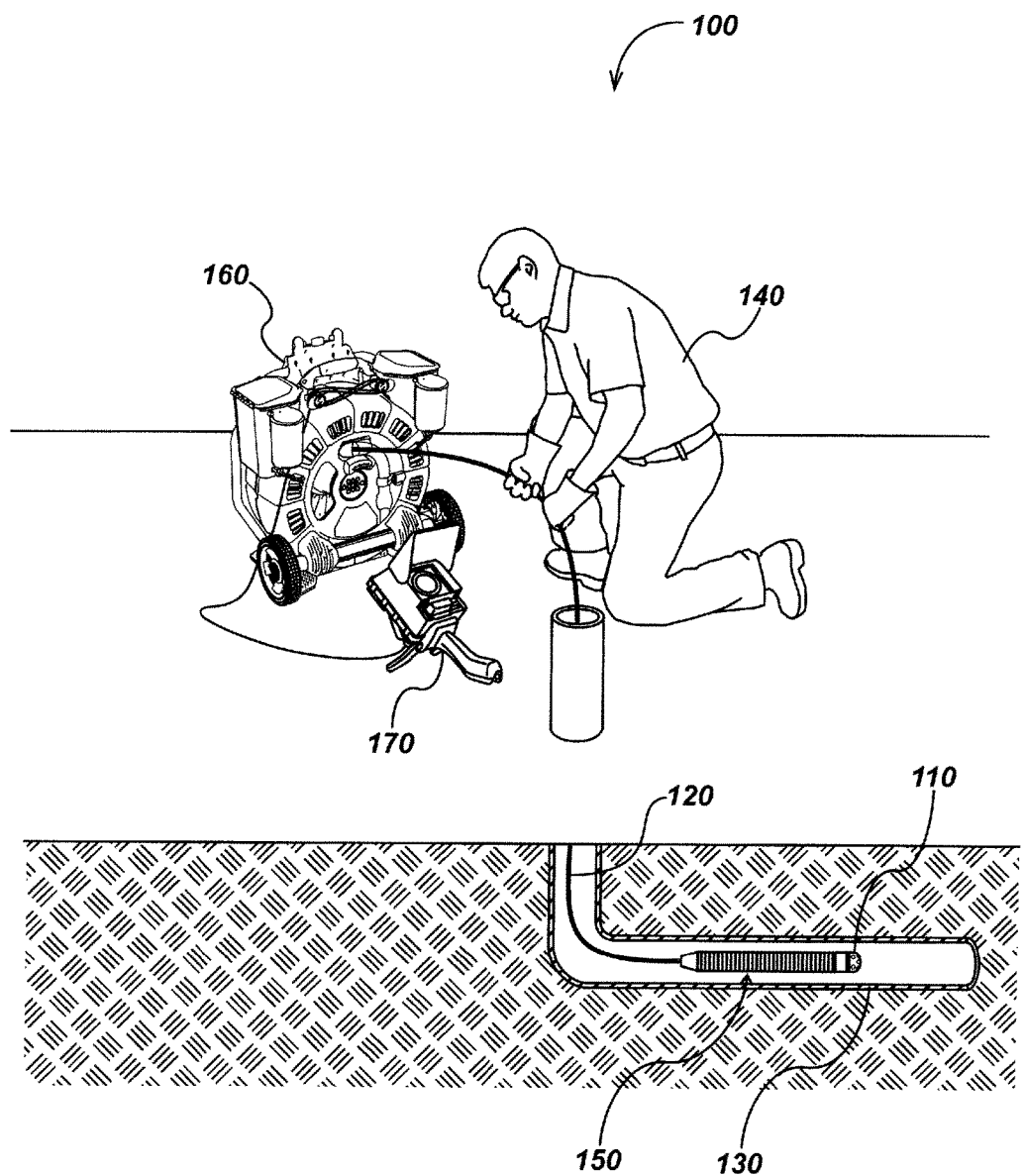
FIG. 1 is an illustration of a pipe inspection system embodiment in accordance with certain aspects.

Various aspects of pipe inspection systems, apparatus, devices, configurations and methods that may be used in conjunction with the details herein various embodiments are described in co-assigned patents and patent applications including: U.S. Pat. No. 5,939,679, filed Feb. 9, 1998, entitled Video Push Cable; U.S. Pat. No. 6,545,704, filed Jul. 7, 1999, entitled Video Pipe Inspection Distance Measuring System; U.S. Pat. No. 6,958,767, filed Jan. 31, 2002, entitled Video Pipe Inspection System Employing Non-Rotating Cable Storage Drum; U.S. Pat. No. 6,862,945, filed Oct. 22, 2002, entitled Camera Guide for Video Pipe Inspection System; U.S. Pat. No. 6,958,767, issued Oct. 25, 2005, entitled Video Pipe Inspection System Employing Non-Rotating Cable Storage Drum; U.S. Pat. No. 7,009,399, issued Mar. 7, 2006, entitled Omnidirectional Sonde and Line Locator; U.S. Pat. No. 7,221,136, issued May 22, 2007, entitled Sondes for Locating Underground Pipes and Conduits; U.S. Pat. No. 7,276,910, issued Oct. 2, 2007, entitled A Compact Self-Tuned Electrical Resonator for Buried Object Locator Applications; U.S. Pat. No. 7,288,929, issued Oct. 30, 2007, entitled Inductive Clamp for Applying Clamp for Applying Signal to Buried Utilities; U.S. Pat. No. 7,298,126, issued Nov. 20, 2007, entitled Sondes for Locating Underground Pipes and Conduits; U.S. Pat. No. 7,443,154, issued Oct. 28, 2008, entitled Multi-Sensor Mapping Omnidirectional Sonde and Line Locator; U.S. Pat. No. 7,518,374, issued Apr. 14, 2009, entitled Reconfigurable Portable Locator Employing Multiple Sensor Array Having Flexible Nested Orthogonal Antennas; U.S. Pat. No. 7,619,516, issued Nov. 17, 2009, entitled Single and Multi-Trace Omnidirectional Sonde and Line Locators and Transmitters Used Therewith; U.S. patent application Ser. No. 12/704,808, filed Feb. 12, 2010, entitled Pipe Inspection System with Replaceable Cable Storage Drum; U.S. patent application Ser. No. 12/766,742, filed Apr. 23, 2010, entitled Pipe Inspection Cable Counter and Overlay Management System; U.S. Pat. No. 7,825,647, issued Nov. 2, 2010, entitled Compact Line Illuminator for Locating Buried Pipes and Cables; U.S. Pat. No. 7,863,885, issued Jan. 4, 2011, entitled Sondes for Locating Underground Pipes and Conduits; U.S. patent application Ser. No. 13/073,919, filed Mar. 28, 2011, entitled Pipe Inspection System with Jetter Push-Cable; U.S. Pat. No. 7,990,151, issued Aug. 2, 2011, entitled Tri-Pod Buried Locator System; U.S. patent application Ser. No. 13/346,668, filed Jan. 9, 2012, entitled Portable Camera Controller Platform for Use with Pipe Inspection System; U.S. patent application Ser. No. 13/358,463, filed Jan. 25, 2012, entitled Self-Leveling Inspection Systems and Methods; U.S. patent application Ser. No. 13/469,024, filed May 10, 2012, entitled Buried Object Locator Apparatus and Systems; U.S. patent application Ser. No. 13/570,211, filed Aug. 8, 2012, entitled Phase-Synchronized Buried Object Locator Apparatus, System, and Methods; U.S. Pat. No. 8,248,056, issued Aug. 21, 2012, entitled A Buried Object Locator System Employing Automated Virtual Depth Event Detection and Signaling; U.S. Pat. No. 8,289,385, issued Oct. 16, 2012, entitled Push-Cable for Pipe Inspection System; U.S. Pat. No. 8,264,226, issued Sep. 11, 2012, entitled System and Method for Locating Buried Pipes and Cables with a Man Portable Locator and a Transmitter in a Mesh Network; U.S. Pat. No. 8,395,661, filed Mar. 12, 2013, entitled Pipe Inspection System with Selective Image Capture; U.S. patent application Ser. No. 13/676,989, filed Nov. 11, 2012, entitled Quad-Gradient Coils For Use in Locating System; U.S. patent application Ser. No. 13/676,018, filed Nov. 13, 2012, entitled Portable Pipe Inspection Systems and Apparatus; U.S. patent application Ser. No. 13/754,767, filed Jan. 30, 2013, entitled Adjustable Variable Resolution Inspection Systems and Methods; U.S. patent application Ser. No. 13/775,066, filed Feb. 22, 2013, entitled Thermal Extraction Architecture for Camera Heads, Inspection Systems, and Other Devices and Systems; U.S. patent application Ser. No. 13/774,351, filed Feb. 22, 2013, entitled Dockable Tripodal Camera Control Unit; U.S. patent application Ser. No. 13/851,951, U.S. patent application Ser. No. 13/826,112, filed Mar. 14, 2013, entitled Systems and Methods Involving a Smart Cable Storage Drum Network Node for Transmission of Data; filed Mar. 27, 2013, entitled Dual Antenna Systems with Variable Polarization; U.S. patent application Ser. No. 13/874,879, filed May 1, 2013, entitled High Bandwidth Push-Cables for Video Pipe Inspection Systems; U.S. patent application Ser. No. 13/913,485, filed Jun. 9, 2013, entitled Multi-Camera Pipe Inspection Apparatus, Systems and Methods; U.S. Pat. No. 8,547,428, issued Oct. 1, 2013, entitled Pipe Mapping System; U.S. Provisional Patent Application No. 61/920,457, filed Dec. 23, 2013, entitled Nulled-Signal Locating Devices, Systems, and Methods; U.S. Pat. No. 8,587,648, issued Nov. 19, 2013, entitled Self-Leveling Camera Head; U.S. patent application Ser. No. 14/207,089, filed Mar. 12, 2014, entitled Multi-Camera Pipe Inspection Apparatus, Systems and Methods; U.S. patent application Ser. No. 14/215,290, filed Mar. 17, 2014, entitled Sonde Devices Including a Sectional Ferrite; U.S. patent application Ser. No. 14/216,358, filed Mar. 17, 2014, entitled Smart Cable Storage Drum and Network Node System and Methods; U.S. Provisional Patent Application No. 62/019,715, filed Jul. 1, 2014, entitled Stereo Optical Ground Tracking Apparatus Systems, and Methods; U.S. patent application Ser. No. 14/332,268, filed Jul. 15, 2014, entitled Utility Locator Transmitter Devices, Systems, and Methods with Dockable Apparatus; U.S. Provisional Patent Application No. 62/026,010, filed Jul. 17, 2014, entitled Methods and Systems for Generating Interactive Mapping Displays in Conjunction with User Interface Devices; U.S. patent application Ser. No. 14/446,279, filed Jul. 29, 2014, entitled Inductive Clamp Devices, Systems, and Methods; U.S. patent application Ser. No. 14/446,145, filed Jul. 29, 2014, entitled Utility Locating Systems with Mobile Base Station; U.S. patent application Ser. No. 14/469,536, filed Aug. 26, 2014, entitled Cable Storage Drum with Moveable CCU Docking Apparatus; and U.S. patent application Ser. No. 14/516,558, filed Oct. 16, 2014, entitled Electronic Marker Devices and Systems. The content of each of these patents and applications is incorporated by reference herein in its entirety.

This disclosure relates generally to apparatus, systems and methods for performing visual inspections within pipes and other conduits or voids. For example, in one aspect, the disclosure relates to camera head apparatus, systems and methods for providing wide angle images and/or video of the interior of pipes or other cavities or voids using one or more imaging modules, along with enhanced illumination modules, to provide enhanced image or video quality and/or resolution.

In another aspect, the disclosure relates to a camera head including one or more imaging modules and one or more illumination modules disposed about or within a rounded or dome-shaped front element. Each imaging module may include one or more imaging elements/sensors for capturing images and/or video of a work area, such as the interior of a pipe or other conduit/void, and generating corresponding image or video output signals. In embodiments with two or more imaging modules, central optical axes of the imaging modules may be oriented such that they align to a common point or centroid within the camera head. Each illumination module may include one or more illumination elements, such as light emitting diodes (LEDs) or lasers, for illuminating a field of view imaged by the imaging modules. The camera head may further include one or more processing elements. Data corresponding to the images or video generated by the imaging modules may be provided to the processing element, where images or video from separate imaging modules may be combined or stitched together by the processing element to generate composite wide-angle images covering a wider field of view than that covered by individual imaging modules. The composite wide-angle images may be combined to form a wide-angle video file or stream or may be transmitted or stored individually for later signal processing or viewing. A generated video file or stream may be provided as an output from the processing element to a display element for rendering, and/or may be stored in a memory for later transmission, archiving, additional analysis, future viewing/playback and the like. In some embodiments, images or videos generated by a camera head may be transmitted to an associated buried utility locator for use in conjunction with utility locator data, images or video, and/or other information. Camera head and utility locator data may be associated or combined, stored in a memory, displayed in a display device, and/or transmitted to other electronic computing devices or systems.

In another aspect, a camera head in accordance with aspects of the disclosure may include inertial navigation sensors (INS) and/or other position sensors and/or include one or more processing elements to interpret motion by implementing motion tracking algorithms to determine camera head position and/or movement. This information may be combined with GPS or other location system data or information to associated motion or position with absolute reference coordinates. In some embodiments, cable counting devices for measuring the amount of push-cable dispensed may be used to determine distance of movement of a camera head or amount of push-cable deployed into the inspection area. Tracking of position and movement of the camera head may further be used to reference the pipe and/or conduit location relative to a starting point or reference location. In some embodiments, a camera head, camera control unit, reel, and/or other satellite navigation sensors and systems such a global positioning system (GPS) sensors, GLONASS, or other sensors or system may be included to determine the starting point location relative to a reference position (e.g., Earth latitude/longitude coordinates). In some embodiments, a user may indicate the starting point location within a mapping system on a locator, CCU, or other device or system. Successive movements/positions of a camera head, tracked using one or more INS and/or motion tracking, may be used to map a pipe inspection with respect to a local position and/or relative to its location within and above or below the Earth's surface.

In another aspect, a pipe inspection system may include a camera head having multiple imaging modules and/or multiple illumination modules, and the camera head may be coupled to a push-cable, allowing for insertion into and retrieval from a pipe and/or other conduit or void, either manually or via mechanically powered deployment/retrieval. A cable reel or other apparatus may be used for storing and dispensing the push-cable. A display element, such as an LCD or other display device, may be coupled to a proximal end of the push-cable. The camera head may be coupled to the other end of the push cable (distal end). The push-cable may include electrical and/or optical cabling to provide transmission of electrical power to the camera head as well as communication of data and/or images between the camera head and display element and/or other system devices, such as camera control units (CCUs). A processing element may be incorporated in the camera head and/or CCU to process images or video from the imaging module or modules, such as to generate high dynamic range (HDR) images, HDR video, stitched or tiled wide-angle images or video and the like. The display element may be incorporated in a CCU or other device, such as a notebook computer, tablet, smart phone, mobile base station, utility locator or other electronic computing device or system. The display element may display images, video and/or data provided from the camera head and/or other system devices and sensors. The display element may include or be a component of a dedicated camera control unit (CCU), notebook computer, tablet, smart phone and/or other computing device wirelessly and/or directly coupled via cabling to the cable reel, push-cable and/or camera head. Inspection systems may further include utility locating devices, mobile base stations, pipe sondes, notebook or other computer devices, tablets, smart phones and/or other devices or systems configured to operate with a camera head and/or other inspection system devices.

In another aspect, the illumination modules may include a light output or transmission window. The light output window may include a cavity on an inner side into which a light emitting diode or other illumination element or light source, such as a laser or other light output device, fits in close proximity with a surface of the light output window, such as in direct contact with all or a portion of the cavity of the light output window. The LED or other illumination element may be pressed against the surface of the window over a portion of the surface area within the cavity so as to minimize loss of light due to Fresnel reflections off the window, improve heat removal by conducting heat through the window, and/or allow the LED or other illumination element to seat further towards the outer environment of the camera head to maximize distribution of light into the work area.

In another aspect, an illumination module and/or camera head including one or more illumination modules may be configured to efficiently draw heat away from the LEDs or other illumination elements, as well as other components. Each illumination module may include a printed circuit board containing a thick flood of copper or other thermally conductive materials coupled to the LED or other illumination element, allowing heat to channel into the flood and away from the LED or other illumination element. The thermally conductive PCB flood may be positioned in thermal contact with the illumination module housing to distribute heat through other less heat sensitive components and/or to the exterior of the illumination module and/or camera head, and heat may then further dissipate to the external environment.

In another aspect, a method of manufacture for securing windows in a camera head or other device is described. The manufacturing method may be used to secure windows in both imaging modules and illumination modules. In the manufacturing method, a window may be secured in place in a housing by injecting epoxy or other adhesives into one or more aligned annular grooves formed on the window, a corresponding housing element, or both. The epoxy or other adhesive may form a barrier or seal so as to protect components within the illumination module, imaging module and/or elsewhere in the camera head or other device from exposure to harmful or corrosive external elements such a liquids, gases, dust and the like.

In another aspect, light output produced by the illumination modules of a camera head or other device may be controlled by being varied in conjunction with imaging operations performed by the imaging modules so as to enhance imaging module performance and corresponding image or video output signals. Light output may be increased at defined time intervals, allowing the imaging elements to produce enhanced resolution images during each of these intervals of increased light output, while reducing heat and/or energy consumption during other time intervals where light output is decreased or turned off. Between high light output intervals, the illumination elements (e.g., LEDs, lasers and the like) may be driven at a lowered power level (and corresponding lower output illumination level) to allow heat to dissipate from the camera head, illumination module or other device, thereby reducing overheating of internal components of the camera head or other device and/or reducing power consumption.

In another aspect, controlled varying of light output levels may be used to implement high dynamic range exposures of the inspection area by capturing multiple images at different output light levels and combining the images in a processing element to generate high dynamic range output images and/or video streams or files.

In another aspect, the imaging modules of a camera head or other device may be positioned so as to provide overlapping fields of view (FOVs). In such embodiments, digital tiling and/or image stitching may be used to create one or more composite wide-angle images or video streams of an area being inspected (e.g., a pipe interior, underground cavity, machine interior, or other area or device being inspection). A camera head and/or CCU or other display element may further provide digitally simulated articulation within captured images and/or video.

In another aspect, the field of view of the optical element of each imaging module may project upon an active area on a corresponding imaging sensor such that the entire image circle captured by the imaging module's optical field of view fits onto the active area of the imaging sensor. (i.e., a circular optically imaged area is placed entirely within the rectangular or square imaging area of a rectangular or square imaging sensor, rather than being cropped by the square or rectangular imaging area).

In another aspect, a camera head may include inertial navigation sensors (INS) and/or other position or orientation sensors and/or may be configured to interpret motion by implementing motion tracking algorithms to determine camera head movement/location.

In another aspect, an inspection system may include a utility locator device for capturing images or video of a ground surface corresponding to pipe inspection images or videos taken within the pipe or other cavity at a corresponding location (e.g., at a corresponding location of the pipe or cavity under the ground). Corresponding imagery may be used to generate combined inspection and locate mapping data, which may be displayed, stored in a memory, transmitted to another electronic computing device or system, or otherwise used, archived or analyzed.

In another aspect, mapping data or information generated by the various methods and devices disclosed herein, as well as other pipe or cavity inspection and locate data, may be associated, combined, transmitted and/or stored in a database or archive, which may be a cloud database or other database.

In another aspect, a utility locator device may display a map or maps with corresponding pipe inspection imagery and/or data. Various control actions, such as walking along the ground surface above inspection imagery location, reviewing a location electronically on a display element of the locator or other electronic computing device or system and the like may be used to view, scroll, send and/or otherwise review or analyze the pipe inspection image or video data.

Maps created utilizing methods and devices disclosed herein, as well as other pipe inspection and locate data, may be stored in a database which may be a cloud database. Such a database may be further accessible by various system devices both during an ongoing inspection as well as in future inspections. For instance, a display element on a camera control unit, utility locator device, computing device, and/or other system device configured with a display element may display historic imagery of a section of pipe or other inspection area as well as current imagery. Such historic imagery may be used, as an example, to display sections of pipe before and after a pipe relining project or other operation.

In some system embodiments, a utility locator device may display a map or maps with pipe inspection imagery and data. For example, a utility locator may display mapping data comprised of, in part, mapping imagery from within a pipe. As a user moves about the ground surface above the location of the inspected pipe, a utility locator may provide a display that scrolls through map imagery such that the map imagery from within the pipe displayed upon the utility locator device corresponds to the appropriate location at the ground surface. One or more pointing devices, buttons, or other controls on the display element device may, alternatively or in addition to the aforementioned map control method, be used to control movement and/or other operations within a pipe inspection map or other data or imagery.

In another aspect, a stand-alone illumination device may include one or more illumination modules. Some stand-alone illumination device embodiments may include a watertight housing for underwater use.

In another aspect, a panoramic photosphere camera device may include a plurality of imaging modules. The photosphere camera device may further include one or more illumination modules. Such a device may be capable of generating a 360 or near 360 degree panoramic photo sphere while simultaneously illuminating the surrounding area. Such a device may be coupled to a tablet, smart phone, other computing device, and/or other display element via a wired or wireless connection, such as a Bluetooth, WiFi, or other wireless connection.

In another aspect, the disclosure relates to non-transitory processor readable media including instructions for implementing methods and functions described herein, in whole or in part, on one or more processing elements in a camera head or other device or system.

Various additional aspects, features, devices, systems, and functionality are further described below in conjunction with the appended Drawings.

Example Illumination Modules and Camera Heads Embodiments

FIG. 1 illustrates an inspection system embodiment 100 in accordance with aspects of the present disclosure. Inspection system 100 may include a camera head 110 coupled to a push-cable 120, allowing the camera head 110 to be pushed into a pipe 130 and/or other conduit or void by a user 140 or via user-controlled or automated mechanical force (not shown in FIG. 1). The push-cable 120 may be a push-cable as described in, for example, the following co-assigned patents and patent applications: U.S. Pat. No. 5,457,288, issued Oct. 10, 1995, entitled Dual Push-Cable for Pipe Inspection; U.S. Pat. No. 5,808,239, issued Sep. 15, 1998, entitled Video Push-Cable; U.S. Pat. No. 5,939,679, issued Aug. 17, 1999, entitled Video Push-Cable; U.S. patent application Ser. No. 11/679,092, filed Feb. 26, 2007, entitled Light Weight Sewer Cable; U.S. patent application Ser. No. 13/589,948, filed Aug. 20, 2012, entitled Light Weight Sewer Cable; U.S. patent application Ser. No. 13/874,879, filed May 1, 2013, entitled High Bandwidth Push-Cables for Pipe Inspection Systems; and/or U.S. patent application Ser. No. 14/207,517, filed Mar. 12, 2014, entitled High Bandwidth Push-Cables for Pipe Inspection Systems. The content of each of these applications is incorporated by reference herein in its entirety. A push-cable spring 150 may further couple between the push-cable 120 and camera head 110. The spring may be used to further improve movement and/or handling of the camera head 110 into and within the pipe 130 or other void. The push-cable spring 150 may be of the variety described in, for example, co-assigned U.S. patent application Ser. No. 14/271,255, filed May 6, 2014, entitled Spring Assemblies with Variable Flexibility for use with Push-Cables and Pipe Inspection Systems, the content of which is incorporated by reference herein in its entirety.

A cable reel 160 or other apparatus for dispensing push-cable 120, and a display element, such as camera control unit (CCU) 170, may further be coupled to a proximal end of the push-cable 120. The camera head 110 may be coupled to a distal end of the push-cable. The cable reel 160 may be a reel/cable storage drum as described, for example, co-assigned patents and patent applications including: U.S. Pat. No. 6,958,767, issued Oct. 25, 2005, entitled Video Pipe Inspection System Employing Non-Rotating Cable Storage Drum; U.S. patent application Ser. No. 12/704,808, filed Feb. 12, 2010, entitled Pipe Inspection System with Replaceable Cable Storage Drum; U.S. patent application Ser. No. 13/826,112, filed Mar. 14, 2013, entitled Systems and Methods Involving a Smart Cable Storage Drum and Network Node for Transmission of Data; U.S. patent application Ser. No. 14/216,358, filed Mar. 17, 2014, entitled Systems and Methods Involving a Smart Cable Storage Drum and Network Node and Methods; and/or U.S. patent application Ser. No. 14/469,536, filed Aug. 26, 2014, entitled Cable Storage Drum with Moveable CCU Docking Apparatus. The content of each of these applications is incorporated by reference herein in its entirety.

The cable reel and or other system device may further include an element for measuring the amount of cable dispensed (e.g., a cable or distance counter), such as those described in, for example, co-assigned U.S. patent application Ser. No. 14/203,485, filed Mar. 10, 2014, entitled Pipe Inspection Cable Counter and Overlay Management System, and/or U.S. patent application Ser. No. 12/766,742, filed Apr. 23, 2010, entitled Pipe Inspection Cable Counter and Overlay Management System. The content of each of these applications is incorporated by reference herein in its entirety.

The CCU 170 and/or other display elements or systems may display images, video, and/or data provided from the camera head 110 (or other multi-imaging module device or system). The CCU 170 may further control operation of the camera head, displayed images/video, and/or other devices within the inspection system. The CCU 170 may, for example, be a device as described in co-assigned U.S. patent application Ser. No. 13/941,381, filed Jul. 12, 2013, entitled Self-Grounding Transmitting Portable Camera Controller for Use with Pipe Inspection Systems, and/or U.S. patent application Ser. No. 14/213,458, filed Mar. 14, 2014, entitled Self-Grounding Transmitting Portable Camera Controller for Use with Pipe Inspection Systems. The content of each of these applications is incorporated by reference herein in its entirety. In some embodiments, the display element may be a computing device or system such as a laptop computer, smart phone, tablet computer, a utility locator device and/or other devices or systems for displaying and/or controlling operation of the camera head 110, or controlling image or video display parameters such as perspective within received images/video, lighting controls, resolution controls, articulation controls and the like.

The push-cable 120 may include internal cabling for providing electrical power to camera head 110 as well as communication of data such as images, video, sensor data, and the like between the camera head 110 and camera control unit 170 and/or other system devices. In some embodiments communication of data may be done fully or partially via wireless communication rather than via internal metallic or optical cabling. In some embodiments, electrical power may be provided by one or more batteries (not illustrated) that may be coupled to the reel 160 and/or camera control unit 170. The batteries may, for example, be smart batteries such as those described in co-assigned U.S. patent application Ser. No. 13/925,636, filed Jun. 24, 2012, entitled Modular Battery Pack Apparatus, Systems, and Methods, and/or U.S. patent application Ser. No. 13/532, 721, filed Jun. 25, 2012, entitled Modular Battery Pack Apparatus, Systems, and Methods. The content of each of these applications is incorporated by reference herein in its entirety.

Figure 2A:
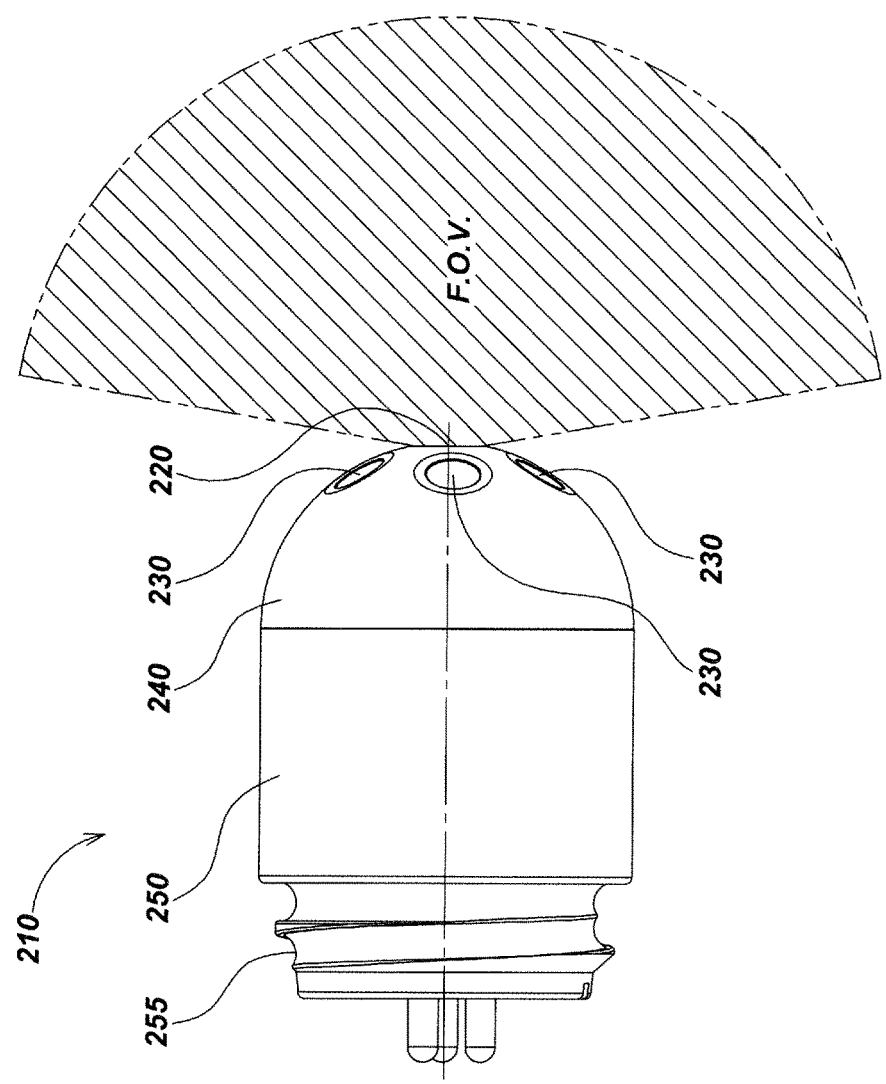
FIG. 2A is a side view of details of an embodiment of a camera head including multiple imaging modules an example field of view (FOV).
Figure 2B:
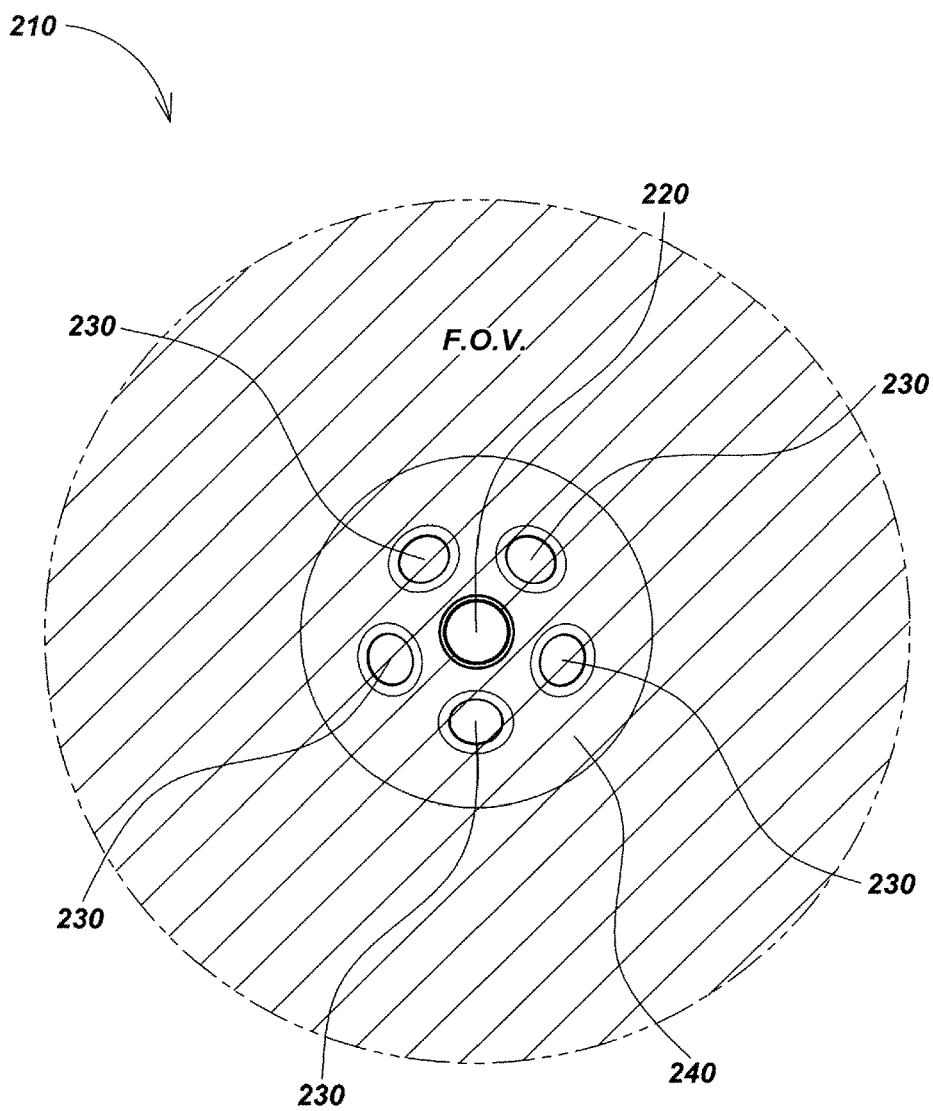
FIG. 2B is a front view of the camera head embodiment of FIG. 2A, illustrating the field of view from another angle.
Figure 2C:
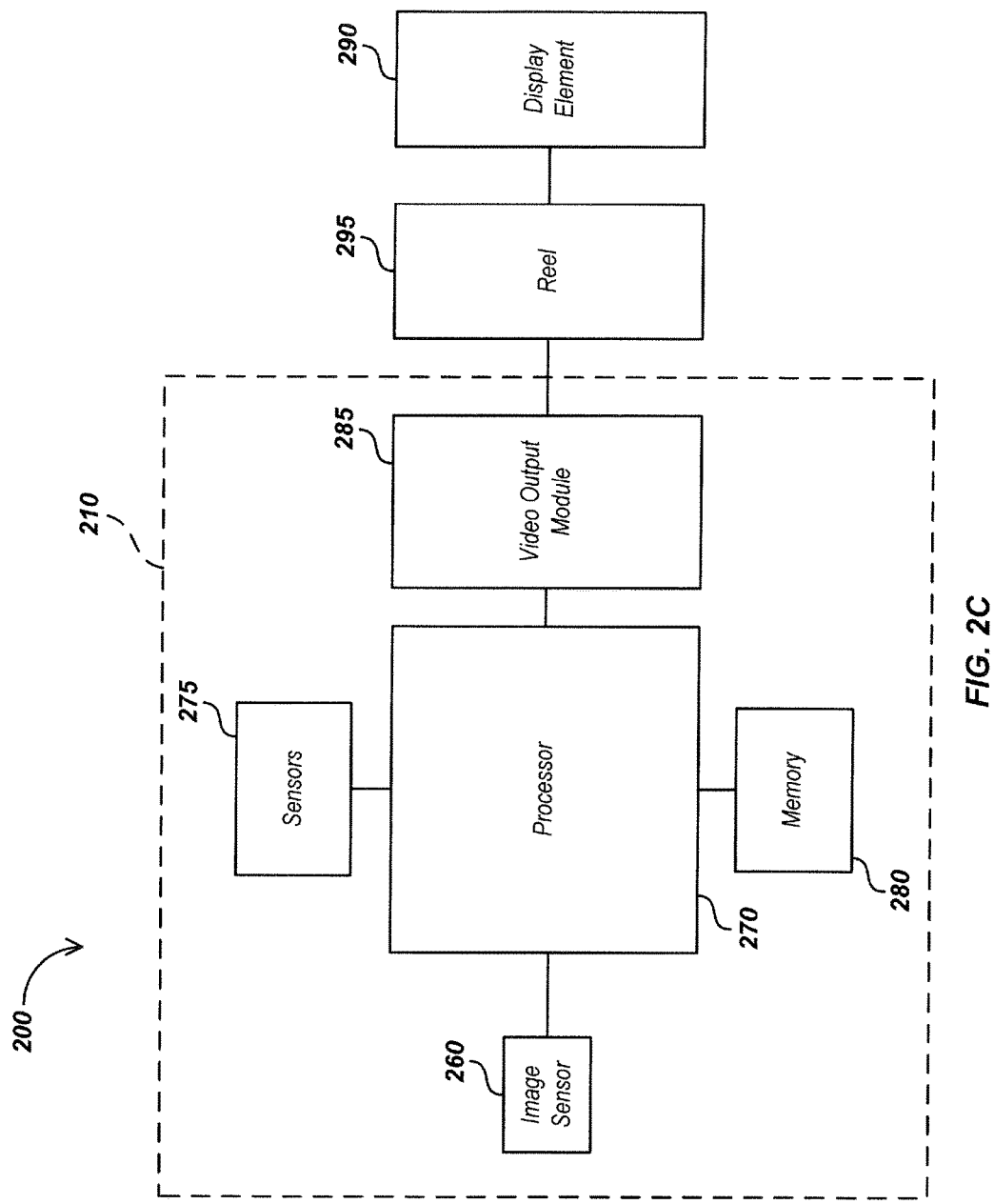
FIG. 2C is a block diagram illustrating details of an inspection system embodiment in accordance with certain aspects.
Figure 3A:
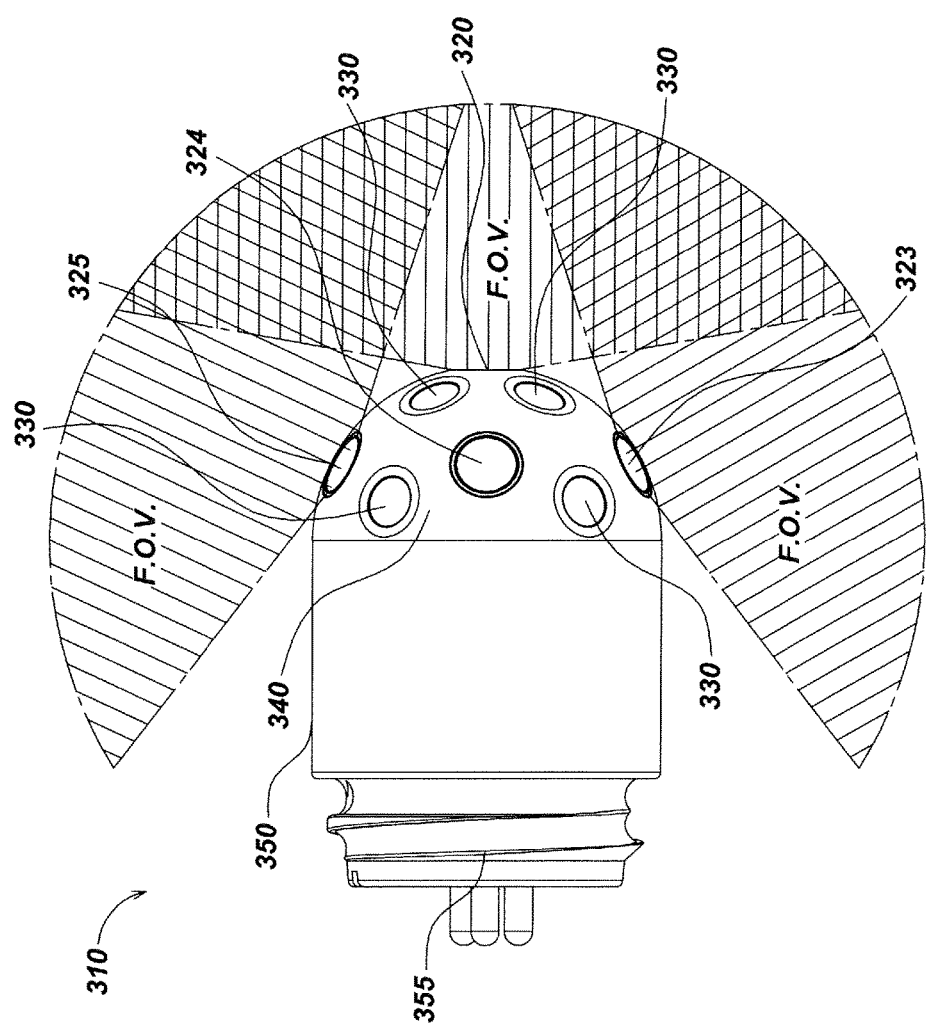
FIG. 3A is a side view of an exemplary camera head embodiment in accordance with certain aspects, illustrating its field of view.
Figure 3B:
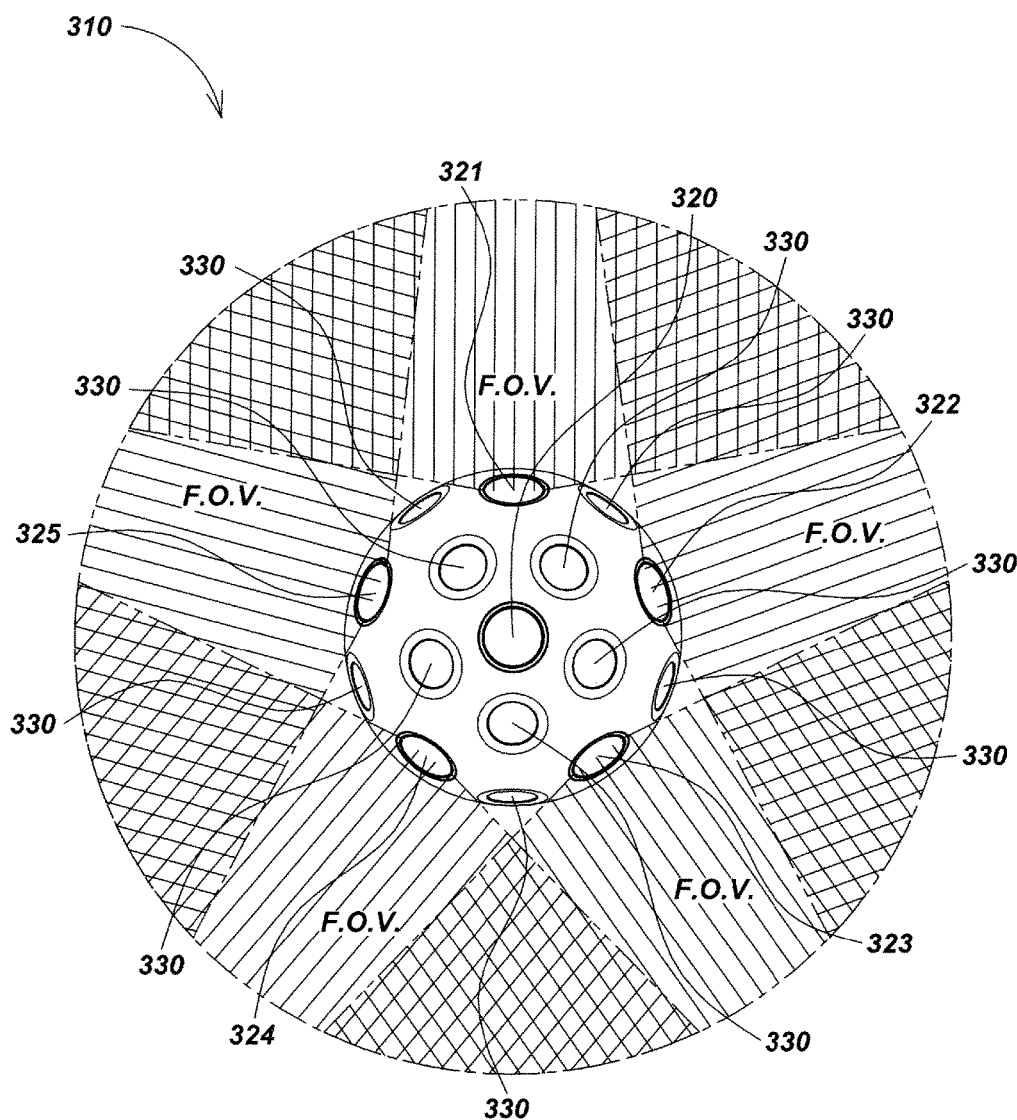
FIG. 3B is a front view of the camera head embodiment of FIG. 3A, illustrating its field of view from another angle.
Figure 3C:
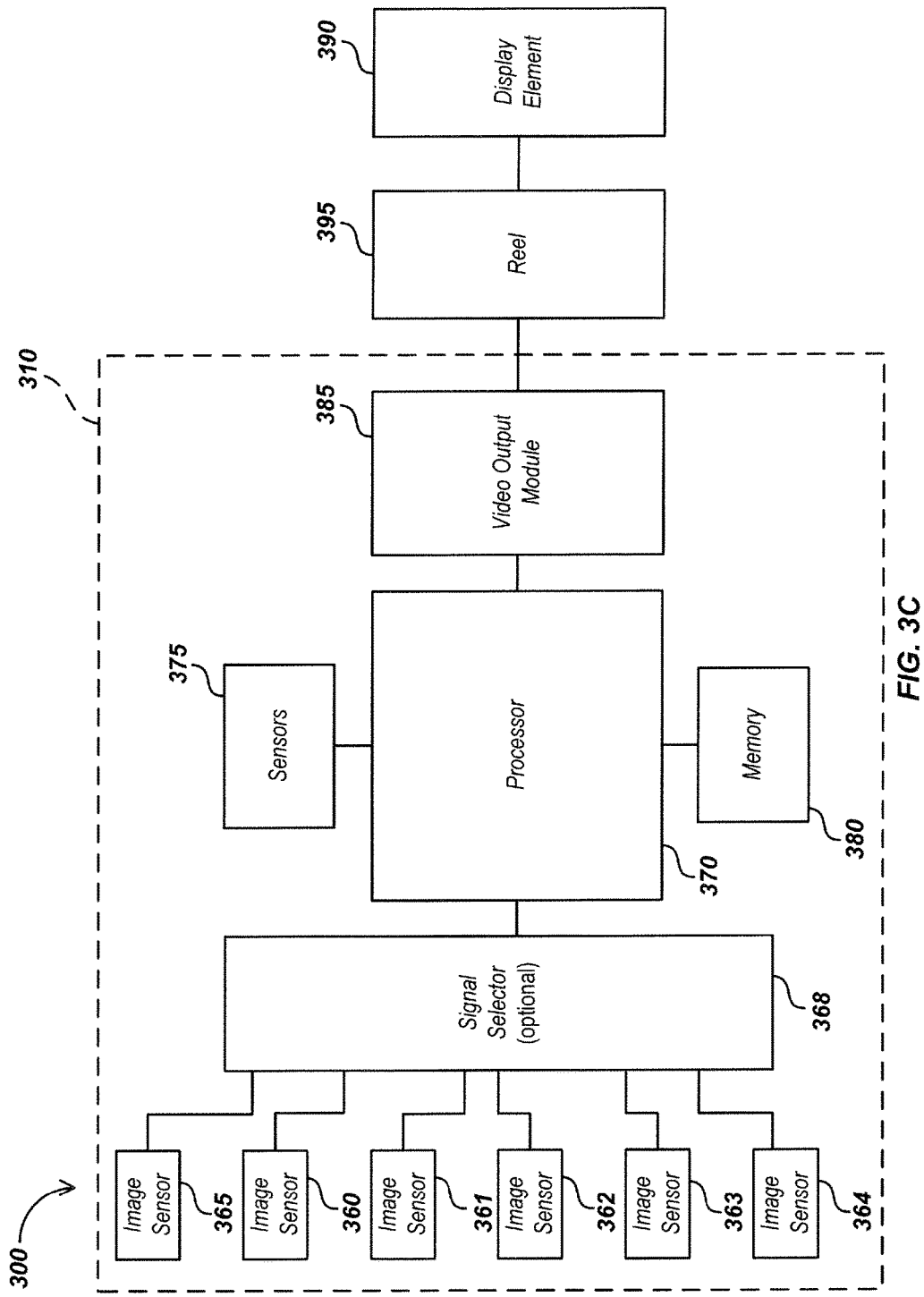
FIG. 3C is a block diagram illustrating details of an inspection system embodiment in accordance with certain aspects.

An inspection system embodiment in accordance with aspects of the present disclosure, such as inspection system 100 of FIG. 1, inspection system 200 of FIG. 2C, and/or inspection system 300 of FIG. 3C, may include various additional devices that are not explicitly illustrated. For example, a camera head and/or push-cable may be fitted with a sonde device (not illustrated) for generating a dipole magnetic field from within a pipe or other cavity, which may then be detected by a buried utility locator to determine the position of the sonde (below the ground) at the ground surface. The sonde device may, for example, be a sonde such as those described in co-assigned patents and patent applications including: U.S. Pat. No. 7,221,136, issued May 22, 2007, entitled Sondes for Locating Underground Pipes and Conduits; U.S. Pat. No. 7,298,126, issued Nov. 20, 2007, entitled Sondes for Locating Underground Pipes and Conduits; U.S. Pat. No. 7,863,885, issued Jan. 4, 2011, entitled Sondes for Locating Underground Pipes and Conduits; U.S. patent application Ser. No. 14/027,027, filed Sep. 13, 2013, entitled Sonde Devices Including a Sectional Ferrite Core Structure; and/or U.S. patent application Ser. No. 14/215, 290, filed Mar. 17, 2014, entitled Sonde Devices Including a Sectional Ferrite Core Structure. The content of each of these applications is incorporated by reference herein in its entirety.

In use, an inspection system embodiment including a utility locator device may detect the location of the sonde device, and thereby the location of the camera head deployed within a pipe or other cavity (i.e., the locator being operated above the surface by a user may detect the surface location directly above the sonde within an underground pipe or other cavity). In such an embodiment, the inspection system may determine the location of the inspected area within a pipe or other conduit, and may determine an absolute or relative surface position, such as in the form of latitude/longitude coordinates, via an integrated or coupled GPS receiver or other positioning system device. This information may then be associated and stored in a memory of the locator or other device for use in generating mapping data. In some such system embodiments, a utility locator device, such as the utility locator device 1060 of FIG. 10, may further be configured to receive image or video data and/or other data or information from the camera head, such as via a wireless data connection, and display and/or store images/video from the pipe inspection. This information may be wirelessly communicated via other pipe inspection devices or may, in some embodiments, be coupled via wired connections between the camera head and the locator. The locator may include a processing element for processing and combining locate data, location/position data, and/or images or video from the camera head. The locator may include wired or wireless communication modules for communicating with the camera head or other system devices. The wireless communication module may, for example, be a Bluetooth or WiFi communication module, a cellular data communication module, or other wireless communication modules. In some embodiments, the locator may further be configured to control operational parameters of the camera head and/or other system devices.

Details of example utility locator devices as may be used in combination with the disclosures herein in various system embodiments are described in co-assigned patents and patent applications including: U.S. Pat. No. 7,009,399, issued Mar. 7, 2006, entitled Omnidirectional Sonde and Line Locator; U.S. Pat. No. 7,276,910, issued Oct. 2, 2007, entitled A Compact Self-Tuned Electrical Resonator for Buried Object Locator Applications; U.S. Pat. No. 7,288,929, issued Oct. 30, 2007, entitled Inductive Clamp for Applying Signal to Buried Utilities; U.S. Pat. No. 7,443,154, issued Oct. 28, 2008, entitled Multi-Sensor Mapping Omnidirectional Sonde and Line Locator; U.S. Pat. No. 7,518,374, issued Apr. 14, 2009, entitled Reconfigurable Portable Locator Employing Multiple Sensor Array Having Flexible Nested Orthogonal Antennas; U.S. Pat. No. 7,619,516, issued Nov. 17, 2009, entitled Single and Multi-Trace Omnidirectional Sonde and Line Locators and Transmitters Used Therewith; U.S. Pat. No. 7,825,647, issued Nov. 2, 2010, entitled Compact Line Illuminator for Locating Buried Pipes and Cables; U.S. Pat. No. 7,990,151, issued Aug. 2, 2011, entitled Tri-Pod Buried Locator System; U.S. patent application Ser. No. 13/469,024, filed May 10, 2012, entitled Buried Object Locator Apparatus and Systems; U.S. patent application Ser. No. 13/570,211, filed Aug. 8, 2012, entitled Phase-Synchronized Buried Object Locator Apparatus, Systems, and Methods; U.S. Pat. No. 8,248,056, issued Aug. 21, 2012, entitled A Buried Object Locator System Employing Automated Virtual Depth Event Detection and Signaling; U.S. Pat. No. 8,264,226, issued Sep. 11, 2012, entitled System and Method for Locating Buried Pipes and Cables with a Man Portable Locator and a Transmitter in a Mesh Network; U.S. patent application Ser. No. 13/676,989, filed Nov. 11, 2012, entitled Quad-Gradient Coils for Use in a Locating System; U.S. patent application Ser. No. 13/851,951, filed Mar. 28, 2013, entitled Dual Antenna Systems with Variable Polarization; and/or U.S. patent application Ser. No. 14/446,279, filed Jul. 29, 2014, entitled Inductive Clamp Devices, Systems, and Methods. The content of each of these applications is incorporated by reference herein in its entirety.

As disclosed in the various above-listed incorporated patents and patent applications, a utility locator device may include one or more location or position sensors such as global position system (GPS) sensors, inertial sensors, magnetic sensors and the like. Such sensors may be used to track and interpret motion vectors as the utility locator is moved about its operating surface and/or associate these with absolute position data such as latitude/longitude data or relative position data, such as data relating the position of the locator to reference surface features or objects. This data may be combined with images and/or video to generate combined position and mapping data, which may be associated, stored in a memory, transmitted to other electronic computing devices and systems and the like. As described subsequently herein, such mapping solution data may include data corresponding to location imagery as well as data collected through a pipe inspection by a camera head to reference a ground surface location via a utility locator device and/or other system tool. Pipe inspection imagery and data may be displayed upon the utility locator device display, stored in a memory, and/or transmitted to other devices and systems for archiving, mapping, analysis, and the like.

The camera head 110 of FIG. 1, or other camera head embodiments in accordance with aspects of the present disclosure, may be a camera head with a single imaging module, such as the single imaging module camera head 210 of FIG. 2A-2C, or a camera head with multiple imaging modules such as the multi-imager camera head 310 of FIGS. 3A and 3B. In alternate embodiments, different numbers of imaging and illumination modules may be used. In yet further alternative embodiments, the camera head housing or a front element of the housing may comprise a transparent or translucent material with one or more illumination elements located within the housing. In multi-imaging module embodiments, the imaging modules may be oriented such that they each have a central optical axis with the central optical axis of each imaging module sharing a common point or centroid within the camera head.

Figure 2D:
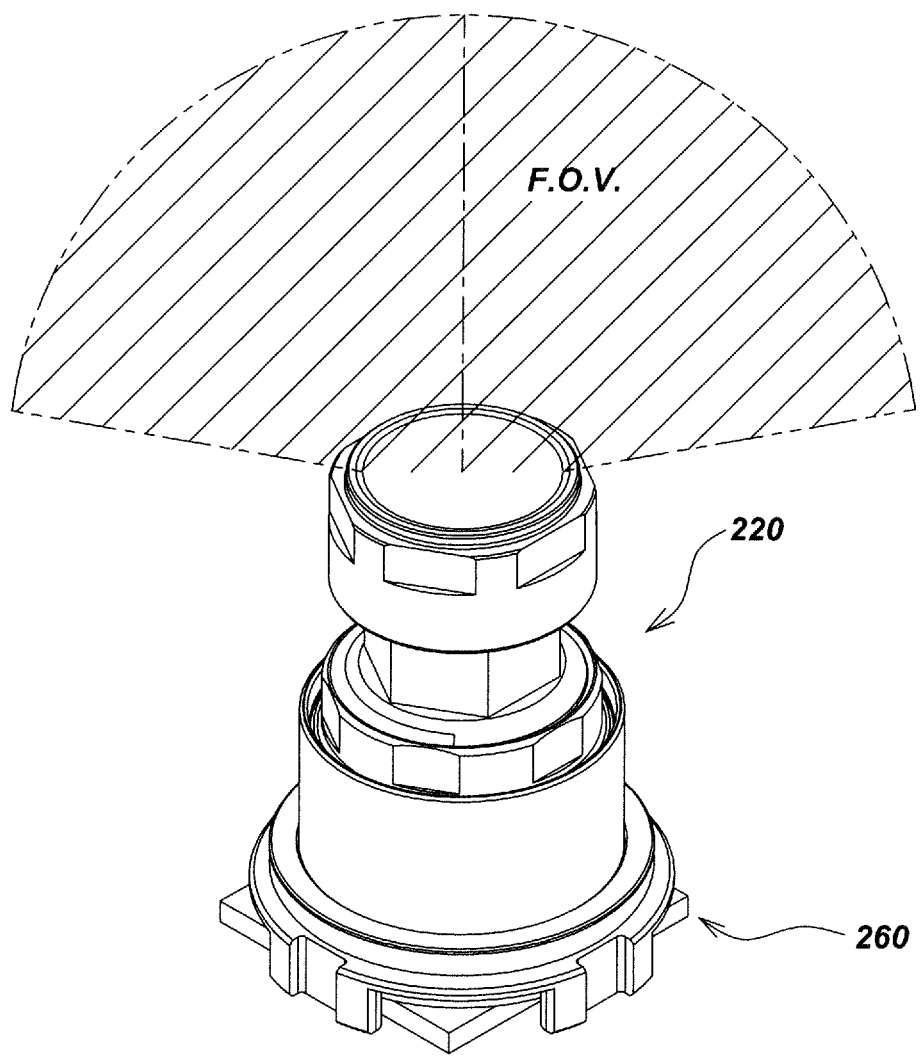
FIG. 2D shows details of an imaging module embodiment, illustrating its field of view.

A field of view (FOV) is illustrated for the single imaging module 220 in FIGS. 2A, 2B and 2D, as well as for a camera head with multiple imaging modules 320-325 in FIGS. 3A and 3B. In FIGS. 3A and 3B, the field of view of some imaging modules has not been illustrated so as to more readily demonstrate the general shape of the field of view along various geometric planes. For instance, the field of view of the front facing imaging module 320 of FIG. 3B is not illustrated in order to better show the field of view of the imaging modules 321-325 along the lower circumference of the front camera head housing 340. Similarly, the field of view of the imaging module 324 illustrated in FIG. 3A is not illustrated in order to better show the field of view of imaging modules 320, 323 and 325. Nevertheless, it will be apparent from FIGS. 3A and 3B that the composite FOV of the multiple imaging modules is significantly greater than that of a single imaging module, even with their individual FOVs overlap to some degree. By stitching images from ones of the multiple imaging modules together in a processing element of the camera head (not shown in FIG. 3A and FIG. 3B), wide-angle composite images and video may be generated covering a wide aggregate field of view around the camera head.

Each imaging module herein, including those where the field of view has not been explicitly illustrated, may have a similar field of view oriented and extending outward about a central optical axis (not illustrated), and the axes of the various imaging modules may intersect at a point or small sphere or centroid. The field of view of each imaging module is typically largely conical, thereby projecting a corresponding circular or oval image area on the imaging sensor, and may be provided from optical elements forming a wide-angle lens. The imaging module 220 of FIGS. 2A, 2B and 2D and imaging modules 320-325 of FIGS. 3A-3B may each have an approximately 160 degree individual field of view in an exemplary embodiment. In some embodiments, each imaging module may be positioned within the camera head so that its field of view is fully or nearly fully overlapped by the field of view of its adjacent imaging modules. In such a camera head embodiment, a three dimensional reconstruction of the inspection area may be generated by stereoscopic image processing algorithms.

In an exemplary embodiment, the camera head includes a housing element having a front portion or element ("front housing element" or "front") and a rear portion or element ("rear housing element" or "body"). The rear housing element or body typically has a portion that is at least partially cylindrical in shape along a longitudinal axis so as to ease deployment within a pipe or cavity and/or minimize catching of the camera head on the pipe interior. The front housing element or front typically includes a portion that is rounded, such as in a dome or half-spherical shape. In various embodiments the front housing element and rear housing element of the housing may be separate elements, or may be a single integral housing element with front and rear portions, or one or both may include multiple components or portions.

As illustrated in FIGS. 2A-2C, the camera head 210 may include a single imaging module 220 and multiple (e.g., five in this exemplary embodiment) illumination modules 230 disposed on or within the front of the housing. In alternate embodiments as described subsequently herein, camera heads may alternately include multiple imaging modules and one or more illumination modules. The imaging modules and illumination modules may be positioned on or within the rounded portion of the front or on a rounded portion of an integral housing in embodiments having an integral housing. The rounded front housing element may be a separate dome element, and the dome element may include multiple openings through which output light from the illumination elements passes. Incoming light, which is focused by optics of the imaging elements, may correspondingly pass through additional openings.

In some embodiments the front housing element may be transparent, and may only have openings for the imaging elements or illumination elements, or, in some embodiments, may have no openings, with incoming and outgoing light passing through the transparent front. In an exemplary embodiment, the front housing element 240 is substantially half-spherical in shape as shown and matches closely in shape with the rear housing element where the front and rear elements join; however, other shapes and sizes may be used in alternate embodiments.

As shown in the embodiment of FIG. 2A, the front housing element or front 240 may mechanically couple to the rear housing element or body 250, either in a removable fashion or, in some embodiments, a permanent fashion. In an exemplary embodiment, the rear housing element has at least a portion that is substantially cylindrical in shape, or entirely or nearly entirely cylindrical in shape, along a longitudinal or axial direction. The two elements may closely align at a coupling point so as to provide a smooth, continuous outer surface of the housing. In some embodiments the housing may be a single integral element rather than separate front and rear elements as shown, and in some embodiments the single integral housing element may be partially or entirely transparent.

Housing body 250 may be formed with a rear housing threaded feature 255 (as shown in FIG. 2A) by which the camera head 210 may couple to a push-cable, such as the push-cable 120 of FIG. 1, and optionally a push-cable spring, such as the push-cable spring 150 of FIG. 1. The imaging module 220 may include optics, mechanical elements such as spacers, optical tubes or housings, lenses, electronics such as processing elements, power circuits, control circuits, and the like, as well as one or more imaging sensors 260 (as shown in FIG. 2C) which generate output data corresponding to images and/or video of an area being viewed. The imaging sensor 260 (FIGS. 2C-2E) may be any of a variety of imaging devices for generating output data corresponding to light projected onto a pixel array of the sensor in the form of digital images or video. In an exemplary embodiment, imaging sensor 260 is a dual pixel high dynamic range imaging sensor such as the OV10640 sold by Omnivision or other comparable imagers. In various embodiments herein, imaging parameters such as exposure, gain, color-balance, ISO setting, and the like may be synchronized at each imaging sensor via interconnecting each imaging sensor and/or simultaneously controlled at a processing element such as an FPGA or other programmable device or module.

Figure 2E:
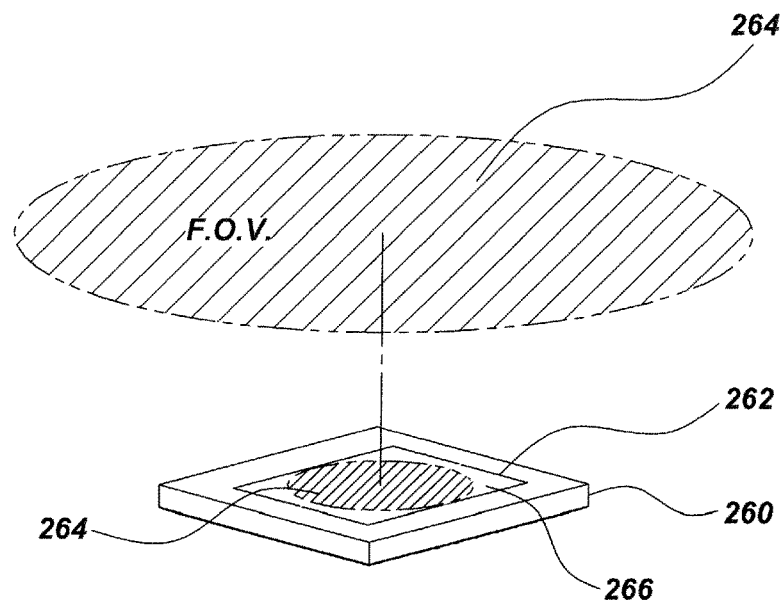
FIG. 2E illustrates an example field of view covered by the active area of a camera head imaging sensor embodiment, in accordance with certain aspects.

As illustrated in FIGS. 2D and 2E, the imaging sensor 260 may be positioned at or near the back of the largely cylindrical imaging module 220. Optics, in the form of one or more lens elements (not illustrated) within imaging module 220, which may comprise a wide angle lens in an exemplary embodiment, may capture a field of view 264 within a pipe or other inspection area. This field of view 264 may be projected upon an imaging sensor active area 262 such that substantially the full field of view area 264 is within the sensor active area 262 (i.e., none of the area of the FOV 264 is outside of the image capture area 262 of the sensor). Such an imaging configuration will typically create an unused sensor area 266 along imaging sensor active area 262 outside the area whereby the full field of view 264 is projected (e.g., a circle or oval) that may be disregarded in processing.

Figure 2F:
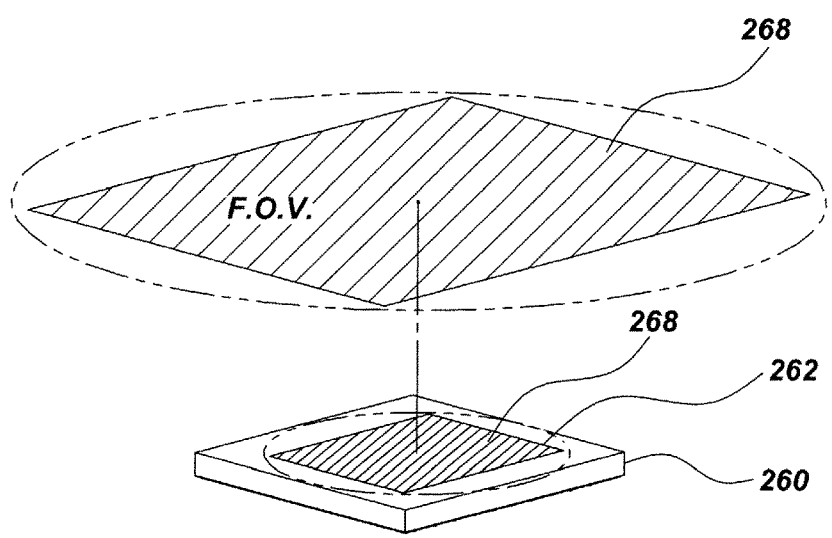
FIG. 2F is an illustration of a traditional field of view covered by the active area of an imaging sensor in a camera head, showing truncation of certain areas of the FOV.

In the various camera head and imaging modules disclosed herein, the larger field of view captured using imaging sensor and optics spacing as illustrated in FIG. 2E to project an area under view entirely within a rectangular or circular active imaging area as shown may be used to provide all or most of the optically available information about an area under inspection. This is contrasted against traditional imaging schemes as shown in FIG. 2F, where only part of the field of view 268 is captured on the active area of an imaging sensor (i.e., the rectangular or square active imaging area of the sensor is circumscribed by the circular or elliptical area covered by the field of view, thereby leaving areas of the circular or oval field of view un-imaged by the sensor). In various camera head embodiments and systems described herein having multiple imaging modules, a full larger field of view captured by each imaging sensor may be used to provide stitching and/or combining of adjacent images in a way that is less computationally intensive and thus less taxing on an FPGA and/or other processing element(s).

While some embodiments may employ a traditional imaging scheme such as that illustrated in FIG. 2F, in one exemplary embodiment an imaging module configuration capturing the full optically generated field of view on the imaging sensor, such as shown in FIG. 2E, may preferably be used.

As illustrated in FIG. 2C, the imaging sensor 260 may provide an output signal to a processing element 270, which may be disposed in camera head 210 or, in some embodiments, remote from the camera head, such as in a CCU or other system device. The output signal from the imaging sensor or sensors may include data representing captured images or video, and may further include additional data such a video or image formatting information, sensor control data, sensor output data, thermal data, and the like.

One or more position/motion/orientation sensors 275, such as inertial navigation and/or position sensors, which may include one or more gyro sensors, one or more compass sensors, and/or one or more one or three-dimensional accelerometer sensors (not shown) for sensing the tilt/orientation, motion, position, acceleration and the like of the camera head may be included to sense such conditions and provide corresponding output data signals to the processing element 270 or to other processing elements (not shown). Camera head 210 may further, or in lieu of inertial navigation and/or other position sensors, utilize motion tracking analysis based on captured images or video.

In operation, inertial navigation sensors, motion tracking data and/or other position sensors may track movement/position of the camera head 210 within a pipe or other conduit and generate corresponding data. Such data may be stored and/or used for various signal processing algorithms, such as determining an ideal frame rate at which to run imaging sensor 260. Sensor information 275 and information stored in memory 280 may be provided to the processing element 270. Additional sensors, such as temperature sensors, acoustic sensors, and/or other sensors may be used to generate additional information, such as data signals corresponding to temperature, sound, and/or position, which may be processed in the processing element 270. The processing element 270 may provide data and/or image or video output signals to a video output module 285. Information corresponding to movements of camera head 210 may be communicated to a utility locator and/or other system devices. Such information may further be used to generate maps of the inspected pipe, cavity or other inspection area. The processing module(s) described herein may reside within a camera head, a camera control unit (CCU) and/or other electronic computing devices or system. In some embodiments the processing module may comprise multiple processing elements sharing processing within various system devices.

Still referring to FIG. 2C, the video output module 285 may supply a composite output signal to a display element 290 via reel 295. The composite output signal may be stitched or tiled wide-angle image or video data corresponding to areas imaged across multiple imaging elements and combined in the processing element. In various embodiments the composite output signal may be communicated to a display element 290 utilizing wired and/or wireless communication links. Reel 295 may store a push-cable, such as push-cable 120 of FIG. 1. The display element 290 may be a camera control unit (CCU), electronic computing device, utility locator, tablet device, smart phone and/or other device in communication with the camera head. Output images, video, sensor data, and/or other data or information may also be stored and/or transmitted to other communicatively coupled devices, such as notebook computers, cellular phones, tablet devices and the like. Likewise, data and information from other system devices may be communicated back to the display element 290, reel 295, camera head 210 and the like. For example, information from a utility locator device (not illustrated), such as locate data, positional data, environmental sensor data, control data and the like may be communicated to the devices illustrated with pipe inspection system 200 of FIG. 2C and vice versa.

FIGS. 3A-3C illustrate details of another exemplary camera head embodiment 310 including a plurality of imaging modules and a plurality of illumination modules. Camera head 310 may include multiple imaging modules 320, 321, 322, 323, 324 and 325 and multiple illumination modules 330 disposed within a rounded front housing element 340 that is coupled to a rear housing element 350 either in a removable or fixed fashion. Camera head 310 and housing element 340 and 350 may be similar to corresponding element of camera head embodiment 210 but with different numbers of imaging and illumination modules and corresponding openings. In some embodiments the housing elements may be transparent or translucent to allow light to pass into or out of the housing element and associated imaging and/or illumination modules.

The front 340 may couple to the rear housing element 350, which may include a rear housing threaded feature 355 or other attachment mechanism. In some embodiments the front and rear housing elements may be integral in a single housing element or structure. Camera head 310 may couple to a push-cable, such as the push-cable 120 of FIG. 1 or other push-cables as are known or developed in the art, and optionally to a push-cable spring such as the push-cable spring 150 of FIG. 1.

The imaging modules 320-325 may include an imaging sensor 360-365 (as shown FIG. 3C) for capture image and/or video data of a work area such as the interior of a pipe or other cavity. The imaging modules 320-3225 may be oriented in the camera head 310 so that they have a central axis and the central axes each share a common point or centroid within the camera head. In an exemplary embodiment, the imaging sensors 360-365 may be dual pixel high dynamic range imagers such as the OV10640 imaging sensor made by Omnivision or other comparable imagers.

In various embodiments herein, exposure, gain, color-balance and/or other imager parameters such as exposure triggering or video frame synchronization may be synchronized at each imaging sensor via interconnecting each imaging sensor, and/or may be simultaneously controlled at a processing element such as an FPGA or other processor or programmable computing device. In a typical embodiment where images from each of the sensors are digitally stitched or tiled together, images may be captured from each imaging sensor substantially simultaneously and may have the same control/image parameter settings to aid in seamless compositing of the multiple images or video streams from the imaging sensors.

The inspection area captured by the field of view of each imaging module 320-325 may be the same as or similar to the field of view described with respect to FIGS. 2D and 2E. For example, each imaging module 320-325 may image the entire field of view on its corresponding imaging sensor 360-365 (i.e., an oval or circular field of view may be entirely within or circumscribed by a square or rectangular active imaging area) or, in some embodiments, the field of view may extend beyond the active imaging area of the imaging sensor (i.e., a circular or oval field of view may extend beyond the square or rectangular imaging area).

In embodiments where a camera head includes multiple imaging modules, such as camera head embodiment 310 of FIGS. 3A-3C, digital tiling and/or image stitching algorithms may be used to generate one or more composite images or video streams of the inspected area by tiling or stitching output images from each of the imaging modules. A camera head and camera control unit or other display element may further provide digitally simulated articulation within captured images and/or video based on processing of images from the imaging modules or composite stitched or tiled images. Details of methods and apparatus for implementing digital tiling, image stitching, and/or digitally simulated articulation within a pipe inspection camera and system as may be combined in various embodiments with the disclosures herein are described in co-assigned applications including U.S. patent application Ser. No. 13/913,485, filed Jun. 9, 2013, entitled Multi-Camera Pipe Inspection Apparatus, Systems and Methods and U.S. patent application Ser. No. 14/207,089, filed Mar. 12, 2014, entitled Multi-Camera Pipe Inspection Apparatus, Systems, and Methods. The content of each of these applications are incorporated by reference herein in their entirety.

Turning to FIG. 3C, the imaging sensors 360-365 of the pipe inspection system 300 may provide output from corresponding imaging modules as output data to a processing module 370, or optionally to a signal selector module 368, which may both be disposed in camera head module 310. The signal selector 368 or multiplexer (MUX) may be used to increase the amount of data that can be sent over the network within a certain amount of time and bandwidth. For example, signal selector 368 may select and combine multiple analog or digital input information signals, such as, for example, image signals provided from imaging sensors 360-365, and may forward the selected or combined input into a single and/or multiple output signals.

One or more motion/position/orientation sensors 375, such as inertial navigation and/or position sensors, which may include one or more gyro sensors, one or more compass sensors, and/or one or more multi-axis accelerometer sensors (not shown) for sensing the tilt/orientation of the camera head may be included to sense such parameters. Camera head 310 may further, or in lieu of inertial navigation and/or other position sensors, use motion tracking analysis algorithms implemented in a processing element to determine position, orientation and/or motion information. Imaging information may further be used with other sensor data from the sensors 375 to determine navigation and/or position/location information using tracking or orientation algorithms based in part or fully on captures images or video. Further details of apparatus and methods for using optical information and INS and/or other position sensor information in conjunction with details disclosed herein is described in co-assigned patent applications including: U.S. patent application Ser. No. 13/766,670, filed Feb. 2, 2013, entitled Optical Ground Tracking Locator Devices & Methods; U.S. patent application Ser. No. 14/215,239, filed Mar. 17, 2014, entitled Optical Ground Tracking Apparatus, Systems, and Methods; and U.S. Patent Application No. 62/019,715, filed Jul. 1, 2014, entitled Stereo Optical Ground Tracking Apparatus, Systems, and Methods. The content of each of these applications is incorporated by reference herein.

In use, inertial navigation sensors, motion tracking and/or position sensors may track movement/position of the camera head 310 within a pipe or other conduit. This information may be used for various functions such as determining an optimal frame rate at which to operate imaging sensors 360-365. Sensor information 375 and information stored in memory 380 may be provided to the processing module 370. Additional sensors, such as temperature sensors, acoustic sensors and/or other position or environmental sensors may be used to generate additional data, such as data corresponding to temperature, sound and/or position, which may be later processed in the processing element 370 and associated with imagery data and/or used for control functions within the camera head or inspection system. The processor 370 may provide an output composite image or video signal to a video output module 385 which may be rendered on a display device, stored in memory, transmitted to another local or remote electronic computing system, and the like.

Still referring to FIG. 3C, in the pipe inspection system 300, the video output module 385 may supply a composite video signal to a display element 390 via cable reel 395. In various embodiments, a composite video or still image signal may be communicated to a display element 390 utilizing wired and/or wireless communication modules. Reel 395 may include a push-cable, such as push-cable 120 of FIG. 1. The display element 390 may be a camera control unit (CCU), computing device, utility locator, and/or other device in communication with the camera head. Output images, video, sensor data, and/or other data or information may also be stored and/or transmitted to other communicatively coupled devices, such as notebook computers, cellular phones, tablet devices and the like. Likewise, data and information from other system devices may be communicated back to the display element 390, reel 395, camera head 310 and so forth. For example, information from a utility locator device (not illustrated) may be communicated to the devices illustrated with pipe inspection system 300 of FIG. 3C and vice versa. For instance, information descriptive of movements of camera head 310 may be communicated to a utility locator and/or other system devices. Such information may further be used to generate mapping data of the pipe, conduit or other inspection area.

Figure 3D:
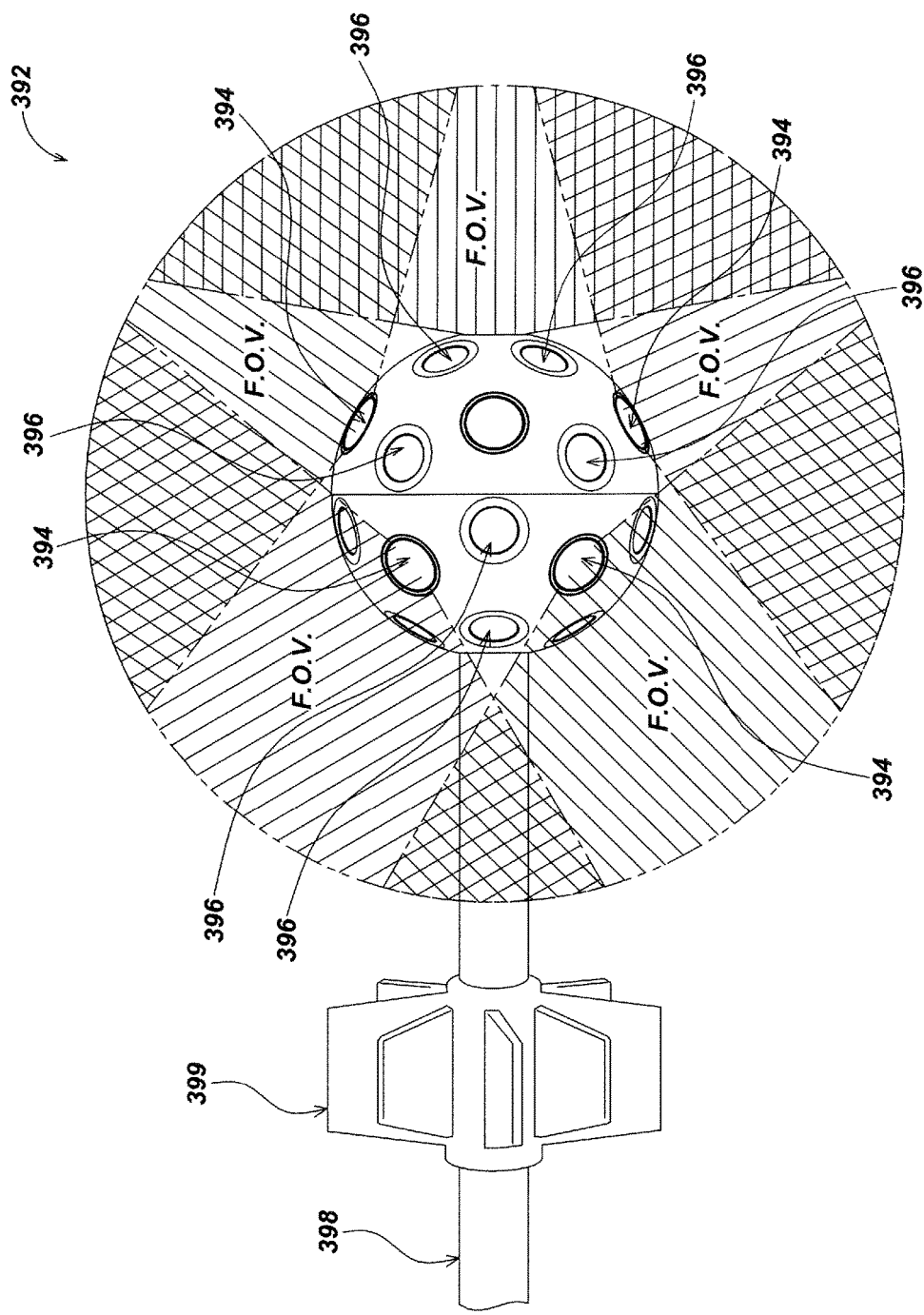
FIG. 3D is a side view of a camera head embodiment with a spherical head, illustrating its field of view.

In various embodiments, camera heads may be spherical, ellipsoidal, cylindrical, conical, and/or otherwise be partially or fully rounded or curved in shape. For example, the spherical camera head 392 illustrated in FIG. 3D may include imaging modules 394 oriented to generate imagery, which may be photosphere like composite images or video, of its surroundings on all sides. The field of view from each imaging module 394 may overlap with neighboring ones of the imaging modules 394. In some embodiments, each imaging module may be configured such that its field of view is fully overlapped by the field of view of adjacent imaging modules. Illumination modules 396 may allow for the entirety of the inspection area captured by the imaging modules 394 to be illuminated in approximately a uniform fashion. Camera head 392 may be secured about the end of a push-cable 398, which may further have one or more pipe guides, such as the pipe guide 399 shown. In use, the pipe guide(s) 399 may hold the camera head 392 away from a pipe's walls at a reference distance on all sides, thus permitting the imaging modules 396 to image the entirety of the pipe interior.

Figure 4A:
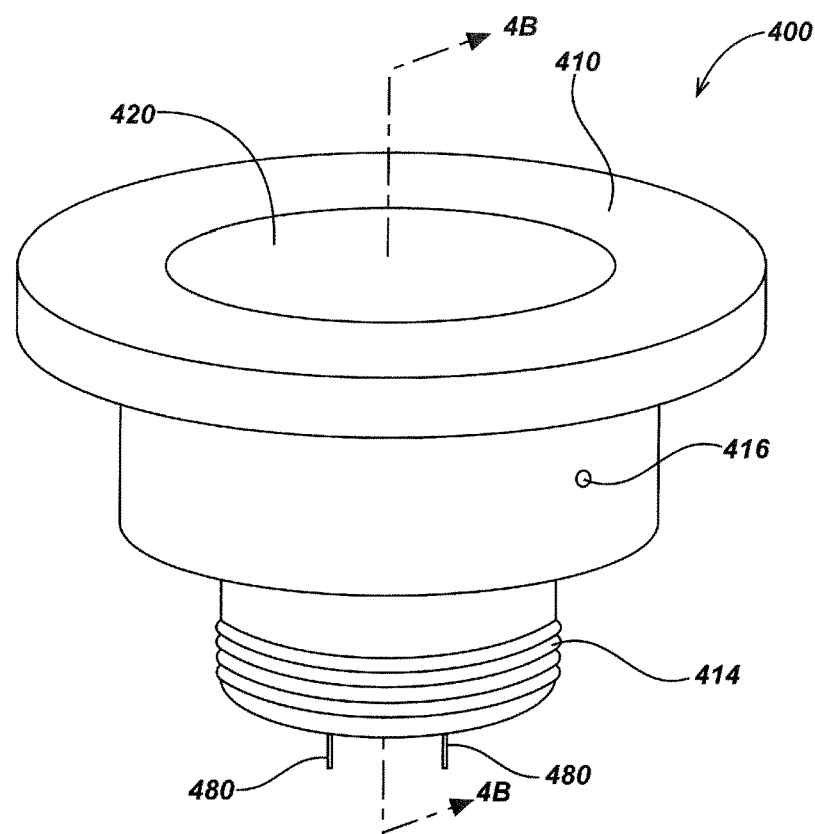
FIG. 4A is an isometric view of details of an illumination module embodiment, in accordance with certain aspects.
Figure 4B:
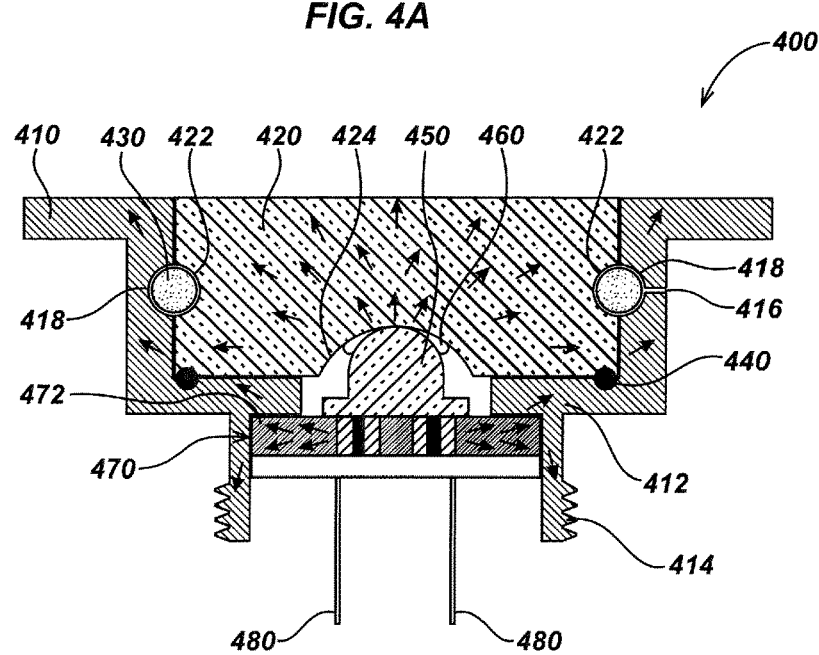
FIG. 4B is a sectional view of details of the illumination module embodiment of FIG. 4A, taken along line 4B-4B.
Figure 4C:
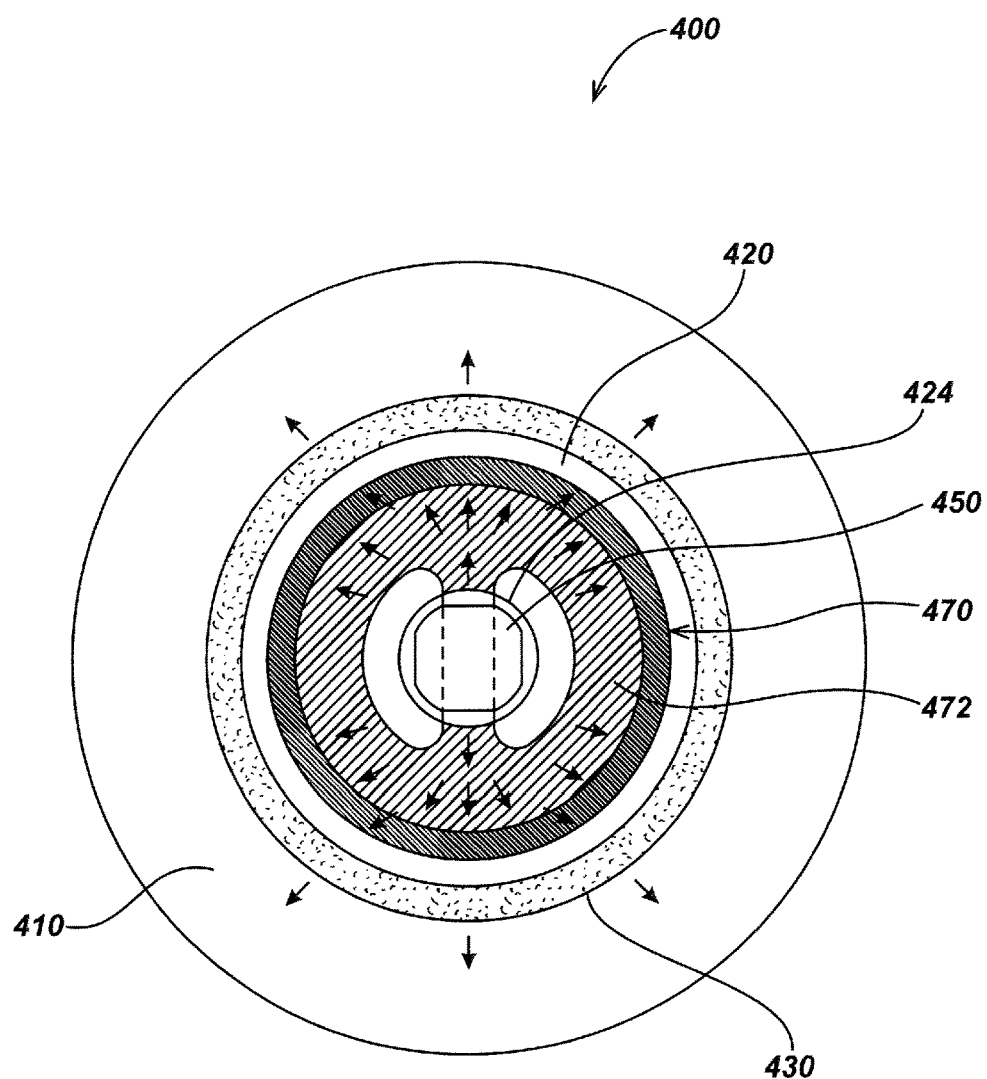
FIG. 4C is a front view of details of the illumination module embodiment of FIG. 4A.

Turning to FIGS. 4A-4C, an exemplary illumination module embodiment 400 is illustrated. This illumination module embodiment may be used in various camera heads or other imaging devices as are described herein, such as in camera head embodiment 200 or 300. Illumination module 400 may have a largely cylindrical illumination module housing 410 formed to allow a window 420 to seat within one end. For example, illumination module housing 410 may have a shelf feature 412 (as shown FIG. 4B) of reduced diameter formed within the opening behind where the window 420 is seated. The illumination module housing 410 may include a threaded feature 414 and/or other securing element permitting the illumination module 400 to couple to a camera head and/or other device. Illumination module 400 may further include an adhesive access hole feature 416, through which adhesive may be injected during manufacture to fill an annular groove formed between window 420 and illumination module housing 410. This may be done by forming an annular gap by aligning window annular gap feature 422 on window 420 with housing annular gap feature 418 on illumination module housing 410.

Figure 5:
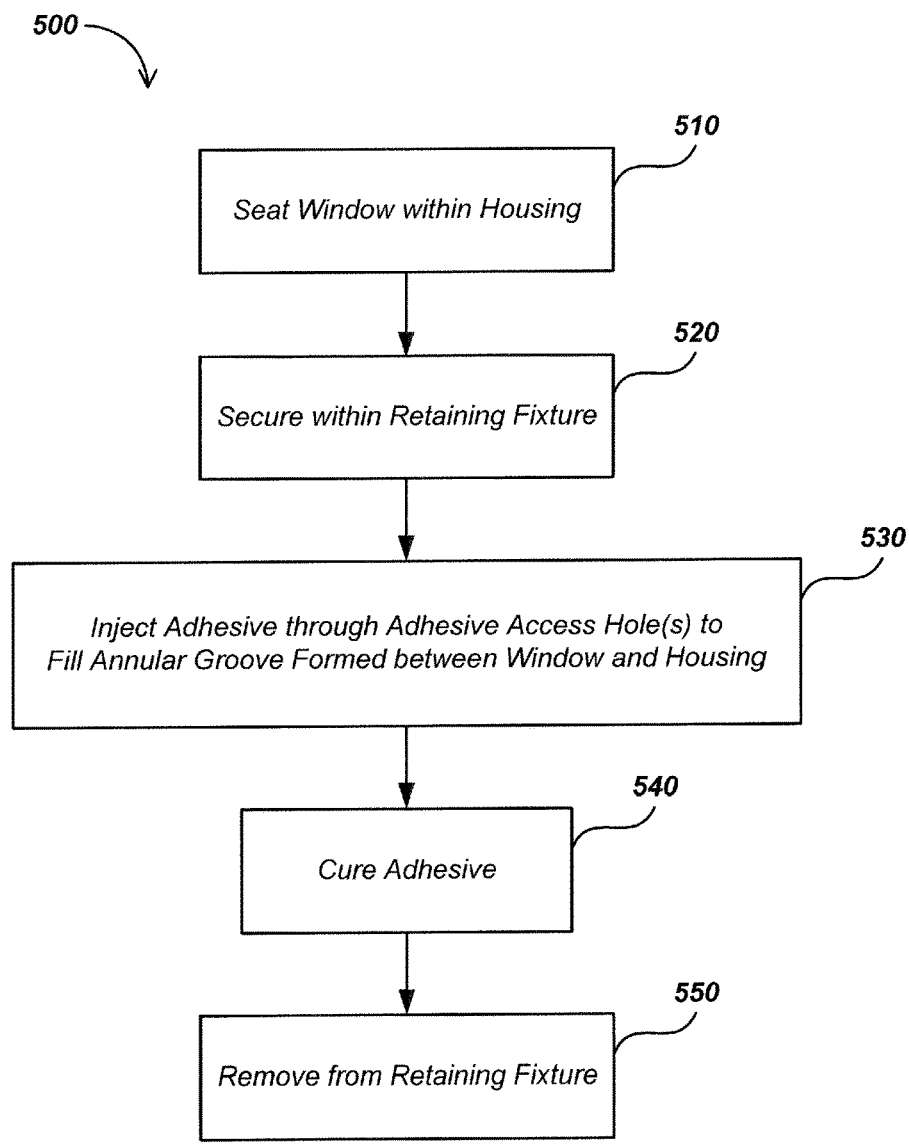
FIG. 5 is a block diagram illustrating details of an embodiment of a method for securing a window in place in a camera head or other device.

Turning to FIG. 5, an embodiment of a method 500 for securing a window to a camera head or other housing is illustrated. This method may be used with various illumination or imaging modules as described herein, such as for securing window 420 into illumination module housing 410, as well as for imaging modules as described herein. The method may include a first stage 510 of seating the window within the end of its housing. In stage 520, a retaining fixture, such as the retaining fixture 610 illustrated in FIG. 6, may secure the window in place. In stage 530, adhesive may be injected into an annular groove formed between the window and housing. An example is the annular groove formed in illumination module housing 410 of FIG. 4B between window 420 and illumination module housing 410 when a window annular gap feature 422 on window 420 aligns with housing annular gap feature 418.

Figure 6:
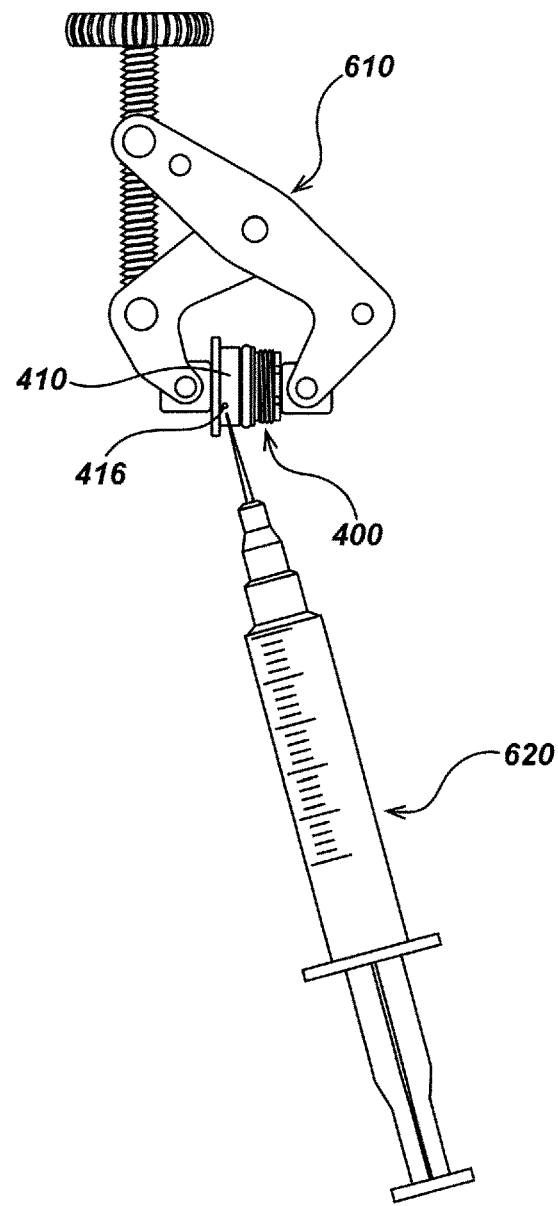
FIG. 6 illustrates details of implementation of the method embodiment of FIG. 5.

As illustrated in FIG. 6, an adhesive dispenser 620 may be used to inject adhesive 430 (as shown in FIG. 4B) into the annular groove on illumination module housing 410 of illumination module 400 via adhesive access hole feature 416. The annular fill of adhesive, when cured, may be used to hold a window securely in place, as well as form a seal preventing external materials/contaminants from entering the illumination module and/or elsewhere in the camera head. In some embodiments, one or more O-rings may be positioned between the window and housing to aid in sealing the illumination module. For example, illumination module 400 as illustrated in FIG. 4B may include an O-ring 440 to provide an optional secondary seal to protect entry of external environmental contaminants. In stage 540, the adhesive may be cured. Once the adhesive has been cured, in stage 550 a retaining fixture, such as the retaining fixture 610 illustrated in FIG. 6, may be removed. The method 500 may further be used to secure a window into housing in various other devices, for example securing windows in an imaging module, and should not be construed as limited to illumination modules as described in the present disclosure.

Referring back to FIGS. 4A-4C, the window 420 may comprise sapphire or other transparent material(s). The material(s) used in window 420 may have a high refractive index value and high thermal conductivity to maximize light output through window 420 as well as aid in channeling heat (indicated by small arrows in FIGS. 4B and 4C) from internal components to the outside environment through window 420. In an exemplary embodiment, sapphire may be used; however, other transparent materials may also be used in alternate embodiments.

A cavity feature 424 may be formed on an interior side or face of the window 420. The cavity may, for example, be a scooped out shape or largely fully or partially hemispherical cavity feature 424 (as shown in FIG. 4B), which may be formed or carved out centrally on the internally oriented side or facing of the window 420. The cavity feature and may be shaped to accommodate a corresponding outer surface of light emitting diode (LED) 450 (or other illumination devices) so that at least a portion of the LED 450 outer surface presses into the surface of the window 420 within the hemispherical cavity feature 424 and forms a close contact for coupling light to the window 420 and conducting heat to the window 420 from the LED. In an exemplary embodiment, the recessed feature 424 may be positioned substantially centrally in the window as shown in FIG. 4B to accommodate a corresponding single LED. In other embodiments, multiple recessed features may be formed in the window and may be used with corresponding multiple illumination devices so that each illumination device has its own cavity in the window (or windows).

In an exemplary embodiment, the LED 450 may be an XLamp® XP-L LED available from Cree®, or another comparable illumination device. Optional silicon grease 460 may be applied within the hemispherical cavity feature 424 where the LED 450 contacts window 420. In use, the hemispherical cavity feature 424 allows the LED 450 to be positioned towards the outer surface of the illumination module 400 to provide a wide angle of dispersion of the output light. By having the LED 450 contact the surface of window 420, internal Fresnel reflections may be reduced, and the LED 450 may be thermally coupled to window 420 to aid in dispersing heat through window 420 to the external environment and away from sensitive internal components. LED 450 may secure to a PCB 470, which may be configured to provide power and/or control signals to control LED 450. PCB 470 may further include a thermal flood substrate 472 that may thermally couple to LED 450 to disperse heat. The thermal flood substrate 472 may comprise copper and/or other high thermal conductivity materials. The thermal flood substrate 472 may further contact the illumination module housing 410 to disperse heat to the housing. One or more electrical connectors 480 may connect to PCB 470 to communicate signals and supply power to PCB 470 and ultimately LED 450.

Although better in efficiency than traditional lighting devices such as incandescent bulbs, high brightness LEDs can still generate significant heat, and removing this heat is important for maximizing LED life as well as reducing heating of other camera head components. In one aspect, camera head embodiments may including electronic circuitry to selectively control the light output of LEDs or other illumination devices to provide high brightness for imaging while reducing heating by minimizing output during non-imaging time intervals. For example, in some embodiments LED light output from the illumination modules may be selectively controlled by instructions programmed in a processing element or elements so as to be at a maximum level during time intervals when imaging is being done by imaging modules, and light output may be reduced or turned off during other time intervals.

Figure 7A:
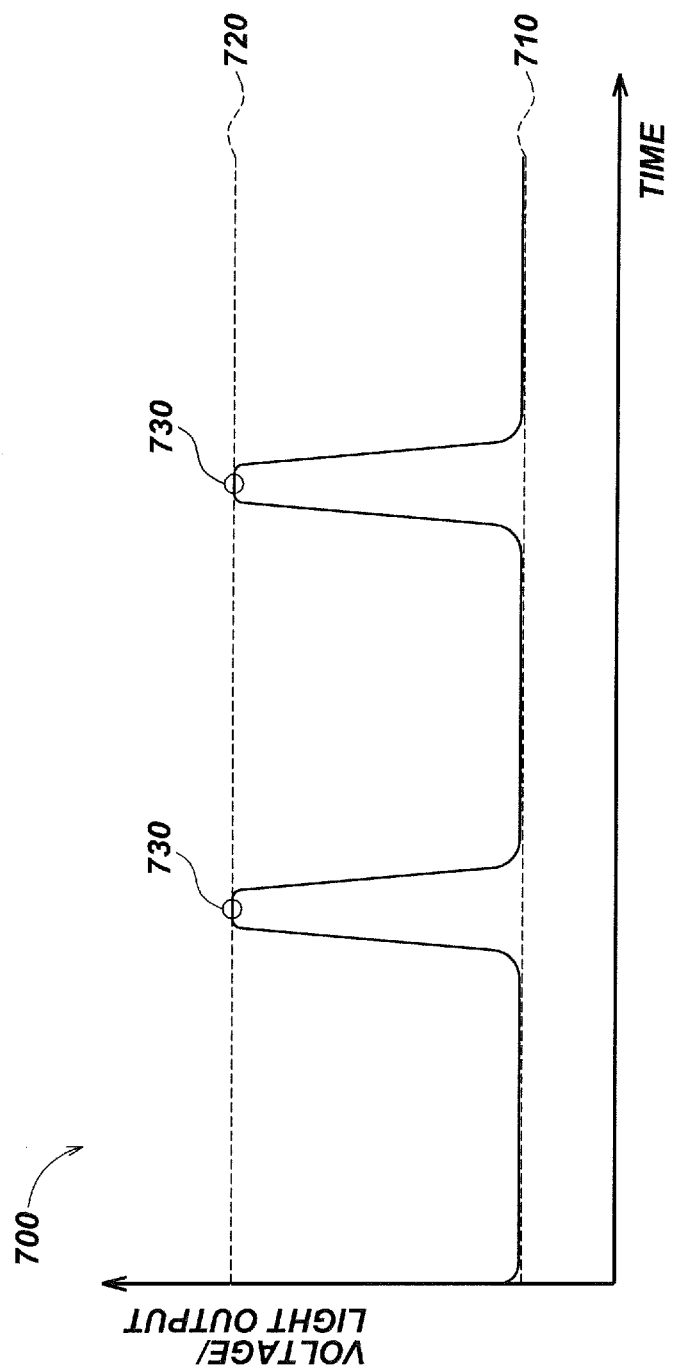
FIG. 7A is an diagram illustrating an embodiment of a method for providing power signaling to increase and decrease light output for generating high resolution imagery of an inspection area, in accordance with certain aspects.
Figure 7B:
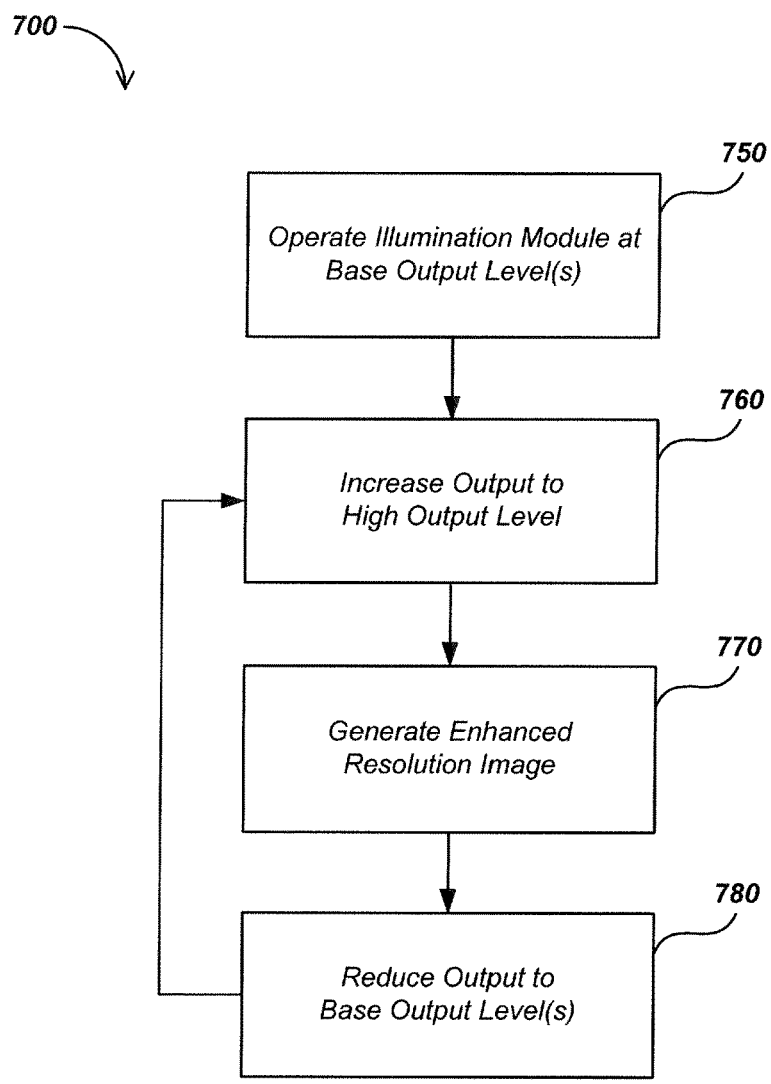
FIG. 7B is a block diagram illustrating details of the method embodiment of FIG. 7A.

Turning to FIGS. 7A and 7B, an embodiment of a method 700 for providing selectively controlled illumination is described. Method embodiment 700 may be used to selectively control light output to enhance visibility/image quality within an inspection area while maintaining an acceptable thermal load and preventing overheating of the illumination module, imaging modules and/or other camera head components. This may be done by providing a high/maximum level of output light (level or voltage 720) at periodic times 730, and providing a lower level of light (or no light) during other time intervals. As shown in FIG. 7A, an illumination module or other camera head electronic circuitry may implement method 700 in a processing element by periodically increasing applied voltage to the LEDs, and thereby light output from the LEDs, to a maximum output level 720.

During the remaining time intervals, the applied LED voltage may be lowered or turned off, resulting in lower output light levels or no output light. This method may be used to provide an acceptable thermal load by minimizing heating during time intervals when imaging is not being done by the imaging modules, while providing a maximal light output during time intervals when images or video are being captured. The high output duty cycle is typically small so that the LED is generating significant heating only during a small percentage of its overall operational time.

In an exemplary embodiment, a base output level 710 providing 500 lumens may periodically, or in some embodiments at variable or user-selected times, be increased to a high output level 720 of 10,000 lumens by increasing voltage to the LED or other light source for a short duration of time. This increase in voltage/light output at the high output level 720 may occur, for instance, once every second for a duration of approximately 50 milliseconds (i.e. a 5% duty cycle). Imagery of enhanced resolution (e.g. due to reduced noise at the imaging sensors due to higher light output, etc.) may be generated during the periodic increases in voltage/light output at the maximum output level 720 about times 730. For example, an enhanced resolution image may be generated from a shortened exposure, such as a 1 millisecond exposure, during the duration of high output 720 (e.g., 50 mS, with the imaging done at approximately the midpoint of the 50 mS window). In camera head embodiments with multiple imaging modules, each enhanced resolution image may comprise multiple images and/or a composite image based on multiple images from different imaging sensors and/or a high dynamic range (HDR) image or images. The composite image may be a panoramic image creating a photo sphere effect at each instance of enhanced resolution image capture (i.e., at times 730).

As shown in FIG. 7B, method 700 may include a first stage 750 where the illumination module(s) operate at the base output level 710 (as shown in FIG. 7A). At stage 760, voltage applied to the LEDs may be increased to correspondingly increase light output to high output level 720 at certain time intervals, which may be periodic. For example, voltage/light output may be increased to high output levels 720 once every second for 50 milliseconds. At stage 770, an enhanced resolution image may be captured by imaging sensor(s) of the imaging modules during or within the interval of high light output levels 720 reached during stage 760. The enhanced resolution image may, for instance, occur during a 1 millisecond exposure centrally timed during the duration of high output levels 720. At stage 780, the voltage/light output may be lowered to the base output level 710 (or to another lower light output level) which, in some embodiments, may be off or zero light output. The method 700 may be repeated as desired throughout the inspection process. In some embodiments light output may be varied in other stages through continuous or stepped output levels. This may be done in synchronization with imaging sensor operation, such as in synchronization of imaging timing and/or duration with particular imaging parameter settings such as color balance, aperture setting, shutter speed setting, light filtering adjustments and the like.

In some camera head embodiments having multiple illumination modules various switching methods may be used to illuminate the inspection area by periodically varying voltage and thereby light output during different time intervals between each illumination module and/or between sets of illumination modules. This may be done to further control thermal loading or to provide variable lighting for different sub-areas with an overall inspection area or to otherwise vary lighting levels, duration and/or area under illumination. An example of this is illustrated in method embodiment 800 of FIG. 8B in conjunction with the timing chart of FIG. 8A, which shows selective control of individual illumination module light output. Method 800 may be implemented using a first illumination module set 802 and second illumination module set 804 (each set having one or more illumination modules). Additional illumination module sets having one or more illumination modules may be used in various alternate embodiments. The illumination module outputs and/or associated imaging module imaging operations may be controlled by one or more processing elements electronically coupled to the illumination modules and/or imaging modules.

The first and second illumination modules 802 and 804 may each be comprised of one or more different illumination modules located on the same camera head. For example, in a camera head having ten illumination modules, five illumination modules may be included in a group comprising the first illumination module set 802 and the remaining five may be included in a group comprising the second illumination module set 804. In some camera heads, method 800 may be adapted to using any number of illumination modules and/or grouping of illumination modules in sets.

Figure 8A:
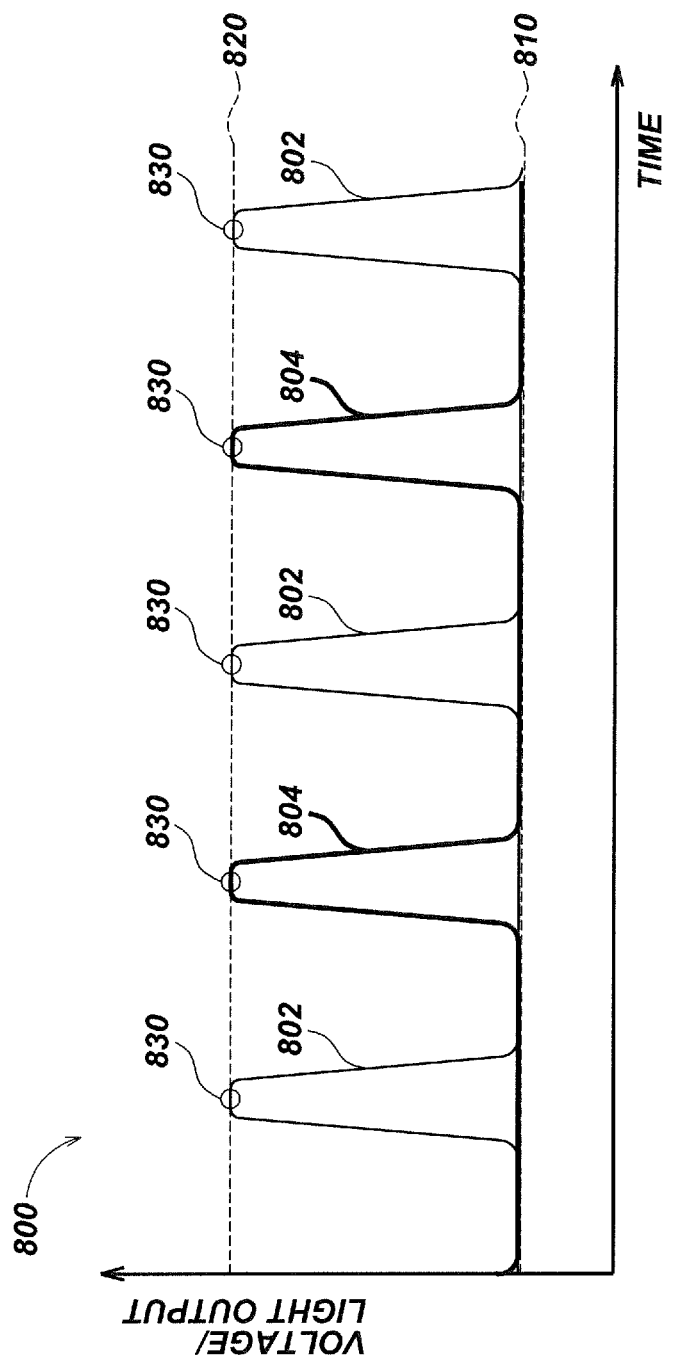
FIG. 8A is a diagram illustrating details of an embodiment of a method for providing power signaling to increase and decrease light output for generating high resolution imagery of an inspection area, in accordance with certain aspects.

As best illustrated in FIG. 8A, the first and second illumination module sets 802 and 804 may each increase in voltage/light output from base output level 810 to high output level 820 at different time intervals. An enhanced resolution image may be produced from a shortened exposure at each duration of high output 820 (at or around times 830) for the first and second illumination modules 802 and 804. In camera head embodiments with multiple imaging modules, each enhanced resolution image may include multiple images and/or a composite image composed of multiple images from the same or different imaging sensors such as described with respect to method embodiment 700. The composite image may be a panoramic type image creating a photo sphere type effect at each instance of enhanced resolution image allowing a user to view a wide section of inspection area or may be an HDR image or images or video. Furthermore, enhanced resolution images may be produced by the same or different sets of imaging modules within the camera head in alternate embodiments.

Figure 8B:
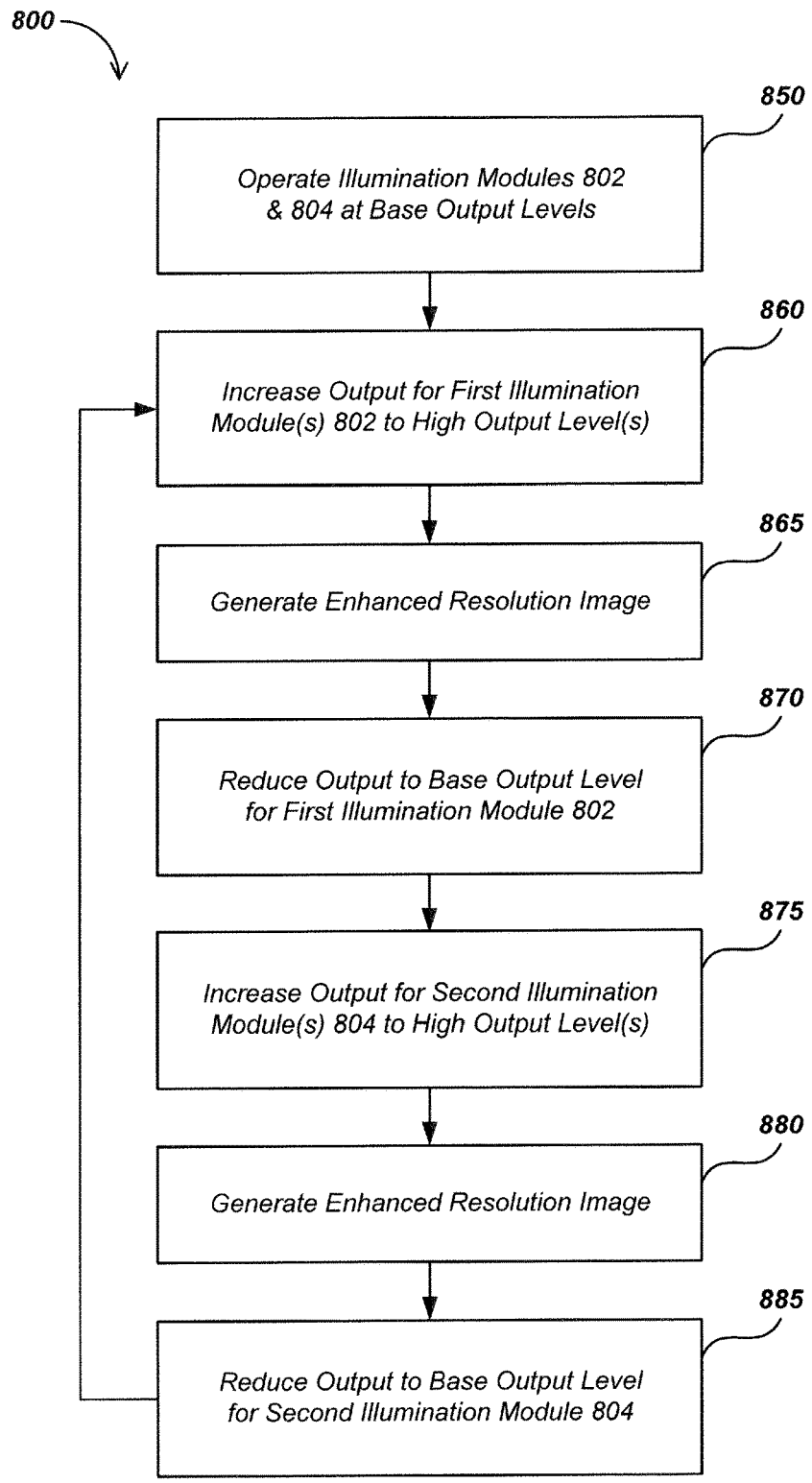
FIG. 8B is a block diagram illustrating details of the method embodiment of FIG. 8A.

As shown in FIG. 8B, method 800 may include a first stage 850 where the first and second illumination module sets 802 and 804 are operated at a base output level 810 (as shown in FIG. 8A), which may be a low light output or zero light output. At stage 860, voltage/light output may be increased to a higher or maximum output level 820 at the first illumination module set 802, while the second illumination module set 804 remain at base output level 810 (or other lowered output level). At stage 865, an enhanced resolution image may be captured by one or more imaging modules during or within the interval of high output levels 820 reached during stage 860. At stage 870, the voltage/light output for the first illumination module set 802 may be lowered to base output level 810 (or other lowered output level). At stage 875, voltage/light output may be increased to high or maximal output level 820 (or to another higher light output level) for the second illumination module set 804, while the first illumination module set 802 remains at base output level 810 (or a lowered output level relative to the maximal output level). At stage 880, an enhanced resolution image may be captured during the interval of high output levels 820 (or at a different, higher light output level) reached during stage 875. In a subsequent stage 885, the voltage/light output of the second illumination module set 804 may be lowered to the base output level 810 (or another lowered output level. Method 800 may then be repeated starting back at step 860, either periodically or at varying time intervals such as in response to user actuation through a CCU.

Figure 8C:
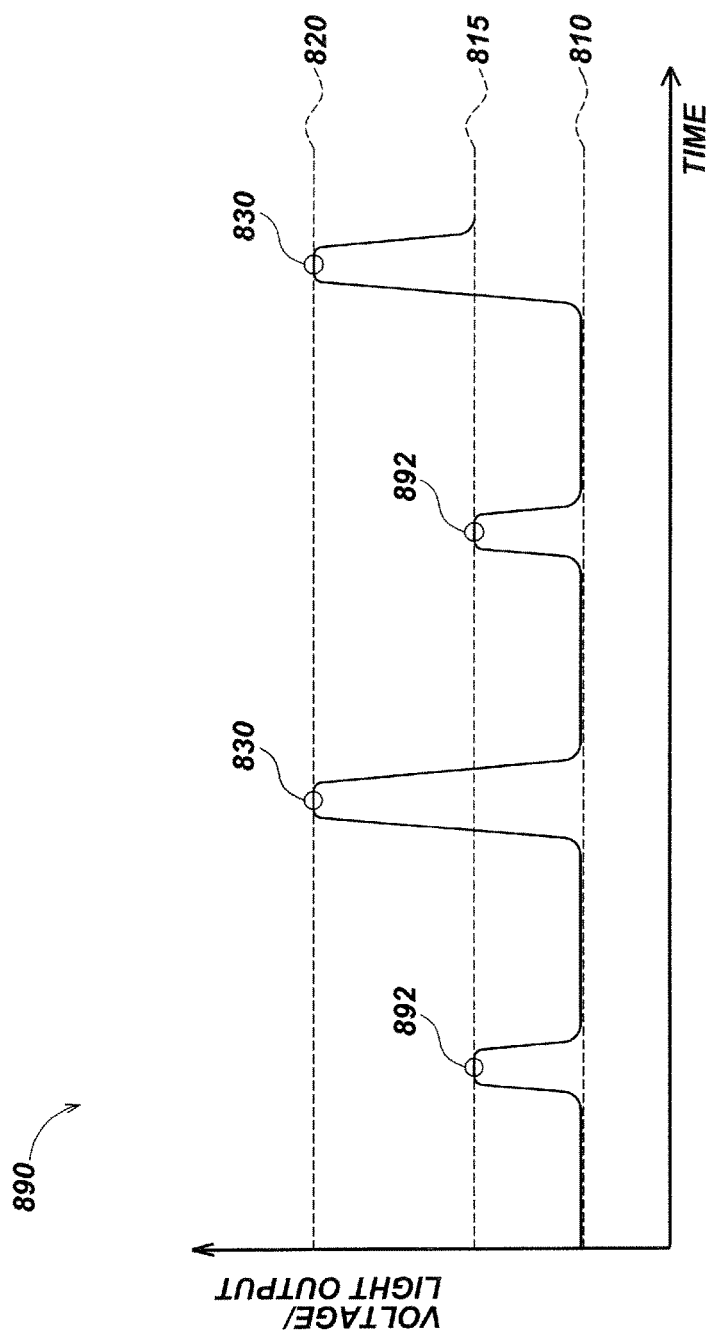
FIG. 8C is a diagram illustrating details of an embodiment of a method for providing power signaling to increase and decrease light output between varied output levels for generating high resolution imagery of an inspection area, in accordance with certain aspects.

In some embodiments, one or more illumination modules may be used to implement a variable output illumination method in which multiple output levels are used. A timing diagram 890 for one embodiment of such an implementation is illustrated in FIG. 8C. In this embodiment, light output from one or more illumination modules may begin at a base output level 810. The output light level may be increased to an intermediate output level 815 at times 892, and then reduced to the base output level 810 (or other lowered output level). Images or video generated at one or more imaging elements, which may be composited into photo sphere imagery based on output images from multiple imaging sensors, may be captured at or within a window about each instance of intermediate output level 815 at times 892. Between each instance of intermediate output level 815, instances of high or maximum output level 820 may be implemented by raising applied voltage, during which an enhanced resolution image may be generated at times 830. In further embodiments, variable numbers of output levels may be used, and varying imaging types and quality levels may be implemented at these variable output levels. In some embodiments continuously adjusted levels may be determined by a processing element of the the camera head or other connected device based on particular illumination needs within a particular inspection area. This may be done by, for example, processing received images or video and adjusting the light output level based on parameters such as overall image brightness or darkness, amount of darkness or brightness in particular image areas, color or contrast information, and the like.

In alternative methods, the intervals of high and/or base output levels may overlap or may vary over time. Furthermore, method embodiment 700 of FIGS. 7A and 7B and/or method embodiment 800 of FIGS. 8A and 8B may be adapted to utilize different numbers of illumination modules and/or sets of illumination modules, as well as correspondingly variable numbers of imaging modules or sets of imaging modules. In some embodiments, switching of different illumination modules and/or sets of illumination modules may be used to provide different shadow or brightness casting within the inspection area or color or other lighting or imaging parameter variations. Processing of images based on differences in shadows, light, color and the like may be used to detect problems or defects in pipes or other cavities being inspected such as cracks, holes, blockages, ingress of roots etc. Applicant of light from a single direction, particularly if the light is uniform and the lack of directionality provides no shadows, can provide less information in images than lighting that provides shadows or areas of high and low contrast. Further, varying lighting output while maintaining imaging sensor parameters may be used to generate composite images that can be processed using HDR algorithms to provide images or video having enhanced detail and additional information.

In yet further methods, switching between base output levels and high output levels may be based on temperatures sensed within the illumination modules, camera head, or other configured device. For example, a temperature sensor may be used to measure temperatures in or around a device and determine when high output levels may be achieved (e.g., due to enhanced heat dissipation from the camera head in cooler environments) and when high output levels must be avoided (e.g., in hotter environments) to prevent overheating of internal components while maximizing visibility of inspection area. For example, a temperature sensor may be coupled to a processing element and/or illumination element, with temperature output data then used by the processing element or illumination element to set lighting duty cycles, maximum light output level, vary light output profiles, adjust imaging sensor operations such as frame rate and the like.

Figure 9:
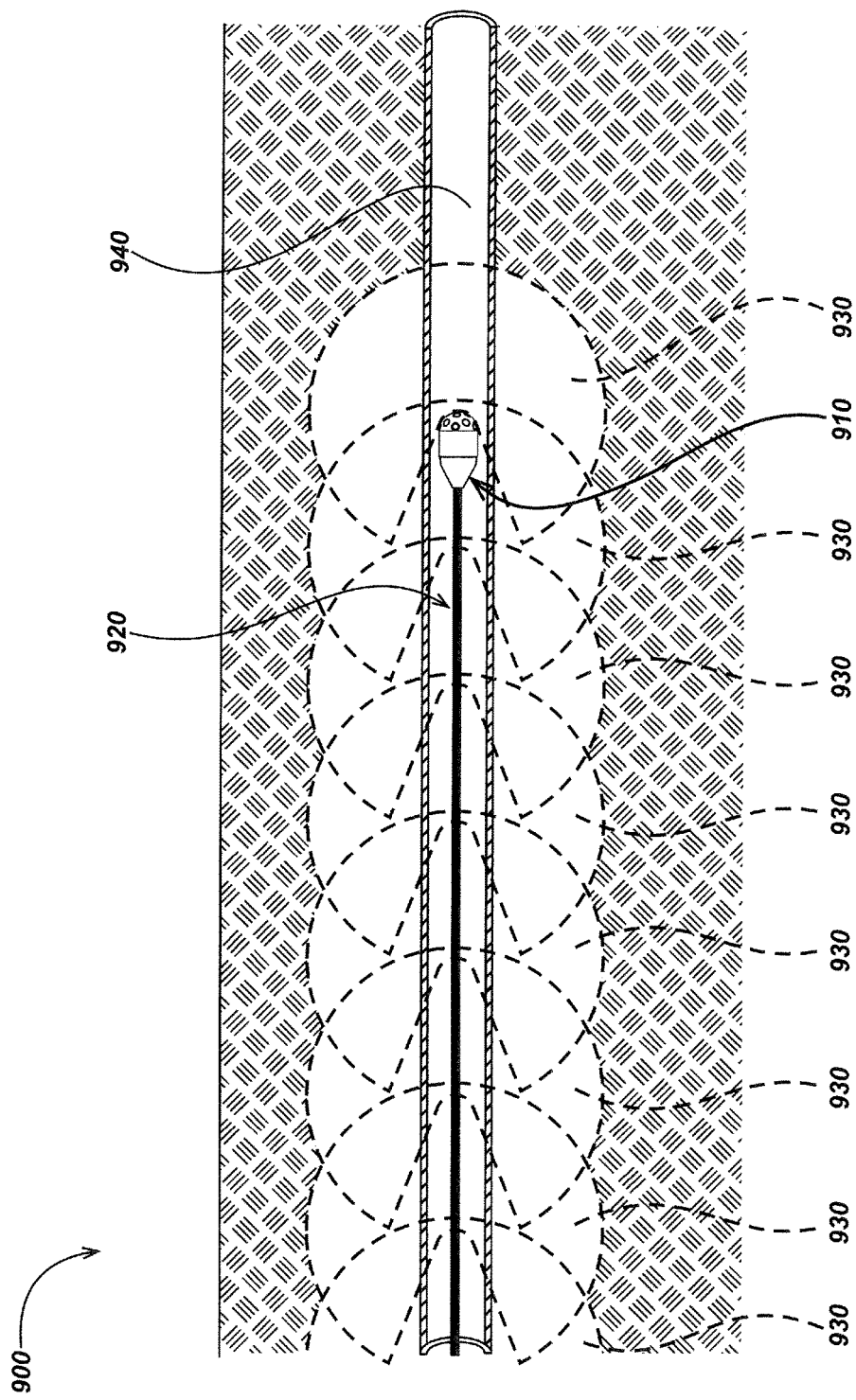
FIG. 9 is an illustration of an embodiment of details of a method for creating pipe mapping information using successive high resolution images.

In some pipe inspection system embodiments, the imagery collected may include a series of successive photo sphere images, such as with the enhanced resolution images of FIG. 7A captured at times 730 and/or the enhanced resolution images of FIG. 8A captured at times 830. As illustrated in FIG. 9, an inspection system 900 may include a camera head 910 disposed upon a distal end of push-cable 920. The camera head 910 may be configured to generate successive enhanced resolution images at sequential times/positions 930 within the inspection area. These enhanced resolution images may be captured similarly to the enhanced resolution images produced by method 700 of FIG. 7A at times 730 and/or the enhanced resolution images produced via method 800 of FIG. 8A at times 830.

The enhanced resolution images 930 may each be a composite image based on multiple images from multiple imaging modules within the camera head 910 that are tiled, stitched or otherwise combined. Such composite images may be generated using digital tiling and/or image stitching techniques implemented in real time within the camera head 910, or remotely in other system devices and/or may be done in post-processing based on images stored in a memory of the camera head or coupled device or system, such as a memory card. The enhanced resolution images 930 may further be used as input images for implementing digitally simulated articulation at a display element such as the camera control unit 1050 illustrated in FIG. 10 and/or the utility locator device 1060 also illustrated in FIG. 10 and/or other configured display devices. Details of apparatus and methods for implementing digital tiling, image stitching and digitally simulated articulation within a pipe inspection camera and system as may be combined in embodiments with the disclosures herein may be found in co-assigned U.S. patent application Ser. No. 13/913,485, filed Jun. 9, 2013, entitled Multi-Camera Pipe Inspection Apparatus, Systems, and Methods and U.S. patent application Ser. No. 14/207,089, filed Mar. 12, 2014, entitled Multi-Camera Pipe Inspection Apparatus, Systems, and Methods. The content of each of these applications are incorporated by reference herein in their entirety. Enhanced resolution images 930 may be generated by an imaging module arrangement wherein the images overlap one another so as to provide a continuous representation of the inspection area. In areas of image overlap, 3D stereo processing of images may be done to generate 3D images of the areas being viewed within the pipe or other inspection area using overlapping fields of view, such as the overlapping fields of view as illustrated in FIG. 3B.

Figure 10:
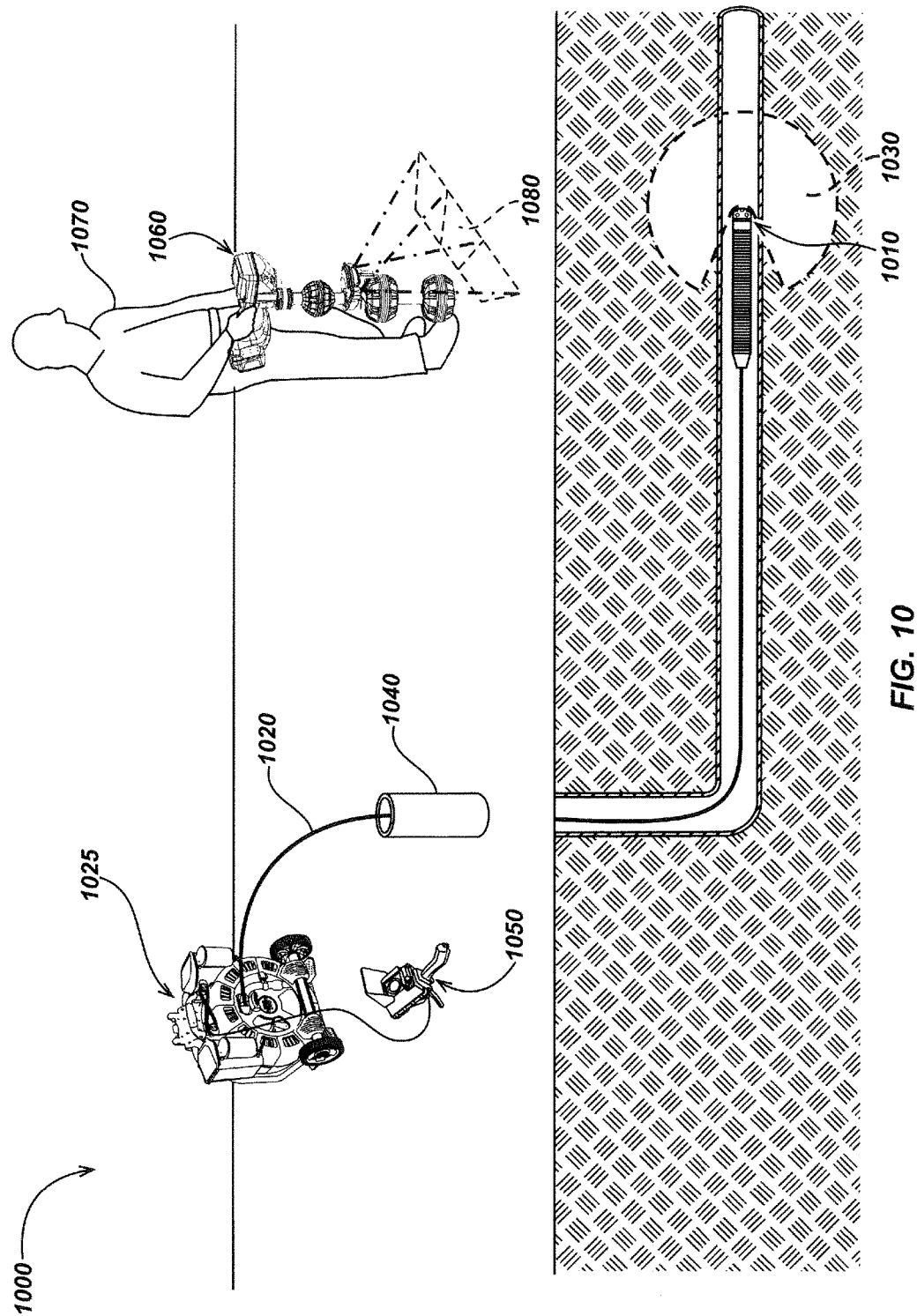
FIG. 10 is an illustration of a pipe inspection system embodiment that includes a utility locator device in conjunction with an inspection camera system.

FIG. 10 illustrates details of an embodiment 1000 of an inspection system including a camera head, buried utility locator and associated components. As illustrated in FIG. 10, inspection system embodiment 1000 may include a camera head 1010 disposed upon the end of a push-cable 1020 and dispensed from a cable reel 1025. A utility locator 1060 may be used by an operator 1070 on the ground surface above the camera head 1010. The camera head 1010 may be configured to generate successive enhanced resolution images 1030 (e.g., composite images, etc.) of the inspection area such as within pipe 1040, for example as described with respect to FIG. 9. Additional images may be captured by the utility locator 1060 along with additional locator data or information.

The enhanced resolution images 1030 and/or other inspection and utility locater images and data may be communicated to and displayed upon various display devices. For example, the pipe inspection system 1000 may further include a camera control unit 1050 connected to reel 1025, push-cable 1020 and camera head 1010, with the CCU configured to display enhanced resolution images 1030 and/or other inspection and utility locating images and data, such as images or data provided from locator 1060. The CCU 1050 may also control operation of some of the devices included in the pipe inspection system 1000. Enhanced resolution images 1030 and/or other inspection and utility locating images and data may also be communicated to and displayed upon utility locator device 1060. Such imagery and/or data may be communicated to utility locator device 1060 via a wireless connection or, in some embodiments, via a wired connection between camera head 1010, CCU 1050 and/or locator 1060 using wired or wireless communication modules.

The utility locator device 1060 carried by a user 1070 may generate images and/or video of the ground surface, such as the ground surface imagery 1080. Utility locator device 1060 may include a GPS or other location or positioning system module to determine its exact location (e.g., relative to coordinates such as latitude/longitude) and/or relative position (e.g., with respect to local surface features, the camera head 1010, CCU 1050, and the like) and generate data corresponding to location or position. In such embodiments, each individual enhanced resolution image 1030 and the location thereof may be associated with a known instance of the ground surface imagery 1080 generated by the utility locator device 1060 and may be stored in a memory or database.

For example, a camera head such as camera head 1010 may be configured with inertial navigation system (INS) sensors, compass sensors, gyroscopic sensors, visual odometry/motion tracking sensors and algorithms, and/or other position or orientation sensors and corresponding processing algorithms to determine movements/relative location within the inspection area while under the ground in the pipe or other cavity. As the camera head 1010 is moved through the inspection area, the relative location of each enhanced resolution image 1030 may be determined within the inspection area within the pipe or other such conduit based in sensor information in or coupled to the camera head 1010. The utility locator device 1060 may include a global positioning system (GPS) receiver or other satellite system receivers such as GLONASS or Galileo system receivers, inertial navigation system (INS) sensors, gyroscopic sensors, visual odometry or motion tracking sensors and algorithms, and/or other position sensors and processing algorithms to determine the location of each instance of ground surface imagery 1080 to be known relative to the inspection at the ground surface and/or the specific geographic location on the Earth.

Figure 11:
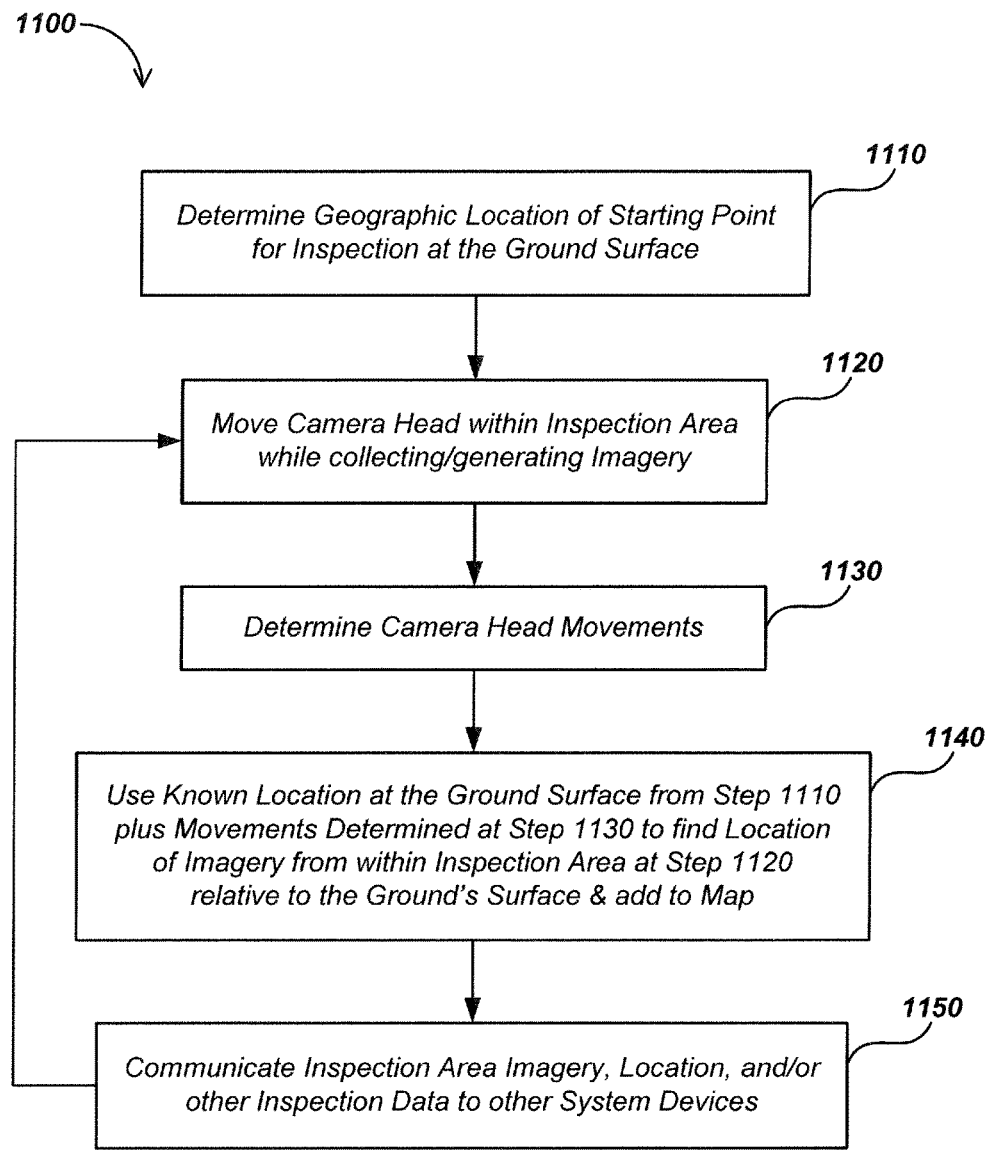
FIG. 11 is an illustration of details of an embodiment of a method for determining the location of pipe inspection imagery relative to the ground surface, in accordance with certain aspects.

Turning to FIG. 11, details of an embodiment of a method 1100 for determining the location of imagery gathered by a camera head within a pipe, conduit or other subterranean location relative to the ground surface are illustrated. At stage 1110, the start location of the camera head relative to the ground surface is determined. For example, GPS or other location position sensors within a cable reel, such as the reel 1025 of FIG. 10, may generate data to determine location as the push-cable 1020 is dispensed into pipe 1040, and/or the images and position of the start location of the pipe inspection may be gathered by a utility locator device or other inspection system device. In some embodiments, positioning data gathered from other system devices such as GPS data from a smart phone and/or input from a user may be used. At stage 1120, the camera head may be moved within the pipe or cavity while generating imagery of the inspection area. Such imagery may include video and/or still images such as the enhanced resolution images described with respect to FIG. 10, which may be a composite image or video and/or HDR or other enhanced imagery.

At stage 1130, movement of the camera head may be determined using INS sensors and/or visual odometry/motion tracking analysis. At stage 1140, movements determined in stage 1130 from a known ground surface starting point location or other reference location made in stage 1110 may be used to determine the location of inspection imagery generated at the camera head relative to the ground's surface. At stage 1140, the location of inspection imagery generated from the camera head relative to the ground surface may further be added to map data to generate composite map data or information, such as in the form of a marked-up digital map including imagery and/or other inspection system data. At stage 1150, inspection area imagery, locations, and/or other inspection data, including mapped locations of pipe inspection imagery at the ground surface, may be sent to various inspection system devices. For example, mapping data, imagery and/or other inspection data may be communicated wirelessly to a utility locator device, cable reel, utility locator transmitter or other electronic computing device or system. The communication of such information may be done as this information is generated/determined, allowing a utility locator device and/or other configured device to create mapping data to generate a map of the pipe or other subterranean inspection area. The method 1100 may then repeat, returning to stage 1120 and repeating until the inspection is complete. In some method embodiments, a utility locator device may be used to periodically check and/or update camera head location information during the various stages of the method. Furthermore, a utility locator device may be used to trace the movements of the camera head during an inspection, such as by receiving magnetic fields from a sonde or other magnetic field signal source coupled to or associated with the camera head.

In some method embodiments, a known starting location relative to the ground surface need not be determined or used. For example, as shown in method embodiment 1200, at stage 1210 a camera head may be moved through a pipe or cavity while generating imagery of the inspection area. Such imagery may include video and/or still images such as those described with respect to FIG. 10. At stage 1220, movement of the camera head within the pipe or other subterranean inspection area may be determined using INS sensors and/or visual odometry/motion tracking algorithms. In stage 1230, each movement(s) from stage 1220 may be stored within a database of camera head movements, imagery corresponding to such movements, sensor data and/or other inspection system data. Such a database may reside in any of the inspection system devices. This may first require communicating the data to the system device(s).

At stage 1240, a utility locator device may be used to determine the location of the camera head within the pipe or other subterranean location relative to the ground surface. For example, a sonde device on or within the camera head, or on or coupled to the push-cable a known distance from the camera head, may be used to generate magnetic fields which the utility locator device uses to determine the camera head location and/or orientation. At stage 1250, from the ground surface location determined at stage 1240, historic camera movement data stored at stage 1230 may be used to generate mapping data that includes the location of imagery from the inspection area within a pipe or other obscured location relative to the ground surface.

In similar method embodiments, following stage 1250, the method may continue by returning to stages 1210 through 1230 to add additional camera head movement onto the map data generated at stage 1250. In alternative method embodiments, stages 1210 through 1230 may be repeated until a user has completed the inspection of the pipe or other cavity. Once the inspection has been completed, the method may continue at stage 1240 through stage 1250. In such methods, a utility locator device may be used to periodically check and/or update camera head location during the various stages of the method, for example by sensing a magnetic field emitted by a sonde or other magnetic field source device that is coupled to the camera head. A utility locator device may be used to continuously or periodically track and store information about the movements of the camera head during an inspection.

Figure 12:
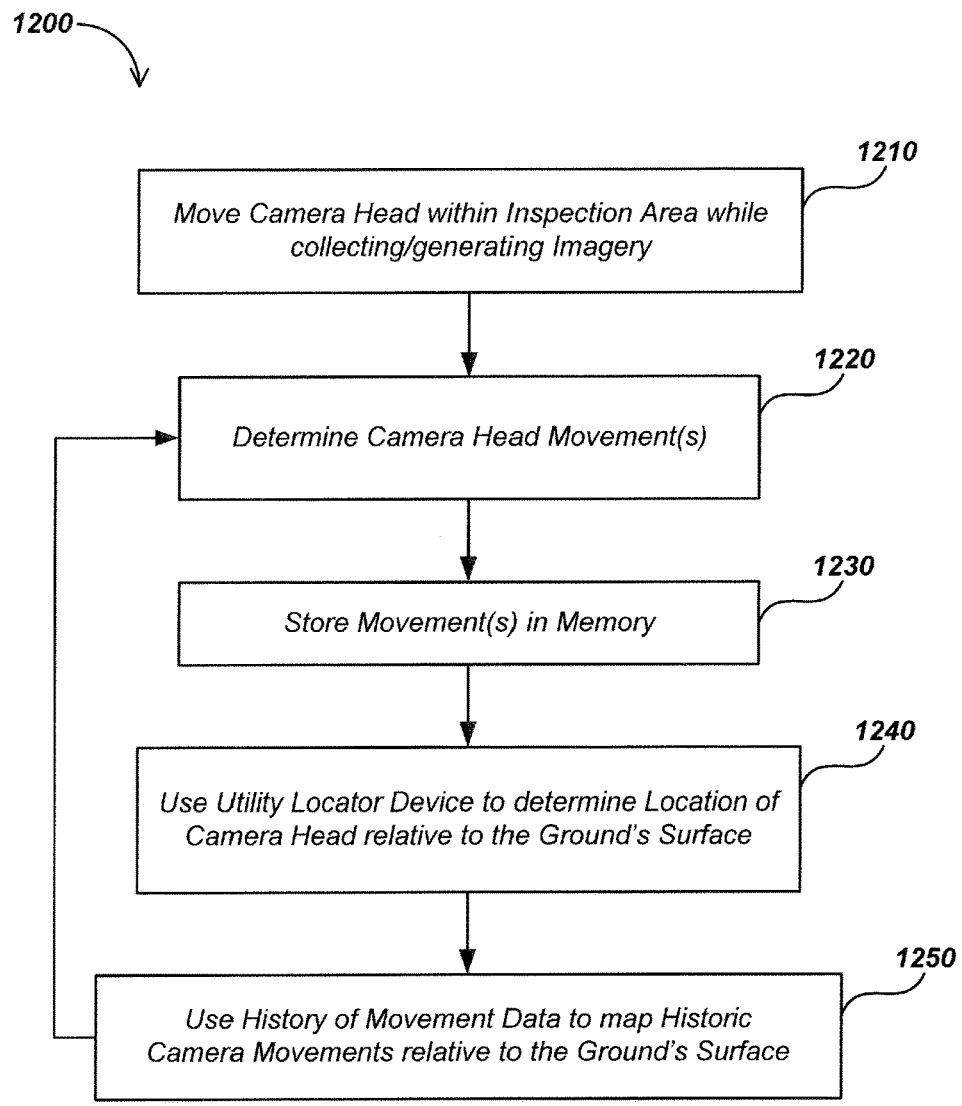
FIG. 12 is an illustration of details of another embodiment of a method for determining the location of pipe inspection imagery relative to the ground surface, in accordance with certain aspects.
Figure 13:
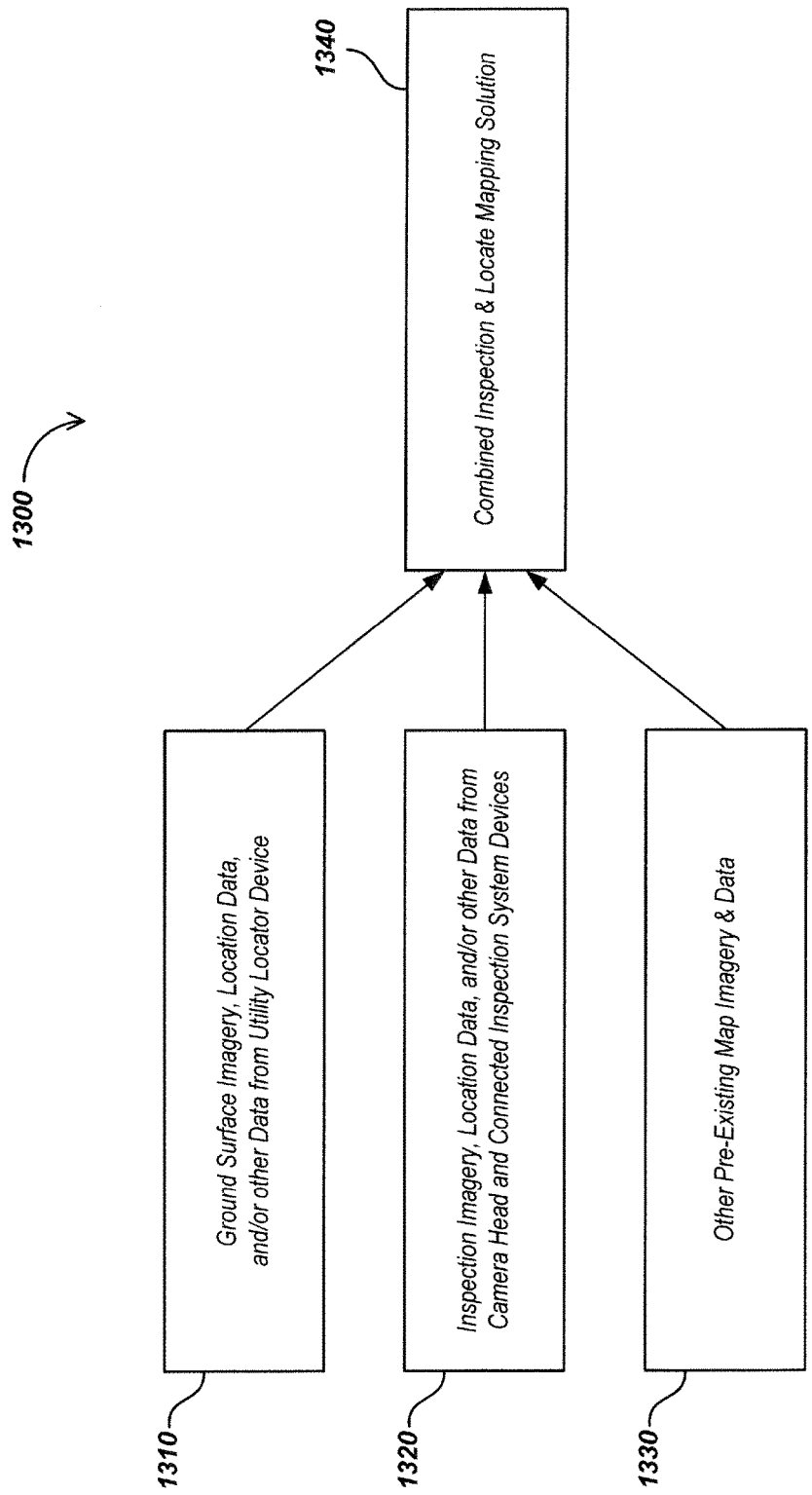
FIG. 13 is an illustration of details of an embodiment of a method for generating combined inspection and locate mapping information, in accordance with certain aspects.

Turning to FIG. 13, details of an embodiment of a method 1300 for generating maps are illustrated. Ground surface imagery, location data and/or other data from a utility locator device generated or stored in memory at block 1310 may be combined with inspection imagery, location data, and/or other inspection data from a camera head and/or other communicatively coupled inspection system devices generated or stored at block 1320, and optionally other pre-existing map data and images from block 1330, to generate combined inspection and mapping data 1340. For example, data from an aerial map of an inspection location may be associated with or combined with data from a map generated from ground surface imagery and data from a utility locator device. This may be done using various image matching or feature detection algorithms as are known or developed in the art. Ground surface imagery may further be matched with pipe inspection imagery and data utilizing, for example, method 1200 of FIG. 12 and/or method 1300 of FIG. 13. A mapping solution such as the combined inspection and locate mapping solution 1340 data may include mapping of inspection imagery and data from a camera head and other connected system devices as well as that from the utility locator.

Figure 14:
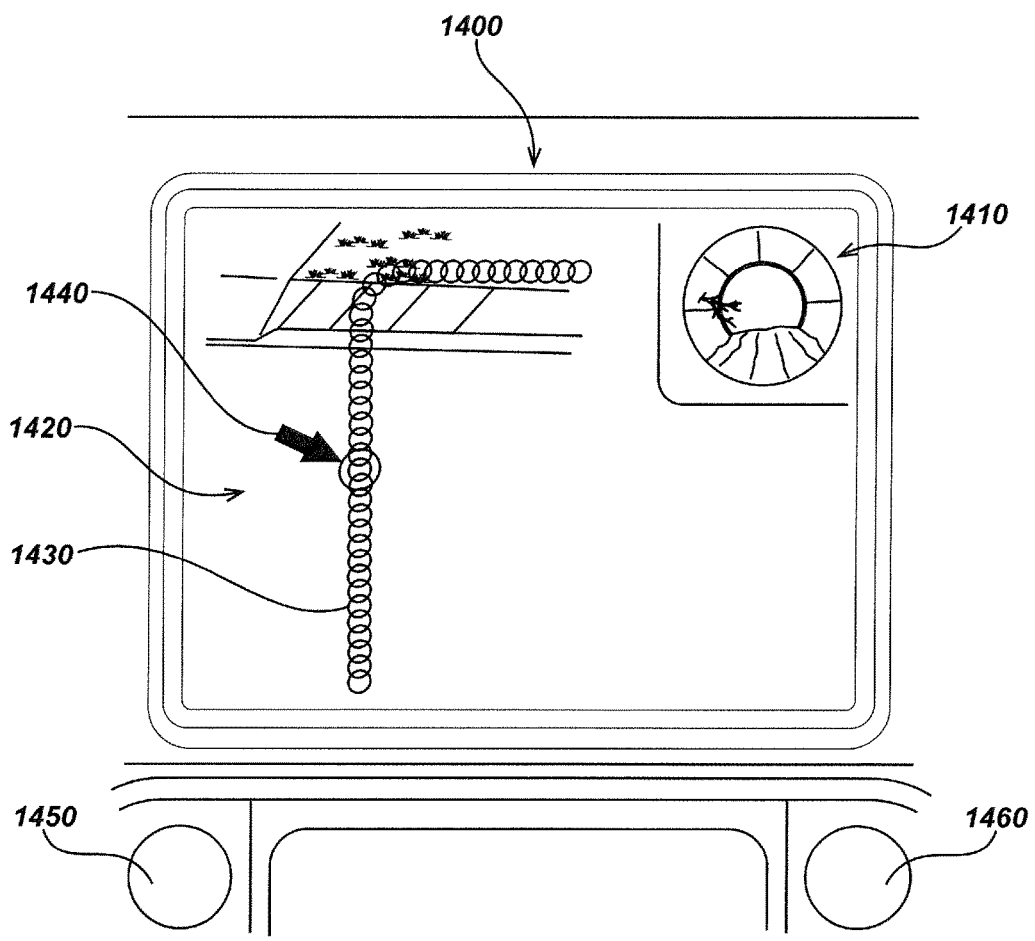
FIG. 14 is an illustration of an embodiment of a utility locator device display showing example combined inspection and locate mapping information on a visual display.

Turning to FIG. 14, details of an embodiment of a display as may be presented on a display device such as a CCU, notebook or tablet computer, utility locator, and the like is illustrated. The display may include combined inspection and locate mapping imagery based on corresponding data. For example, combined inspection and locate mapping solution data 1340 as described with respect to FIG. 13, which may include ground surface imagery, location data, and/or other data from a utility locator device as well as inspection imagery, location data, and/or other inspection data from the camera head and other connected inspection system devices, may be rendered on the display. In a utility locator embodiment as shown in FIG. 14, utility locator interface display 1400 may render pipe inspection imagery 1410, which may be rendered on or over a ground surface map 1420. The ground surface may comprise ground surface imagery collected by the utility locator device, and/or other pre-existing map imagery or imagery provided from other inspection system devices.

An inspection location line 1430 appearing on ground surface map 1420 may be generated from the correlated ground surface location to pipe inspection or other camera head inspection locations. An inspection image location indicator 1440 may designate the location of the currently displayed pipe inspection imagery 1410 relative to its ground surface location. One or more input controls such as controls 1450 and 1460 may be used to input information and/or control aspects of operation and display of the utility locator, camera heads, various pipe inspection system devices and/or the combined inspection and locate mapping solution.

In some embodiments, input control may be provided by one or more pointing or user interface devices. Some such user interface devices may have control over six or more degrees of freedom. For example, a utility locator device, camera control unit and/or other display element device may include one or more magnetically sensed user interface devices such as the user interface devices described in various co-assigned patents and patent applications including: U.S. patent application Ser. No. 12/756,068, filed Apr. 7, 2010, entitled Magnetic User Interfaces Devices; U.S. patent application Ser. No. 13/110,910, filed May 18, 2010, entitled User Interface Devices, Apparatus, and Methods; U.S. patent application Ser. No. 13/590,099, filed Aug. 20, 2011, entitled Magnetic Sensing User Interface Device Methods and Apparatus Using Electromagnets and Associated Magnetic Sensors; U.S. patent application Ser. No. 13/272,172, filed Oct. 12, 2011, entitled Magnetic Thumbstick Devices; U.S. patent application Ser. No. 13/292,038, filed Nov. 8, 2011, entitled Slim Profile Magnetic User Interface Devices; U.S. patent application Ser. No. 13/310,670, filed Dec. 2, 2011, entitled Magnetically Sensed User Interface Apparatus and Devices; U.S. patent application Ser. No. 14/281,761, filed May 19, 2014, entitled User Interface Devices; and U.S. patent application Ser. No. 14/294,068, filed Jun. 2, 2014, entitled Deformable User Interface Devices, Apparatus, and Methods. The content of each of these applications is incorporated by reference herein.

Figure 15:
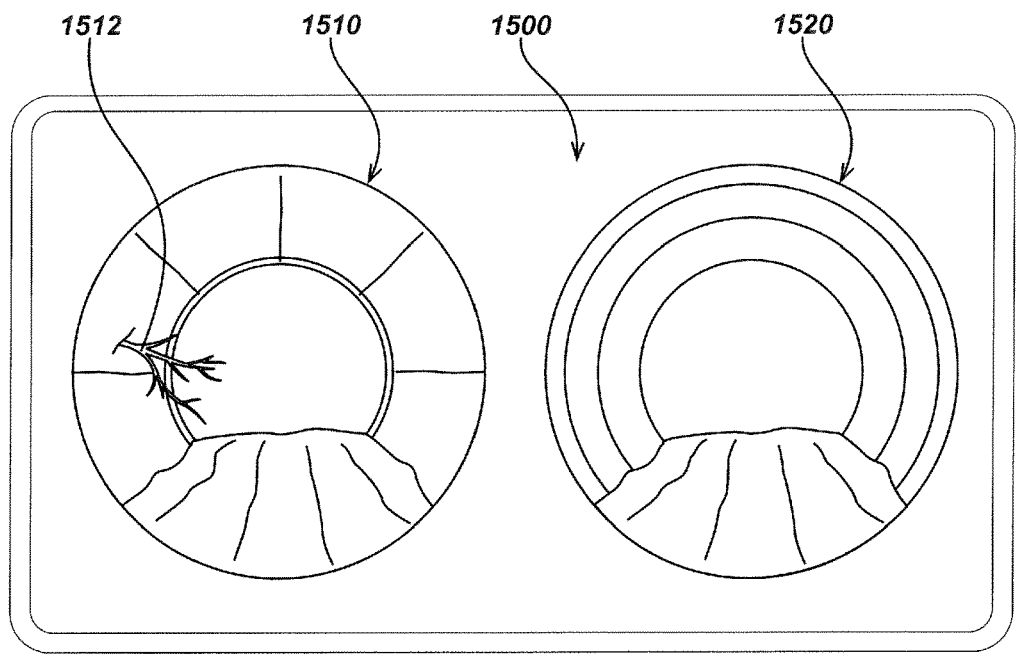
FIG. 15 is an illustration of an embodiment of a display showing both historic and current inspection imagery information for the same section and location of a pipe or other inspection area at different dates or times.
Figure 16:
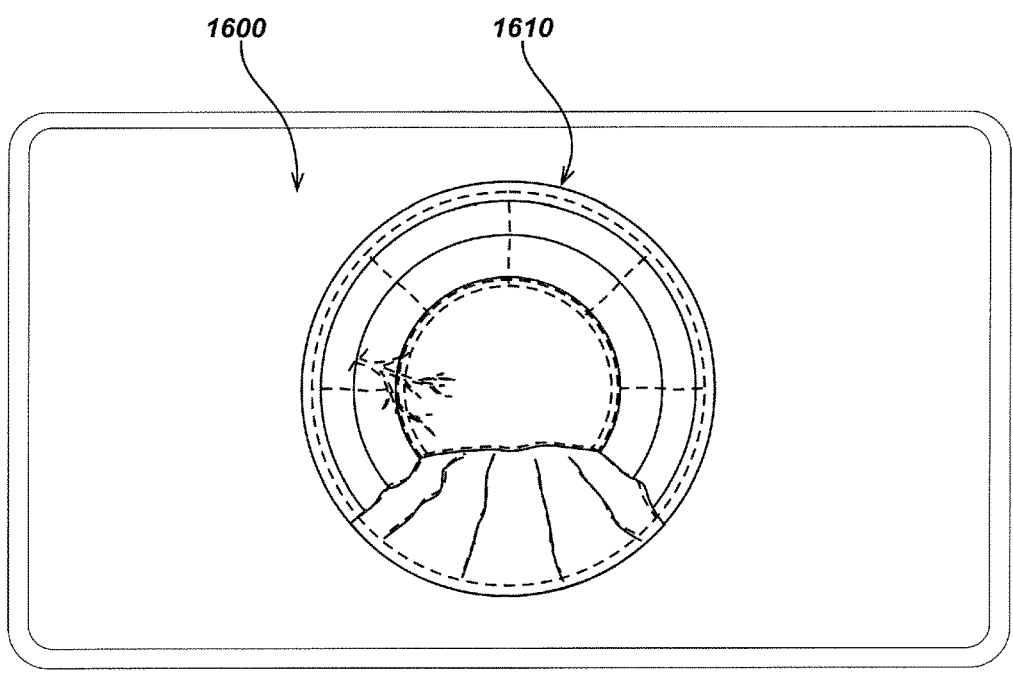
FIG. 16 is an illustration of an embodiment of an overlaid display of historic and current inspection imagery information on a visual display device.

In some display embodiments, both historical inspection images and data may be displayed with current inspection images and data. For example, in FIG. 15, display 1500 may show historic imagery 1510 of the interior of a pipe as well as current imagery 1520 of the same section and location of a pipe, taken at different times. Historic imagery 1510 may show a defect such as roots 1512, while current or later generated imagery 1520 shows that the pipe has been relined and the roots are no longer present. In such uses, historic imagery may be stored in a database, which may be a cloud database accessible by other utility locator devices and/or other locating and inspection system devices. In some display embodiments, an overlay of historic imagery over current imagery of the same section and location of a pipe taken at different times may be displayed. For example, in display 1600, overlay imagery 1610 may show both historic imagery in dotted lines as well as current imagery of the pipe in solid lines. In use other color and/or design methods may be used to represent the different imagery sets. For example, some imagery may be rendered in a particular color, shading, degree of transparency, and the like, while other imagery may be rendered in different color, shading, transparency, etc. Furthermore, the display may provide user-controlled toggling between different displays or overlays, which may include current imagery, historic imagery, and/or both historic and current imagery.

Figure 17A:
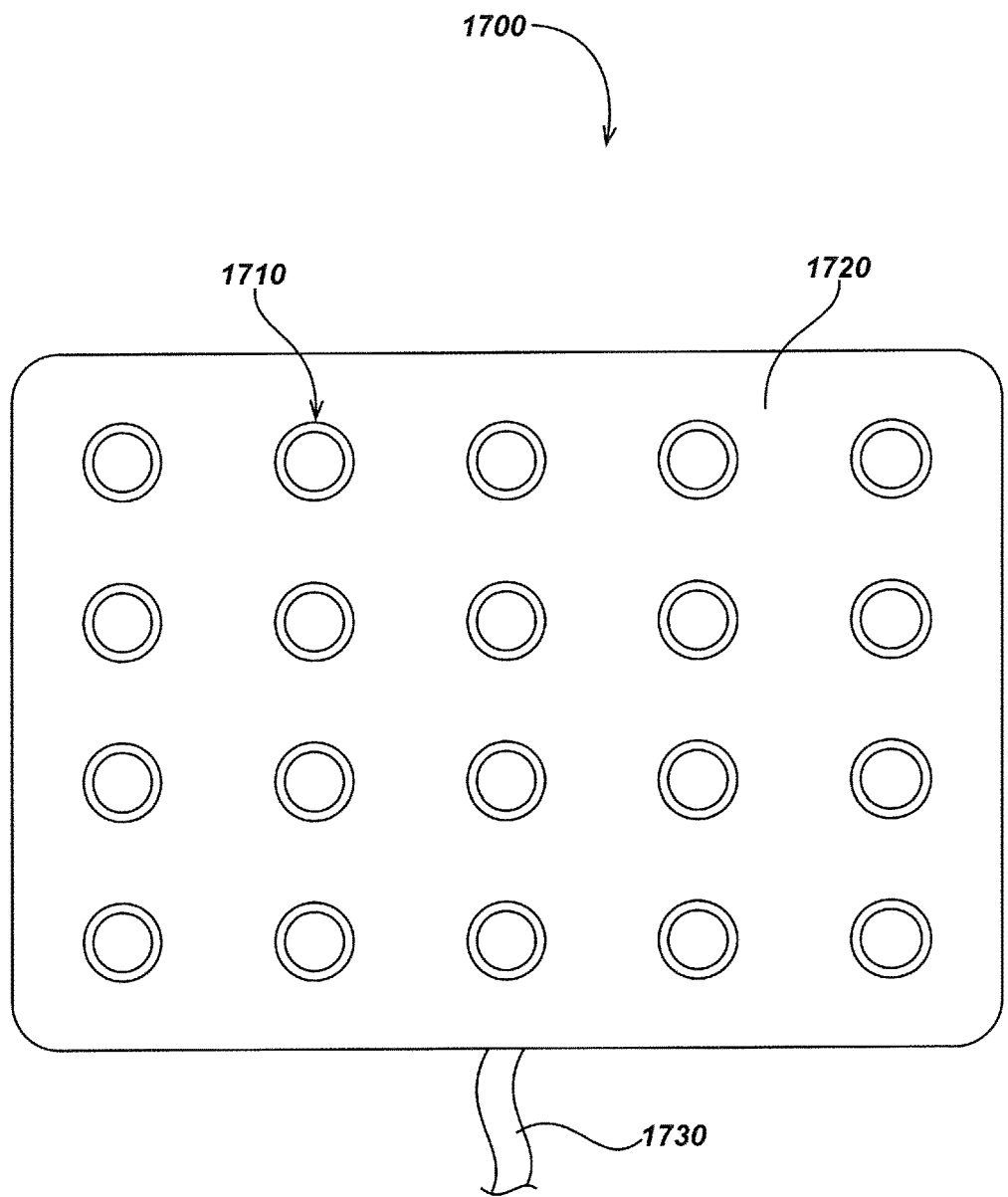
FIG. 17A is an illustration of an embodiment of a stand-alone illumination device, in accordance with certain aspects.

The various methods and devices described in the present disclosure may further be used in various other inspection devices and stand-alone illumination devices. For example, as shown in FIG. 17A, a stand-alone panel light embodiment 1700 may be comprised of one or more illumination modules 1710 seated within a single housing 1720. Wiring 1730 may be used to provide signal control and electrical power to the illumination modules 1710. Such an embodiment may be without any imaging capabilities and used for illumination purposes only.

Figure 17B:
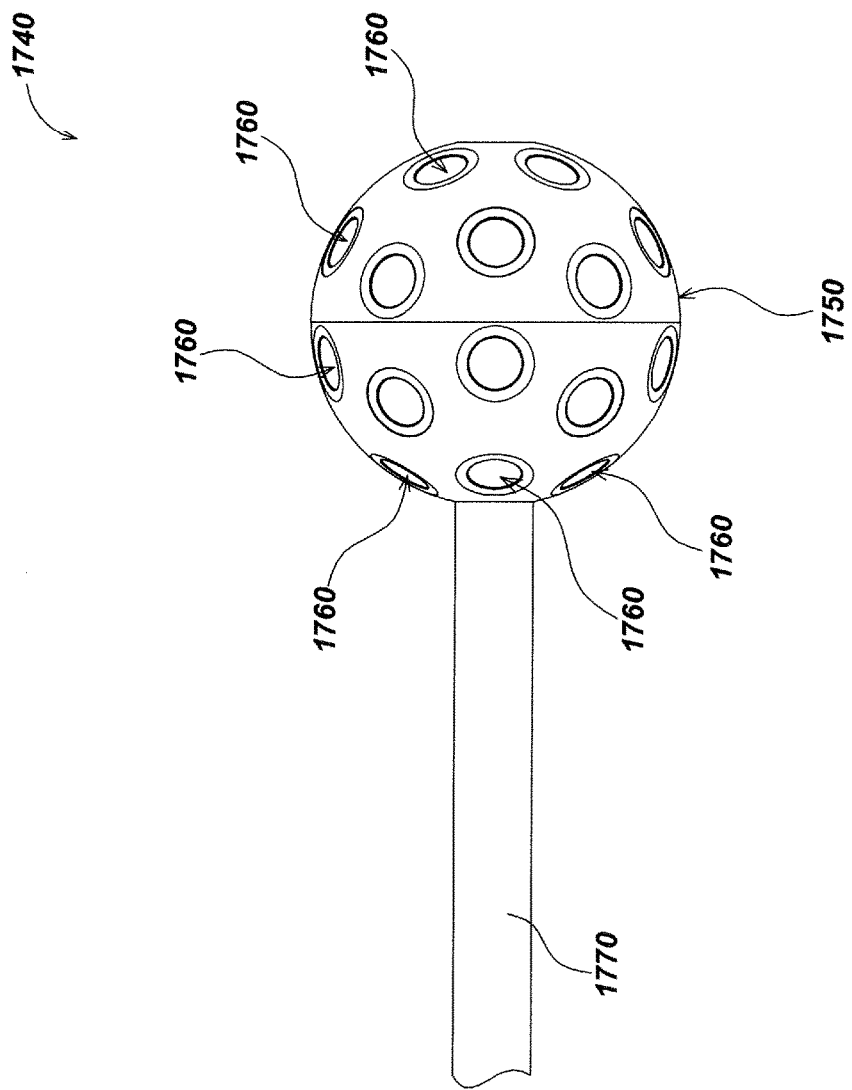
FIG. 17B is an illustration of another embodiment of a stand-alone illumination device, in accordance with certain aspects.

Turning to FIG. 17B, a stand-alone illumination device 1740 may include a spherical housing 1750 into which multiple illumination modules 1760 may be seated in a spaced-apart configuration. A mast 1770 may secure about one end of the illumination device 1740, which may further include wiring for powering and/or control the illumination device 1740, along with corresponding electronics, processing elements, and the like. The illumination modules 1760 may further include a window and/or lens(es) (not illustrated) to narrow or widen the beam of light projected. The mast 1770 may comprise thermally conductive material(s) and may further be thermally coupled to LEDs within each illumination module 1760. Another device or system combined with a stand-alone illumination device, such as the stand-alone illumination device 1740, may be further configured to steer light where it is needed or desired.

Figure 17C:
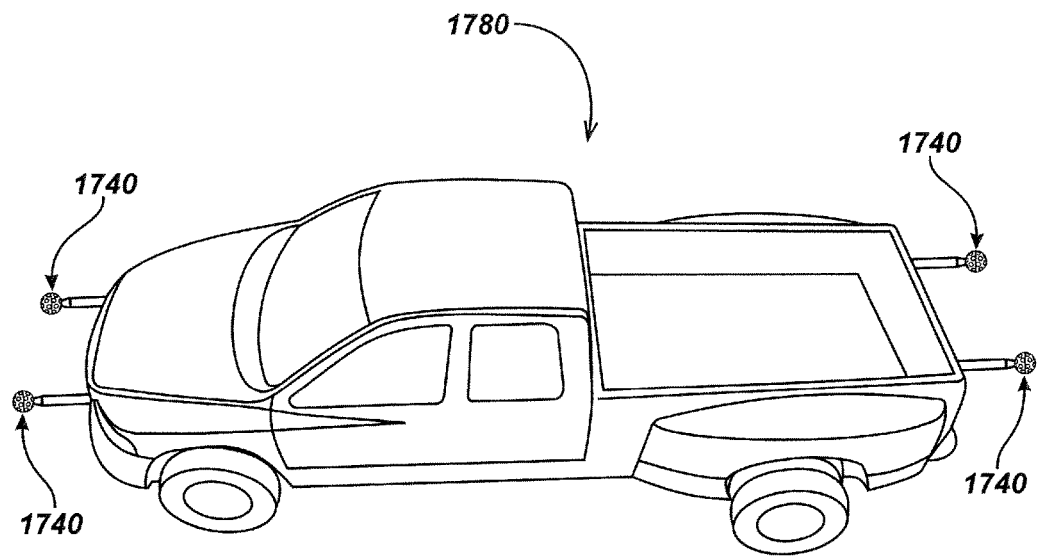
FIG. 17C is an illustration of an embodiment of a mapping vehicle including multiple stand-alone illumination devices such as those shown in FIG. 17B.
Figure 17D:
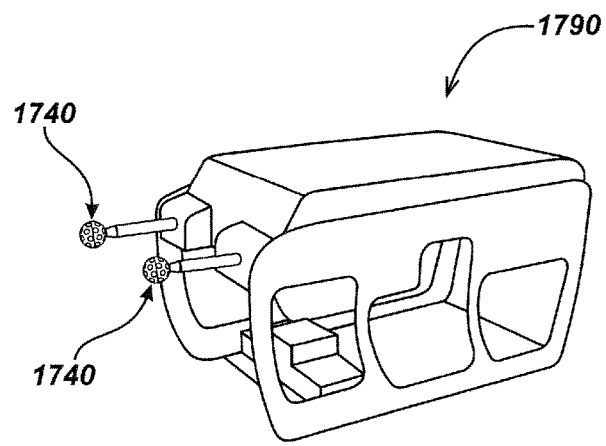
FIG. 17D is an illustration of an embodiment of a remote operated underwater vehicle (ROV) including multiple stand-alone illumination devices such as those shown in FIG. 17B.
Figure 17E:
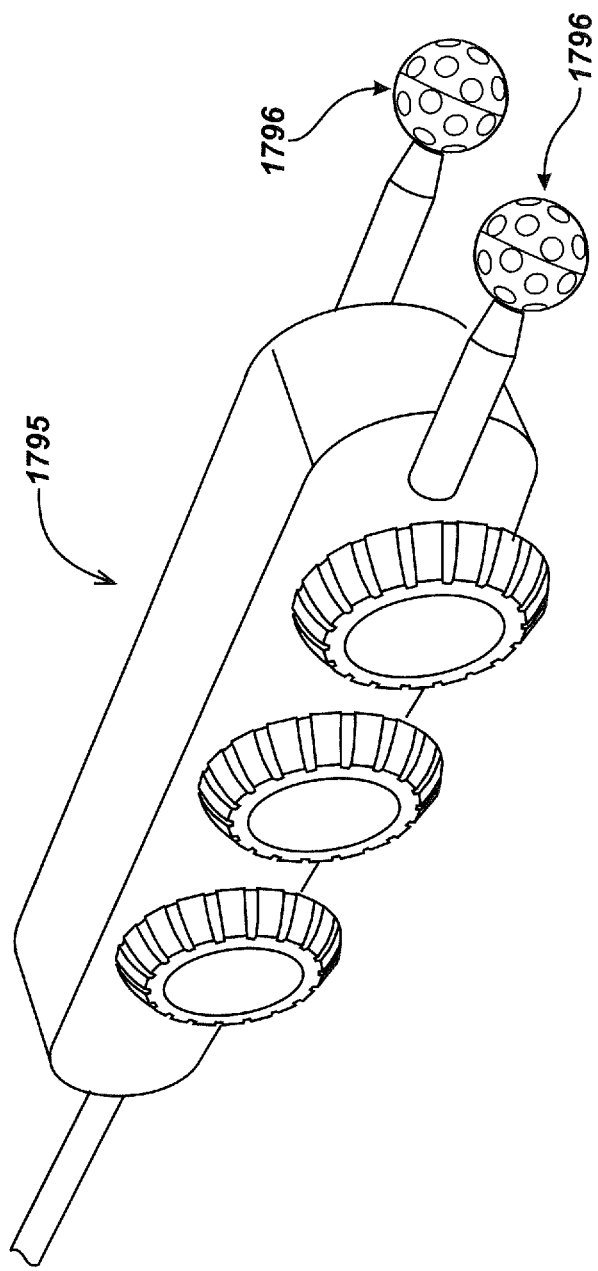
FIG. 17E is an illustration of an embodiment of a pipe-crawler device including multiple stand-along illumination devices such as those shown in FIG. 17B.

For example, one or more stand-alone illumination devices 1740 may be used in a mapping vehicle embodiment 1780 as shown in FIG. 17C or a remote operated underwater vehicle (ROV) embodiment 1790 as shown in FIG. 17D. Mapping vehicle 1780 and/or remotely operated underwater vehicle 1790 may be configured to direct light where needed and/or directed to by an operator. An illumination device such as the stand-alone illumination device 1740 may also be used in various other applications. Furthermore, in alternative ROV and/or mapping vehicle embodiments, various camera head embodiments disclosed herein may be used in lieu of or in addition to the stand-alone illumination devices 1740. For example, the pipe crawler device embodiment 1795 illustrated in FIG. 17E may include one or illumination and inspection camera heads 1796, each comprised of multiple differently oriented imaging modules as well as illumination modules.

Each illumination and inspection camera head 1796 may be the same in all or some aspects as the various camera head embodiments previously and subsequently described herein. The illumination and inspection camera heads 1796 may further be configured to capture imagery in overlapping fields of view between adjacent imaging modules on each camera head 1796, as well as in overlapping fields of view of imagery captured by each individual camera head 1796. In devices where there are two or more spaced apart camera heads, such as with the pipe crawler device 1795, a stereo baseline may be determined, allowing three dimensional imaging of the entire inspection area. Such three dimensional imaging may be used to map an inspected area in three dimensions. In some embodiments, such a device may be powered by internal batteries such as lithium polymer batteries.

Figure 18A:
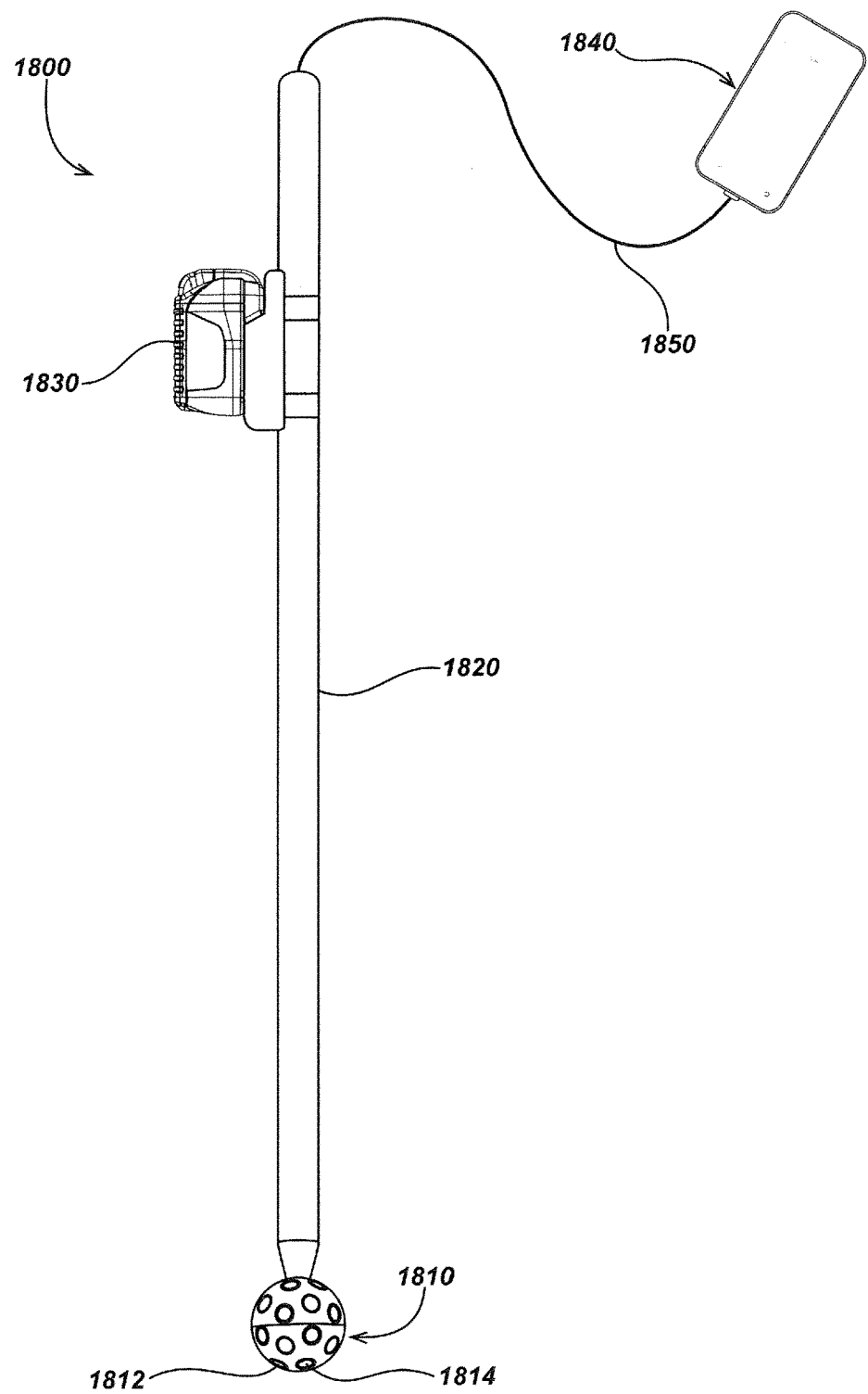
FIG. 18A is an illustration of another embodiment of an inspection device, in accordance with certain aspects.
Figure 18B:
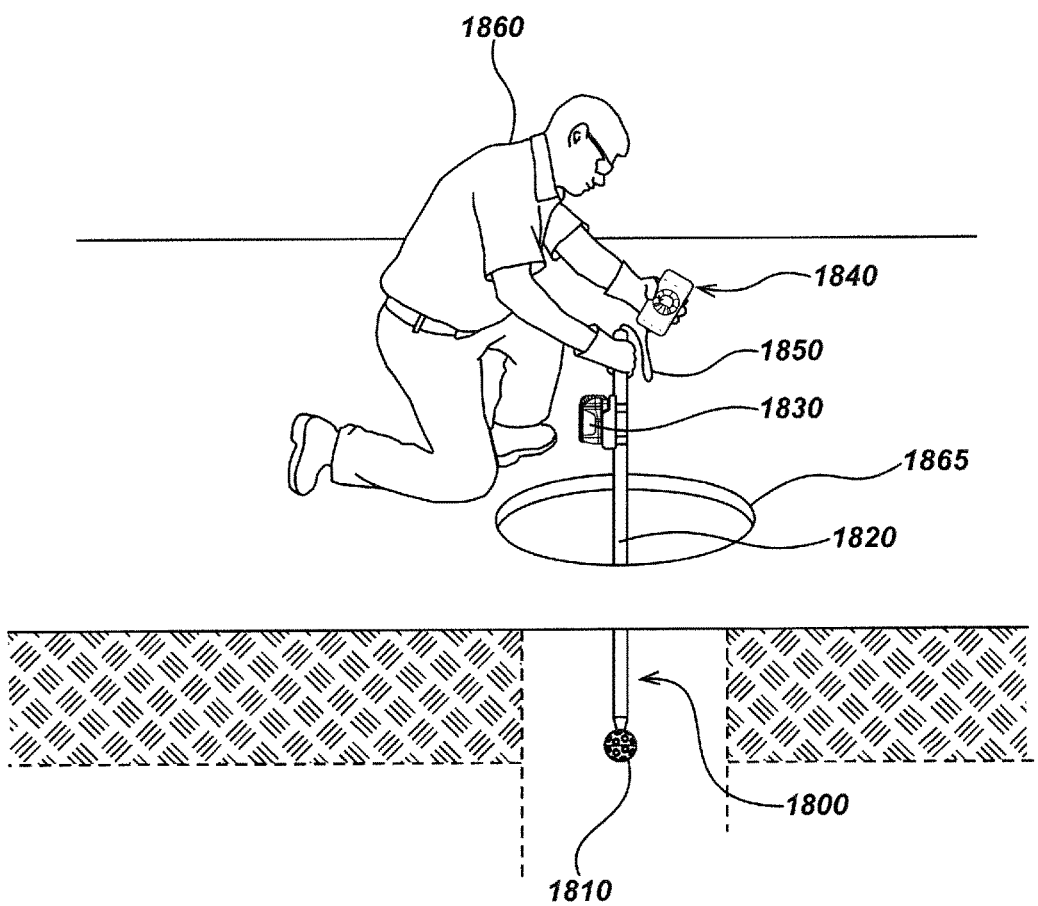
FIG. 18B is an illustration of the inspection device embodiment of FIG. 18A in use.

Other inspection devices, such as inspection device embodiment 1800 of FIGS. 18A and 18B may further utilize the methods and apparatus described in the present disclosure. For example, in inspection device embodiment 1800, a multi-imager photo sphere camera head 1810 may be coupled to one end of a mast 1820. The photo sphere camera head 1810 may be comprised of a multitude of imaging modules 1812 and illumination modules 1814. The mast 1820 may comprise thermally conductive material(s) and further be thermally coupled to LEDs within the illumination module 1814 and/or other heat producing/conducting components within the multi-imager photo sphere camera head 1810. The inspection device 1800 may be configured to capture surrounding images of an inspection area illuminated by the illumination modules 1814. A battery 1830 may secure to the mast 1820 to power the photo sphere camera head 1810. A control and display device, such as a smartphone or tablet 1840, may connect via cable 1850 and display and control images generated from the photo sphere camera head 1810, as well as control various other aspects of inspection device 1800.

As illustrated in FIG. 18B, a user 1860 may deploy the inspection device 1800 in an inspection area such as through manhole 1865. In use, inspection device 1800 may be used to inspect areas that are otherwise poorly lit and/or otherwise difficult to visually inspect and/or access.

Figure 18C:
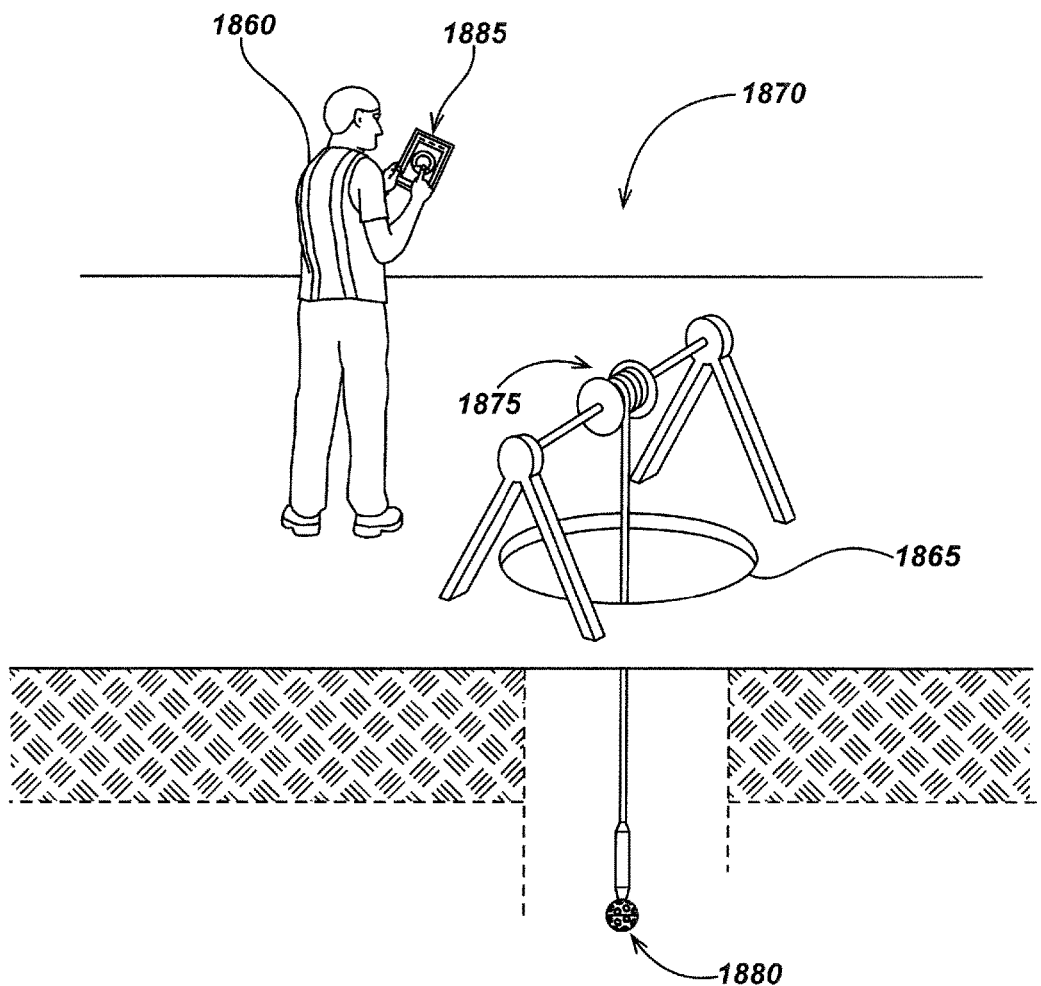
FIG. 18C is an illustration of an embodiment of an inspection device utilizing a winch.

Further embodiments, such as inspection system embodiment 1870 illustrated in FIG. 18C, may include a winch 1875 which may be controlled by a user 1860 to raise and lower a camera 1880 into an inspection area such as manhole 1865. The winch 1875 may further include a cable odometer (not illustrated) to determine the distance the device has been lowered into an inspection area. The camera 1880 may be any of the cameras and/or camera heads discussed herein. Various aspects of the winch 1875 and/or camera 1880 and/or inspection system 1870 may be configured to be controllable via a connected device (not illustrated) and/or a remotely connected device such as tablet 1885.

Figure 18D:
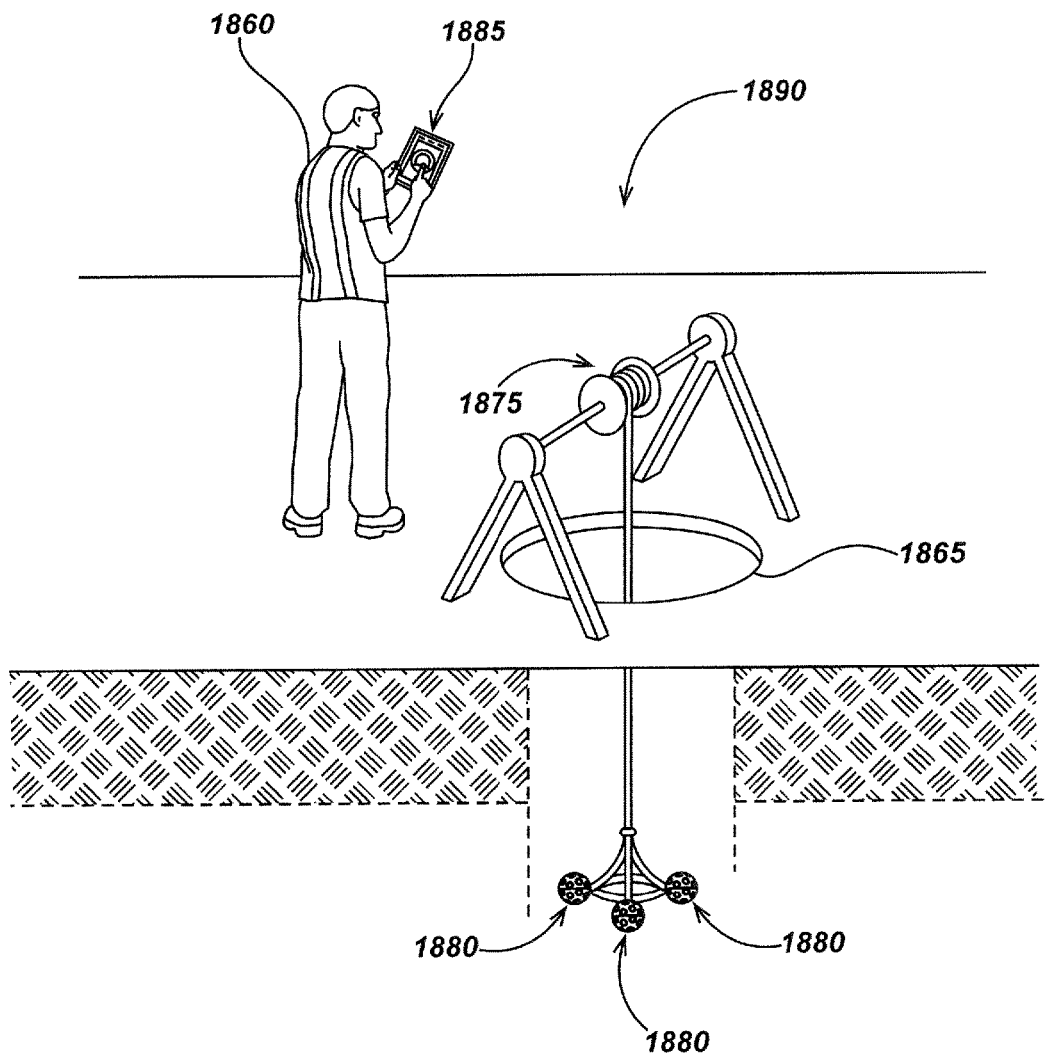
FIG. 18D is an illustration of an embodiment of an inspection device utilizing a winch with multiple spaced cameras.

Additional embodiments, such as inspection system embodiment 1890 illustrated in FIG. 18D, may include multiple cameras 1880 spaced apart from one another. The cameras 1880 may be any of the cameras and/or camera heads disclosed herein or equivalents. Similar to inspection system embodiment 1870 of FIG. 18C, inspection system 1890 may include a winch 1875 which may be controlled by a user 1860 to raise and lower the multiple cameras 1880 into an inspection area such as manhole 1865. The use of multiple spaced apart cameras 1880 may be advantageous in applications where three dimensional mapping or other three dimensional imaging is desired. Various aspects of the winch 1875 and/or cameras 1880 and/or inspection system 1890 may be configured to be controllable via a connected device (not illustrated) and/or a remotely connected device such as tablet 1885.

Figure 19A:
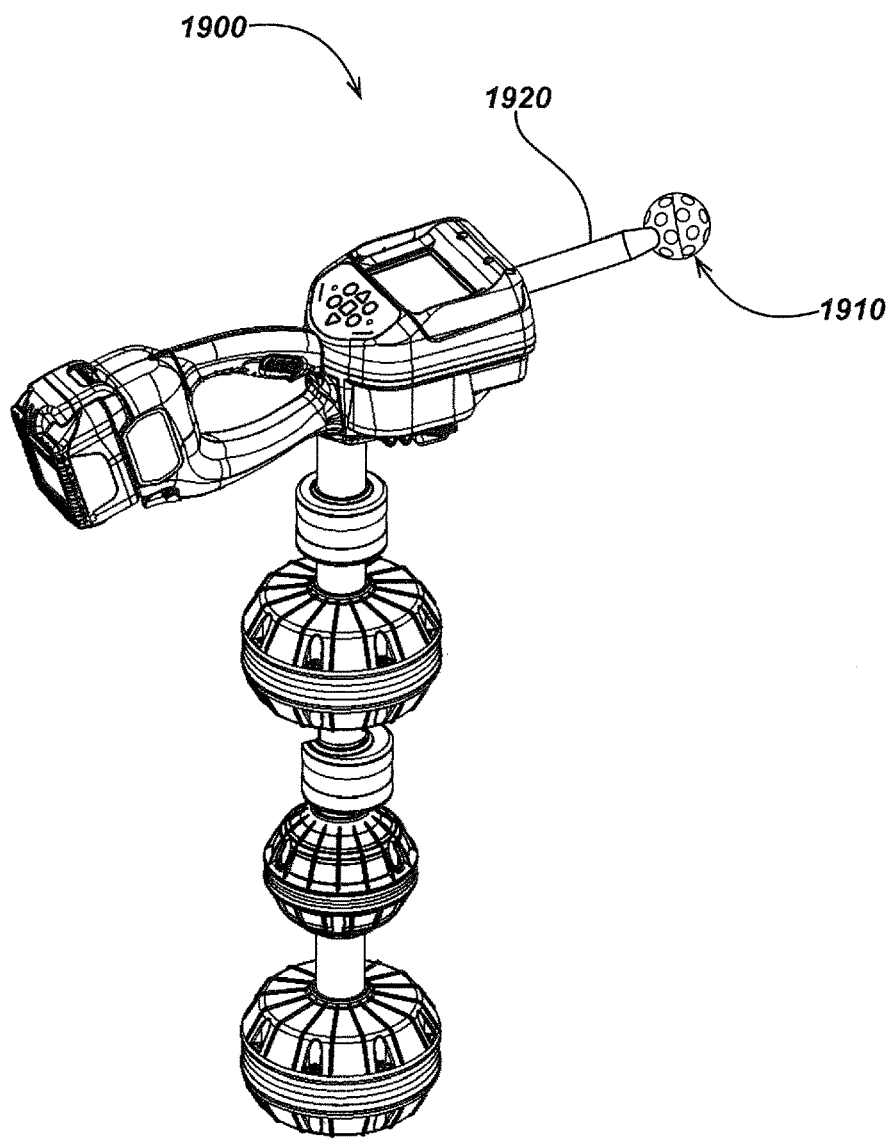
FIG. 19A is an illustration of an embodiment of an utility locating device configured with a multi-imager photo sphere camera head.

Various other devices may be configured with one or more camera heads in keeping with scope of the present disclosure. For example, in FIG. 19A, a utility locator device embodiment 1900 may include a multi-imager photo sphere camera head 1910 seated about one end of a mast 1920. The mast 1920 may further secure to a utility locator device 1900. Wiring (not illustrated) may be routed within mast 1920 to provide electrical power from utility locator device 1900 and/or communicate signals between utility locator device 1900 and multi-imager photo sphere camera head

1910. Utility locator device 1900 may control aspects of multi-imager photo sphere camera head 1910 as well as display/manipulate imagery generated therefrom on a locator display. The utility locator device 1900 may be any of the variety disclosed in the various incorporated patents and patent applications or other utility locators as are known or developed in the art. The multi-imager photo sphere camera head embodiment 1910 may be similar to the multi-imager photo sphere camera head embodiment 1810 of FIG. 18A.

Figure 19B:
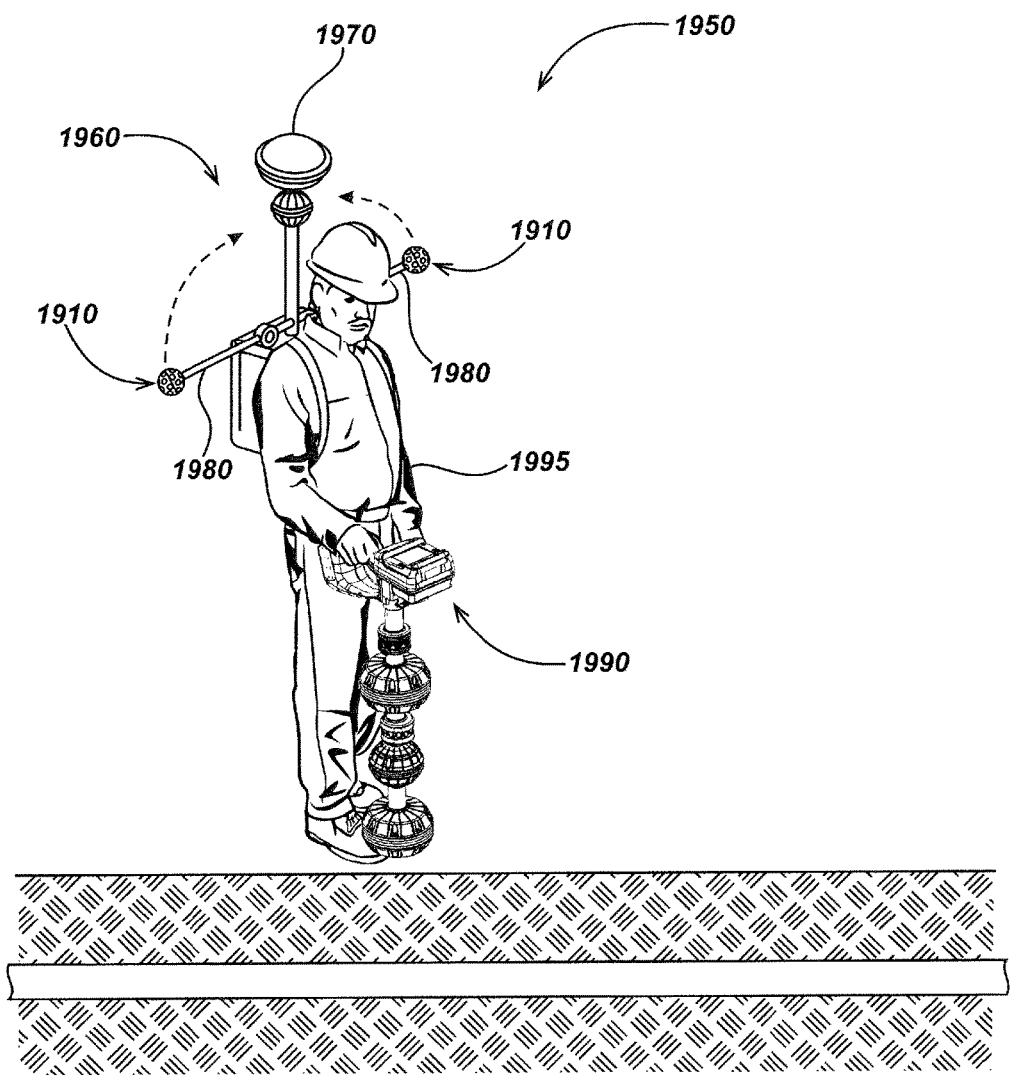
FIG. 19B is an illustration of an embodiment of a combined antenna, receiver and beacon device configured with multiple spaced apart multi-imager photo sphere camera heads as part of an inspection and locating system.

Turning to FIG. 19B, an inspection and locating system 1950 may include multiple, for example two, multi-imager photo sphere camera heads 1910 on a combined antenna, receiver and beacon device 1960. The combined antenna, receiver and beacon device 1960 may be a device/system with a dual satellite navigation antenna 1970 as described in co-assigned U.S. patent application Ser. No. 13/851,951, filed Mar. 27, 2013, entitled Dual Antenna Systems with Variable Polarization. The two multi-imager photo sphere camera heads 1910 of combined antenna, receiver and beacon device 1960 may be mounted on arms 1980 such that the multi-imager photo sphere camera heads 1910 are spaced apart from one another. Arms 1980 may further be foldable in one or more dimensions, allowing the multi-imager photo sphere camera heads 1910 to be positioned in various ways as well as readily stowable when not in use. The combined antenna, receiver and beacon device 1960 may further include communication modules to communicate data to a utility locator device 1990 carried by a user 1995 via a wired or wireless data connection. Such data may include, but may not be limited to, position information and/or image information/data generated from the multi-imager photo sphere camera heads 1910, including three dimensional mapping data and information.

Figure 20:
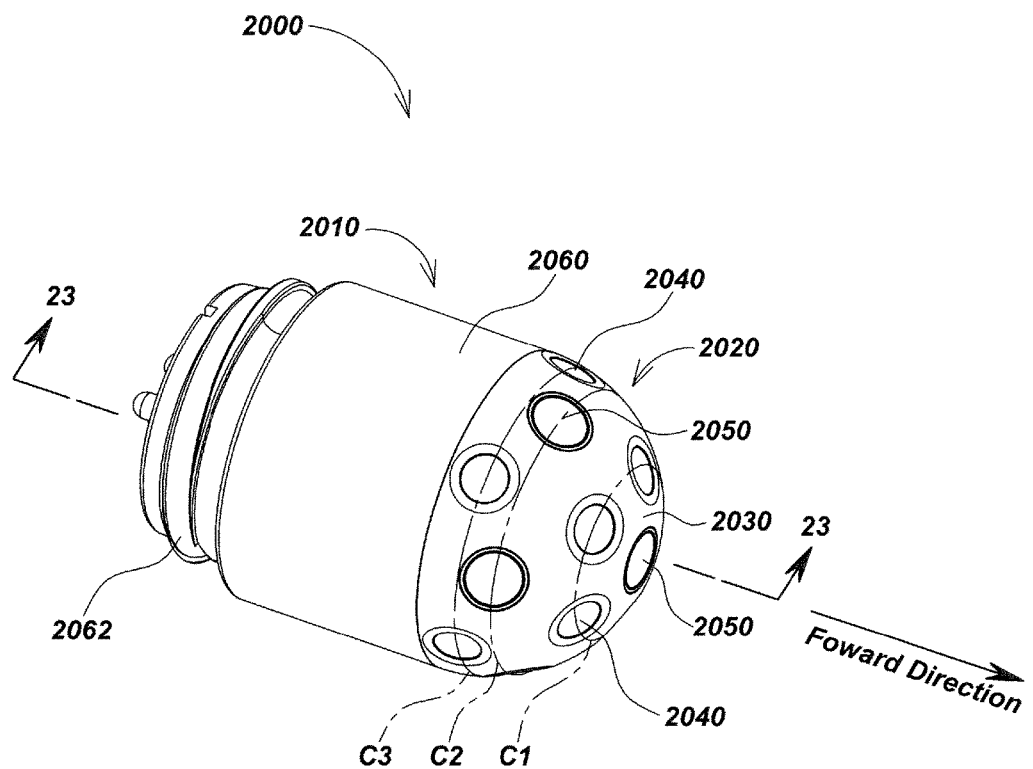
FIG. 20 is an isometric view of a camera head embodiment.

Turning to FIG. 20, details of another camera head embodiment 2000 are illustrated. As shown in FIG. 20, camera head embodiment 2000 may include a rear housing element or body 2010 and a front housing element or front 2020. The front 2020 may be comprised of a substantially hemispherical dome element 2030, with multiple illumination modules 2040 and imaging modules 2050 having windows positioned around the dome at or near the outer surface of the dome. For example, in an exemplary embodiment, front 2020 may enclose six imaging modules 2050 and ten illumination modules 2040 as shown in FIG. 20. The illumination modules 2040 and imaging modules 2050 may be positioned in the dome with LEDs, optics and imaging sensors placed near the surface of the dome element 2030 to maximize both distribution of light output and field of view of the imaging sensors.

A single forward facing imaging module 2050 may be positioned centrally on the front of dome 2030 surface as shown. A first set of five illumination modules 2040 may be positioned rearward of the forward facing imaging module 2050 on a first circumference C1 and evenly spaced along circumference C1. A set of five additional imaging modules 2050 may be positioned rearward of the first set of illumination modules evenly spaced along a second circumference, C2. Ones of the additional imaging modules 2050 may be positioned rearward of and between ones of the first set of illumination modules 2040. Further, a second set of five illumination modules 2040 may be positioned rearward of the set of additional imaging modules 2050 along a third circumference, C3. Ones of the second set of five illumination modules may be positioned rearward of and between ones of the additional imaging modules. Additional elements may be contained within the dome 230 within the front 2010 of the camera head including electronics and structural support elements (not shown in FIG. 20) for the illumination and imaging modules. This arrangement of dome, imaging modules, illumination modules and internal elements forms an illumination and imaging array in the front of the camera head for illuminating a large inspection area in a substantially even fashion and correspondingly imaging the inspection area over a wide field of view by stitching or tiling images or video from the multiple imaging modules to generate composite images or video streams.

The rear housing element 2010 may comprise a rear outer element 2060 that may be fully or partially cylindrical in shape and may be formed with or be coupled to a rear threaded feature 2062 along a rearward-facing end. In use, the rear threaded feature 2062 may secure the camera head 2000 via screw-on and screw-off threading to a push-cable, such as the push-cable 120 of FIG. 1 or to other push-cables or systems as described in the incorporated applications or known or developed in the art. For example, a push-cable may include a matching threaded feature shaped to mate with the rear threaded feature 2062 of rear outer element 2060, thereby securing the camera head 2000 to a push-cable. In some such embodiments, an O-ring (not shown) and/or a gasket or other sealing element (not illustrated) may be used between the camera head and push-cable to prevent ingress of water, dusk or other potentially harmful materials into the camera head 2000.

Figure 21:
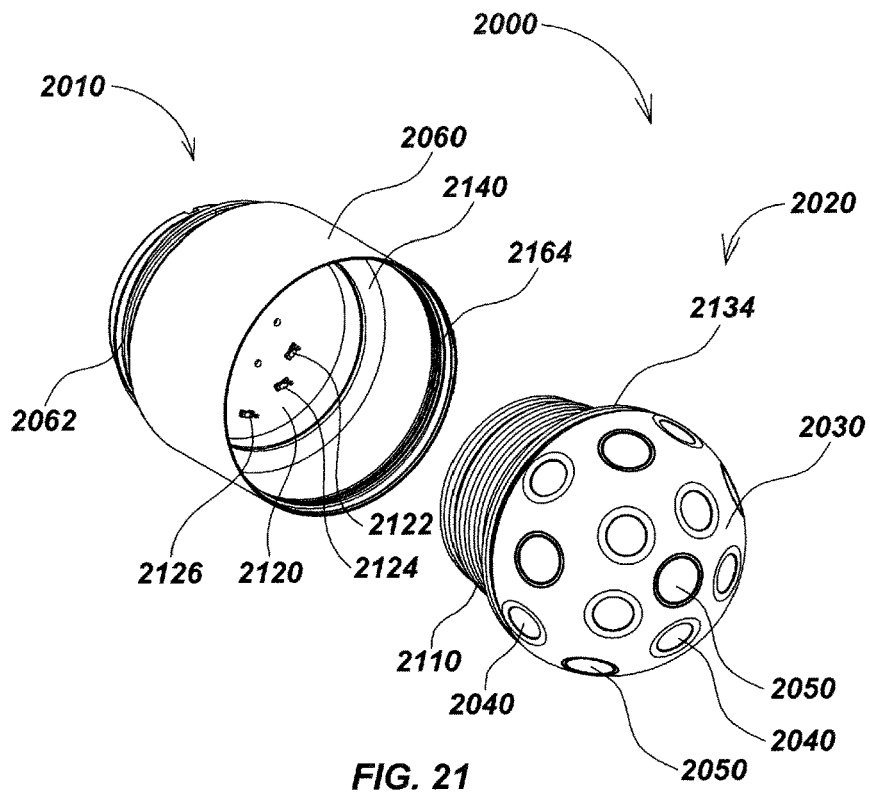
FIG. 21 is a front to back partially exploded view of the camera head embodiment of FIG. 20.
Figure 22:
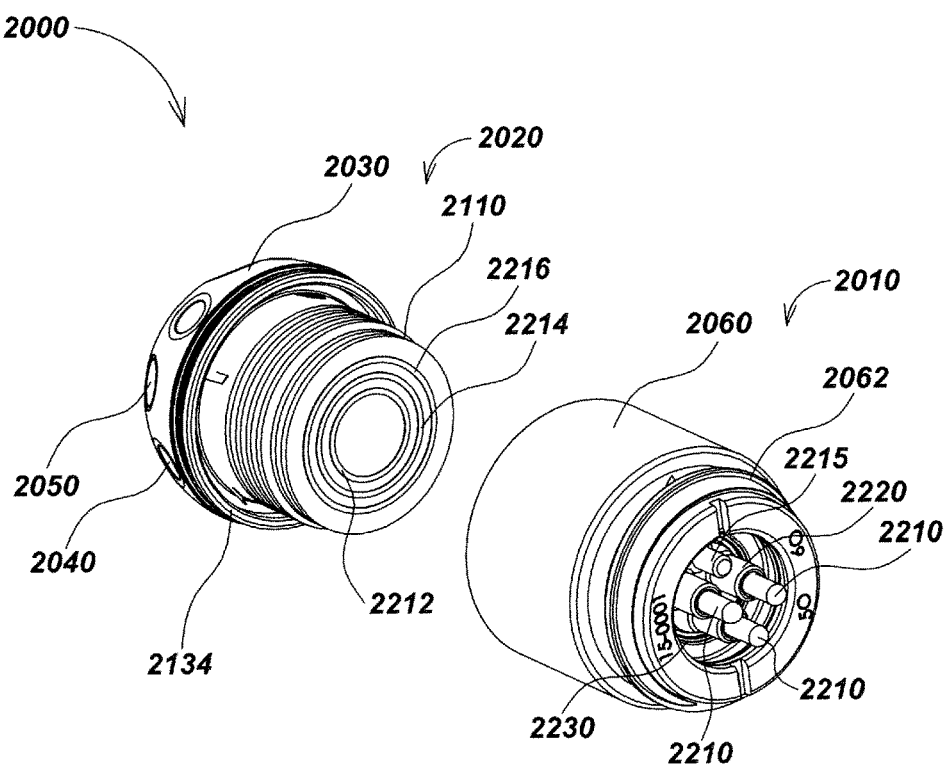
FIG. 22 is a back to front partially exploded view of the camera head embodiment of FIG. 20.

Turning to FIGS. 21 and 22, additional details of camera head embodiment 2000 are illustrated. The rear housing element 2010 may include a front threaded feature 2164, which may be formed along a frontmost inner lip of the rear outer element 2060. The front threaded feature 2164 may include threading to couple with a front camera housing threaded feature 2134 formed along a rearward-facing base circumference of the dome 2030 so as to secure together the dome 2030 and rear outer element 2060. In assembly, an O-ring (not illustrated) and/or other gasket (not illustrated) may be placed between the dome 2030 and rear outer element 2060 so as to provide a seal between the front housing element 2020 and the rear housing element 2010 of camera head 2000.

The front housing element 2020 may further include a printed circuit board (PCB) stack 2110 positioned behind the dome 2030. PCB stack 2110 may be dimensioned so that in assembly the PCB stack 2110 seats within the rear outer element 2060 and makes electrical contact with electronic components within the rear housing element 2010 to communicate signals to and from the imaging elements and provide electrical power to the imaging elements and illumination elements. The PCB stack 2110 may include an FPGA and/or other processing element(s) and associated components for implementing signal processing of images or video data provided from connected imaging modules 2050, provide control signals to the imaging modules and/or illumination modules 2040, and/or send, receive, or process signals from other internal sensors or other components. The PCB stack 2110 may further be configured with connectors or other electrical coupling elements to provide lectrical power to the aforementioned modules, sensors and other components.

Referring to FIG. 22, the rear housing element 2010 may include electrical connector pins 2210 to electrically couple to a push-cable for communicating signals from as well as providing electrical power to camera head 2000. As illustrated in FIG. 22, in an exemplary embodiment there may be three connecting pins 2210. An additional biasing pin 2215 may be included to ensure that each connecting pin 2210 correctly couples to a corresponding socket (not illustrated)

on the push-cable (not illustrated). The connecting pins 2210 and biasing pin 2215 may be seated within a pin retainer piece 2220 further seated within the back of the rear outer element 2060. The pin retainer piece 2220, with connecting pins 2210 and biasing pin 2215 seated within, may be held in place within the back of the rear outer element 2060 via a retaining washer 2230.

Turning to FIG. 21, the connecting pins 2210 may electrically couple to a rear PCB 2120, which may be substantially circular in shape, seated within the rear outer element 2060. The rear PCB 2120 may be secured in place by a PCB retaining piece 2140. A forward facing side of rear PCB 2120 may include a series of flat spring electrical connectors 2122, 2124 and 2126. For example, three flat spring electrical connectors 2122-2126 may be used, each of which may be positioned along a different diameter on rear PCB 2120. The flat spring electrical connectors 2122-2126 may be positioned such that when the camera head 2000 is assembled each electrical connector 2122-2126 may make contact with one of three concentric circular contact traces 2212, 2214 and 2216 (as shown in FIG. 22) formed on the back of PCB stack 2110, regardless of the angular alignment uncertainty resulting from mating via threads 2164 and 2134.

Figure 23:
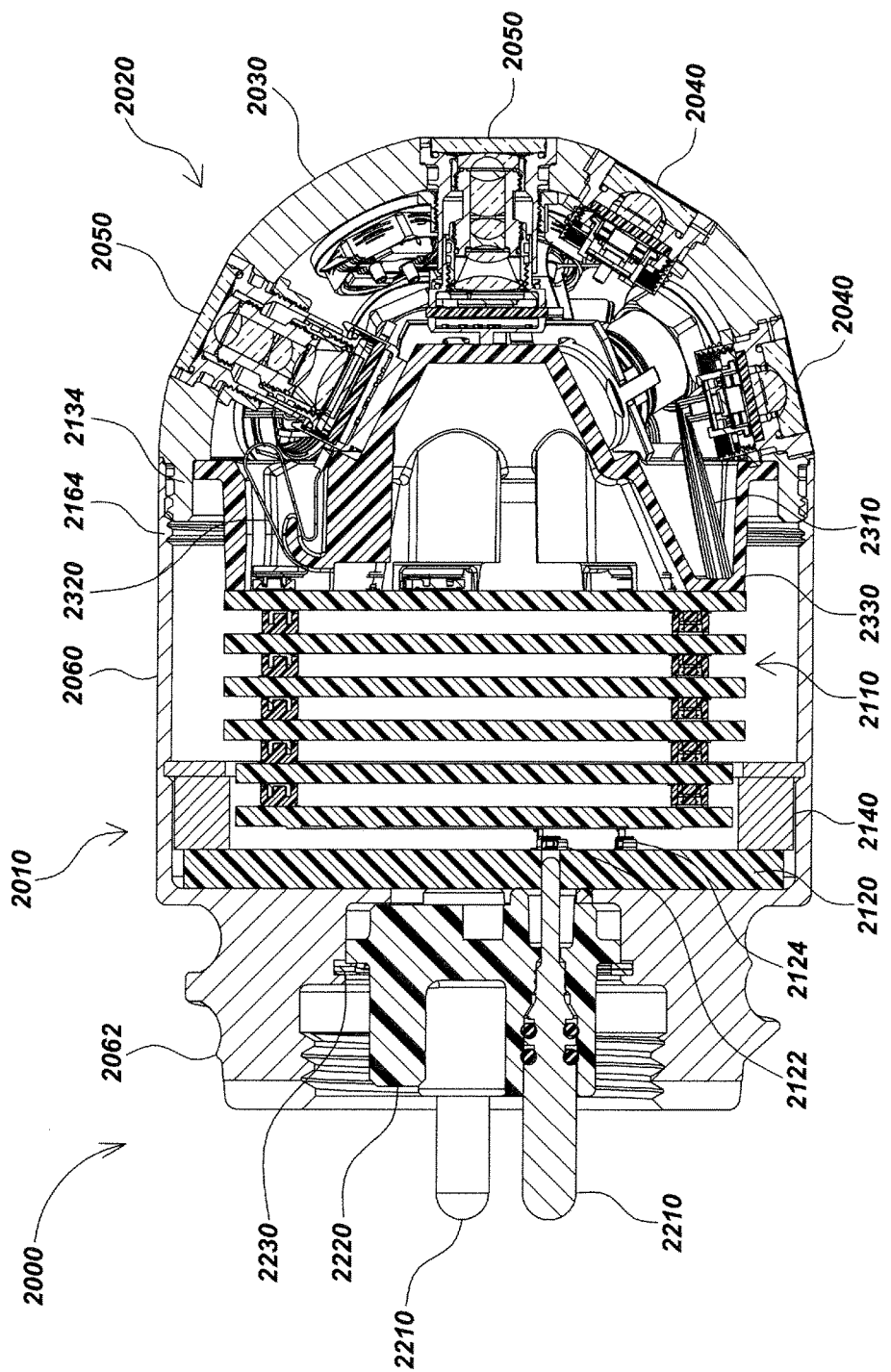
FIG. 23 is a sectional view of the camera head embodiment of FIG. 20 taken along line 23-23.
Figure 24:
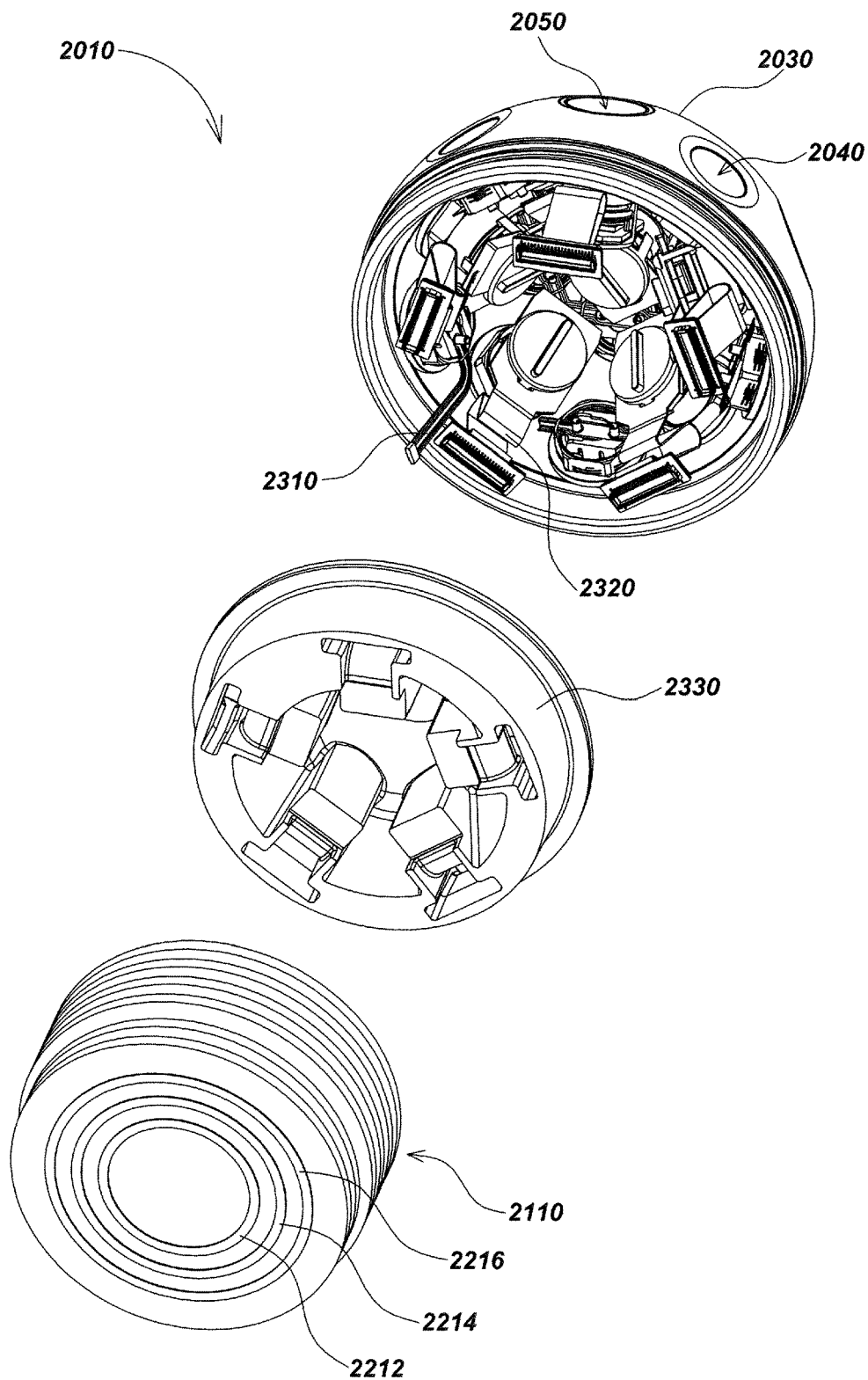
FIG. 24 is a back to front partially exploded view of an embodiment of a front camera head half.

Turning to FIGS. 23 and 24, one or more connecting wires 2310 may be used to carry control signals and/or provide electrical power from PCB stack 2110 to the various illumination modules 2040. Similarly, flex circuit 2320 and/or other wiring may be used to carry data and/or control signals and provide electrical power from PCB stack 2110 to each imaging module 2050. An approximately conical shaped wiring retainer piece 2330 (best seen in FIG. 24) may secure to the PCB stack 2110 between the PCB stack 2110 and dome 2030. For example, screws (not illustrated) may secure the PCB stack 2110 to the wire retaining piece 2330. In use, the wire retaining piece may secure each of the flex circuits 2320 and/or connecting wires 2310 in place and ensure proper connection to PCB stack 2110.

Figure 25:
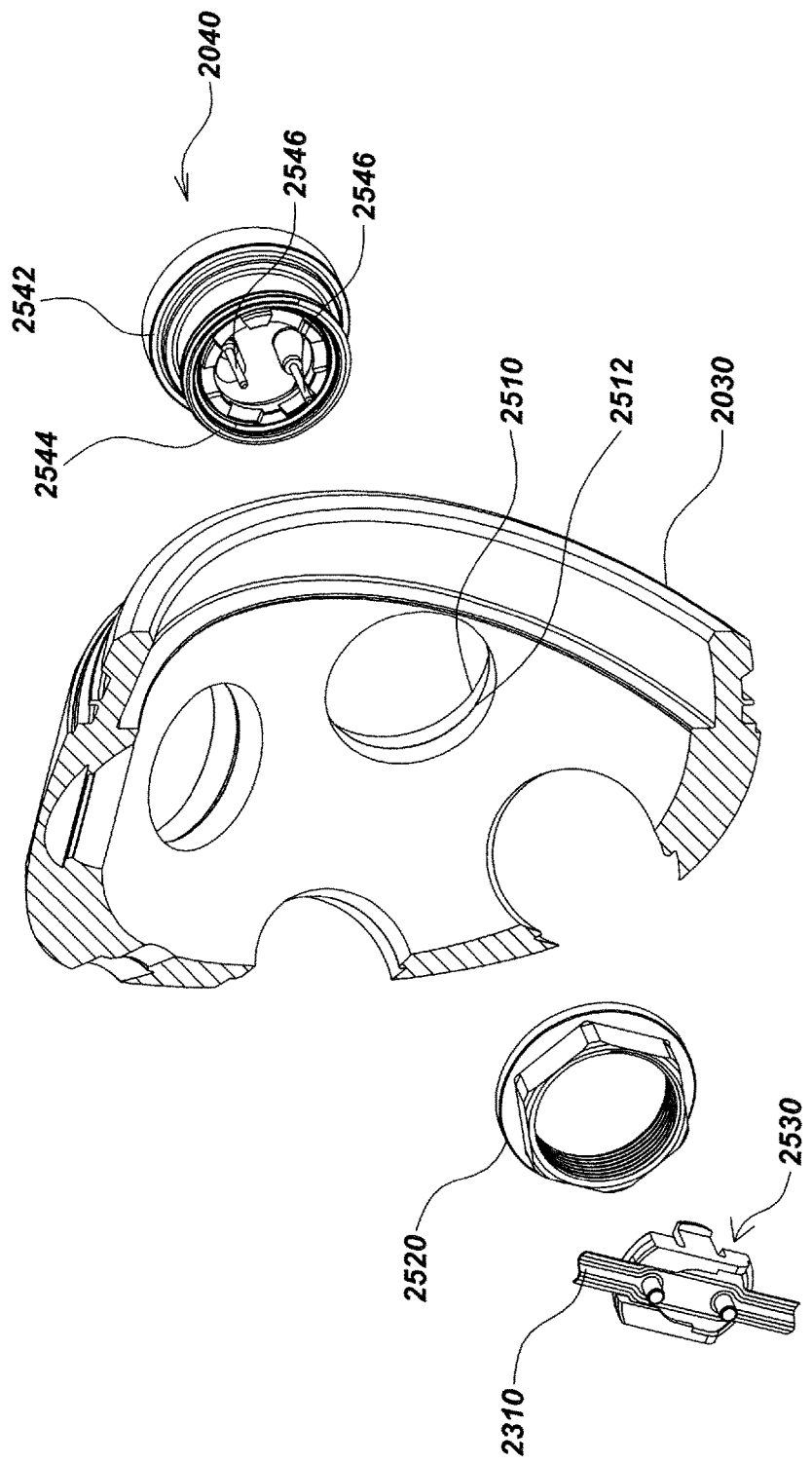
FIG. 25 is a partially exploded view of an embodiment of an illumination module, front camera half housing, nut, and illumination module connecting shoe.

Turning to FIG. 25, each illumination module 2040 may seat within an illumination module holes or opening 2510 formed through the dome 2030 (partially illustrated in FIG. 25). Each illumination module opening 2510 may include a ledge feature 2512, with a slightly reduced diameter toward the outward of the opening, formed on the interior of the dome 2030. In assembly, the illumination module opening 2510 may be dimensioned to permit an inward oriented portion of the illumination module 2040 to fit through, while a lip 2542 formed along the outermost circumference of the illumination module 2040 is prevented from passing through the opening due to the reduced diameter of ledge feature 2512. In some embodiments, an O-ring (not illustrated) or other gasket or seal (not illustrated) may be positioned along ledge feature 2512 and/or otherwise between each illumination module 2040 and front camera half housing 2030 to seal the opening and prevent ingress of potentially harmful materials through the dome into the camera head. Once seated, from within the dome 2030 a nut 2520 may mate with a threaded feature 2544 formed along the inward oriented portion of the illumination module 2040 such that the illumination module 2040 is held securely in place within its illumination module opening 2510 on the dome 2030. In assembly, each of the illumination modules 2040 may be seated such that they do not protrude beyond the outer surface of the front camera half housing 2030.

Still referring to FIG. 25, for each illumination module 2040, an illumination module connecting shoe 2530 may be positioned along the connecting wires 2310 where the connecting wires 2310 make an electrical connection. The illumination module connecting shoe 2530 may snap into place on the back of illumination module 2040 seating pin connectors 2546 on illumination module 2040 with the illumination module connecting shoe 2530. In use, signals and/or electrical power may be provided to each illumination module 2040 via pin connectors 2546 connected when seated within illumination module connecting shoe 2530 and further connected to connecting wires 2310.

Turning to FIGS. 26A and 26B, the illumination modules 2040 may be the same as or similar in various aspects to the illumination module embodiments and corresponding methods as previously described with respect to FIGS. 1-19B. For example, illumination module 2040 may include a largely cylindrical illumination module housing 2610 formed to allow a transparent window 2620 to seat within one end to allow light to pass out of. Illumination module housing 2610 may include an adhesive access hole 2612 through which adhesive may be injected to mount window 2620 using the method 500 illustrated in FIGS. 5 and 6. The window 2620 may comprise sapphire or other transparent material(s). In an exemplary embodiment, the window is made from a material or materials having a high refractive index value and high thermal conductivity so as to maximize light output as well as heat dispersion.

Figure 27:
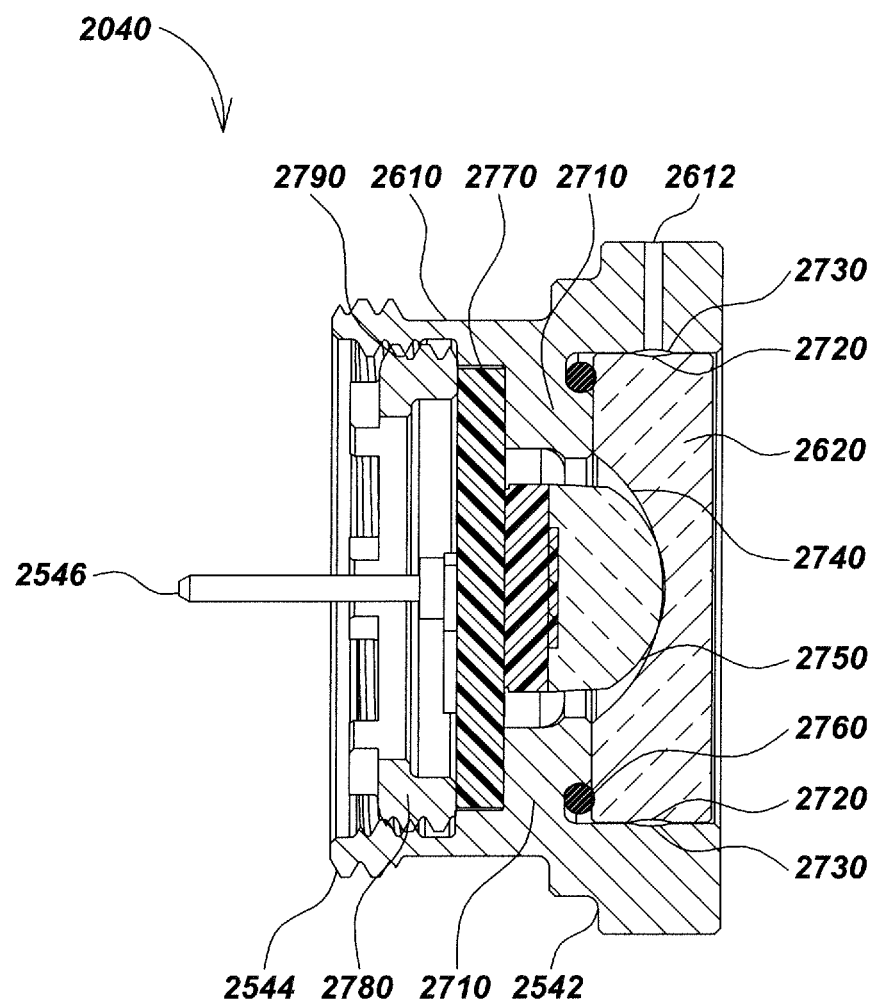
FIG. 27 is a sectional view of the illumination module embodiment of FIG. 26B along line 27-27.
Figure 28:
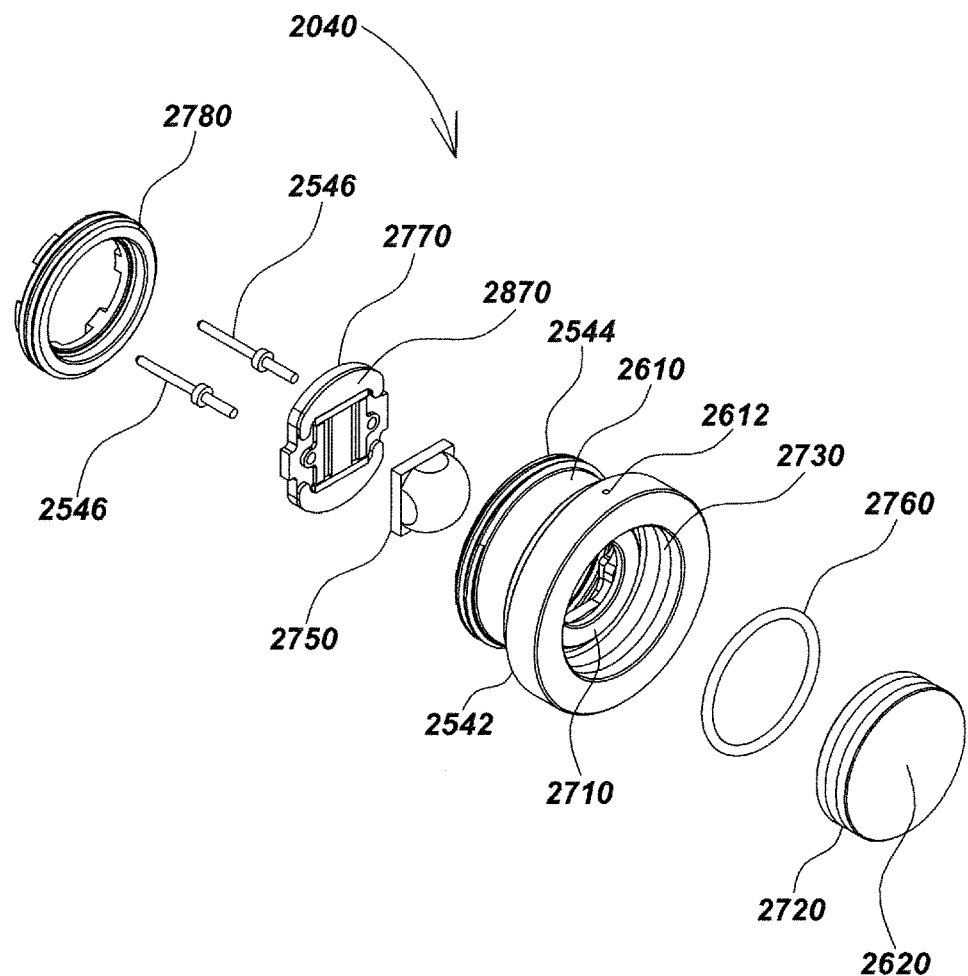
FIG. 28 is an exploded isometric view of the illumination module embodiment of FIG. 25.

Turning to FIGS. 27 and 28, the illumination module housing 2610 may be formed with a shelf feature 2710 onto which window 2620 may be seated in assembly. When seated, a window annular groove feature 2720 may align with a housing annular groove feature 2730, allowing adhesive to flow through and fill the cavity formed by the aligning of window annular groove feature 2720 and housing annular groove feature 2730 (e.g., during assembly via method 500 as illustrated in FIGS. 5 and 6).

On the internally oriented side or face of window 2620, a cavity, which may be a substantially hemispherical cavity feature 2740 as shown in FIG. 27 or another shape matching a corresponding illumination element/light source such as an LED, may be centrally formed. This allows an illumination element such as LED 2750 to press tightly against the surface of the window 2620 within the hemispherical cavity feature 2740 to increase surface contact for light transmission and heat dissipation. The LED 2750 may, for example, be an XLamp® XP-L LED available from Cree or another comparable light source. An O-ring 2760 may be positioned between window 2620 and shelf feature 2710 formed within the illumination module housing 2610 to provide a secondary seal to that provided by the injection of adhesive (e.g., through method 500 of FIGS. 5 and 6 or a similar method).

The LED 2750 may be electrically connected to an illumination module PCB 2770 onto which pin connectors 2546 may also be connected, thereby providing electrical power and/or signals between PCB 2770, attached components and sensors, and LED 2750. PCB 2770 may further include a thermal flood substrate 2870 positioned beneath and thermally coupled to LED 2750 to disperse heat. The thermal flood substrate 2870 (as shown in FIG. 28) may comprise copper and/or other high thermally conductive materials. The thermal flood substrate 2870 may further be thermally coupled to the illumination module housing 2610, allowing heat to be drawn away from LED 2750, PCB 2770 and/or other heat sensitive components such as sensors or other devices. In assembly, a threaded PCB retaining ring 2780 may be screwed onto threads 2790 (as shown in FIG. 27) formed within the back of the illumination module housing 2610 so as to secure PCB 2770 in place.

Figure 29:
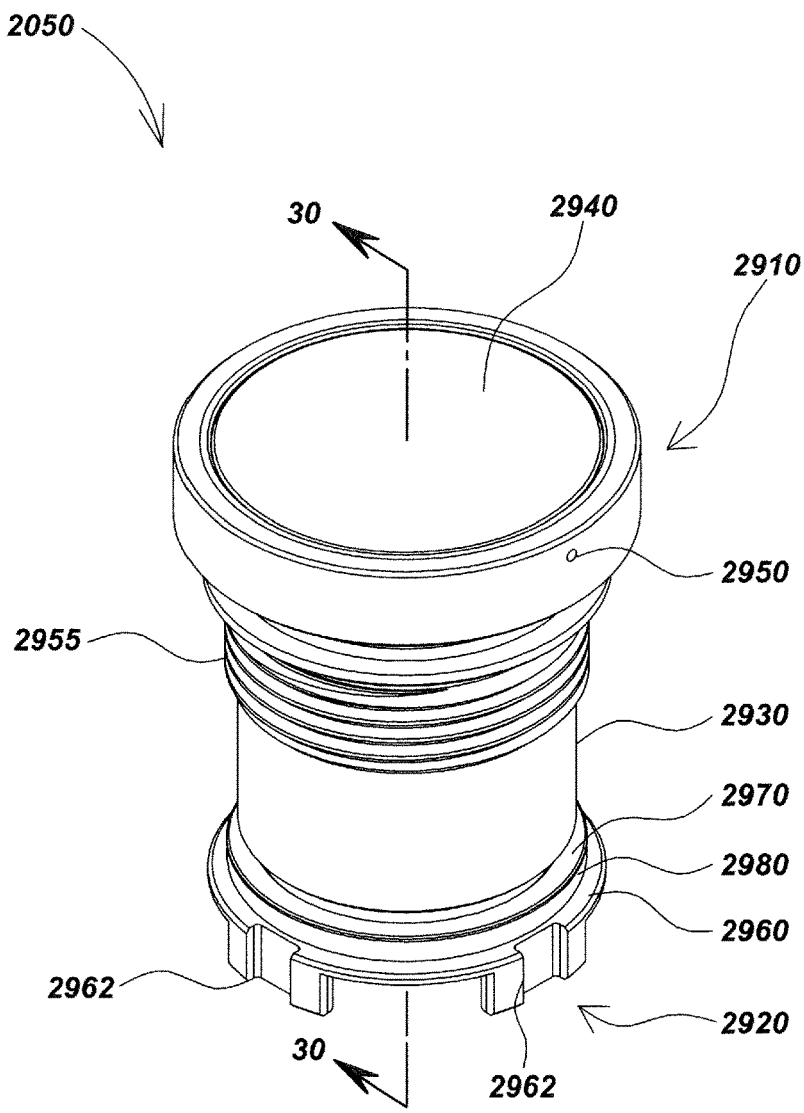
FIG. 29 is an isometric view of certain details of the imaging module embodiment of FIG. 20.

Turning to FIG. 29, details of the exterior of imaging module embodiment 2050 are illustrated. In an exemplary embodiment, the imaging module outer structure may be largely cylindrical in shape and may comprise a front imaging module assembly 2910 and a lens module assembly 2920. The front imaging module assembly 2910 may include a cylindrical front assembly housing 2930 into which a window 2940 may be secured within an outward facing end. In some embodiments lenses on the imaging modules may be contained within the front imaging module assembly 2910 (e.g. with a sapphire or other window assembly) rather than on the imaging module itself. An adhesive access hole feature 2950 may be formed centrally through the side of the front assembly housing 2930 where the window 2940 seats within front imaging module assembly 2910 to facilitate mounting of the window as describe previously herein. Window 2940 may comprise sapphire and/or other transparent materials allowing passage of external light to the optics and imaging sensor. In some embodiment the window 2940 may be coupled to or integrate optical filters such as polarizers, color filters, or other optical filters. The front assembly housing 2930 may be formed with a threaded feature 2955 along its external circumference below where window 2940 is seated to allow the imaging module 2050 to couple to structural element of the camera head.

Figure 31:
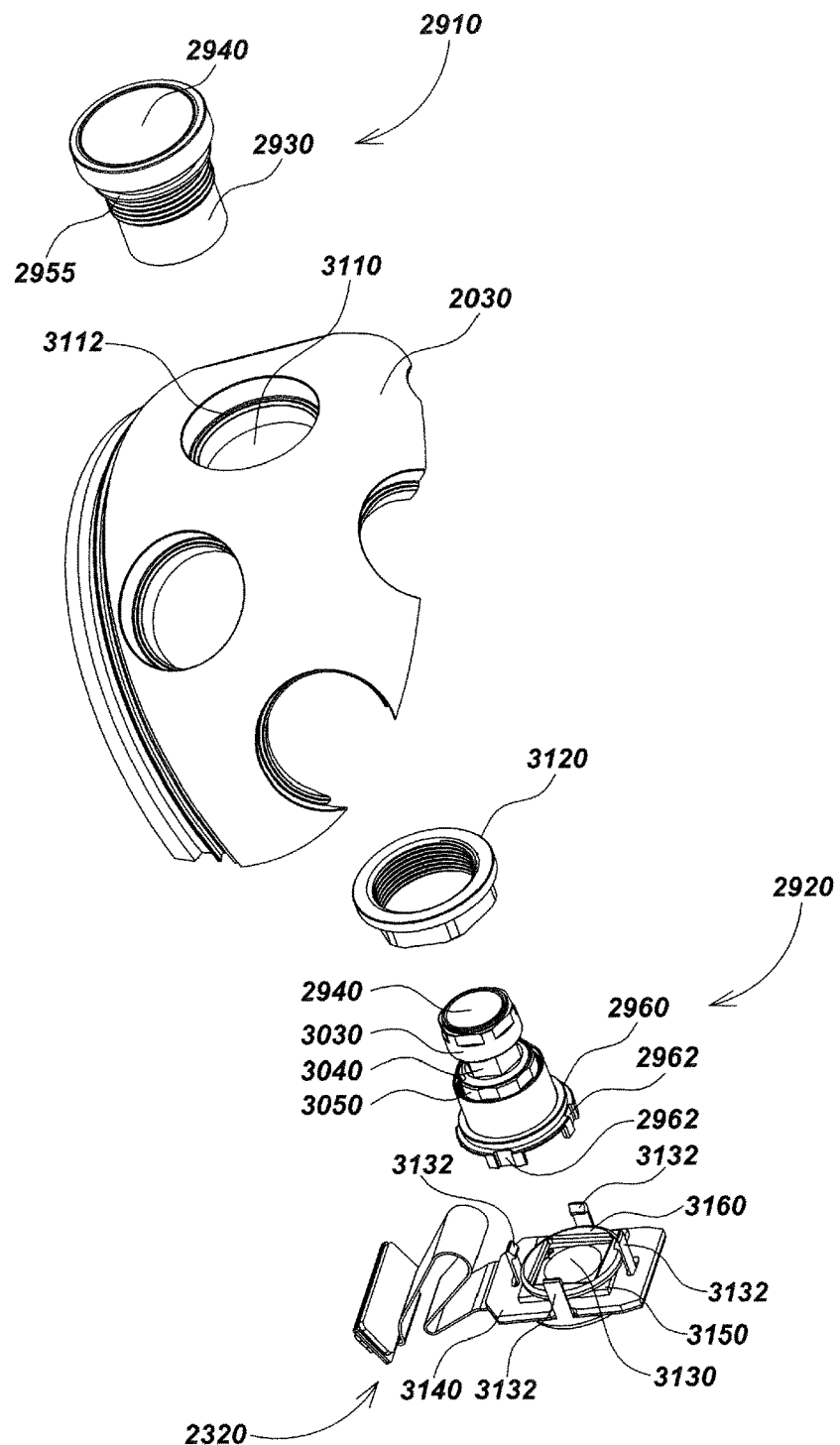
FIG. 31 is a partially exploded view of details of an embodiment of an illumination module, front camera half housing, nut and imaging module connecting shoe.

As illustrated in FIG. 31, the front imaging module assembly 2910 may seat within an imaging module opening 3110 formed through the dome 2030 (dome 2030, which has multiple openings 3110, is partially illustrated in FIG. 31 in cutaway fashion). Each imaging module opening 3110 may include a ledge feature 3112 with slightly reduced internal diameter compared to the outward facing portion of the imaging module opening 3110 and the diameter of the top portion of front assembly housing 2930 where window 2940 is seated. In assembly, the imaging module opening 3110 may be dimensioned to permit an inward oriented portion of the front assembly housing 2930 containing the threaded feature 2955 to fit through, while the top portion of front assembly housing 2930 may seat on top of ledge feature 3112 and within the outward portion of imaging module opening 3110. In some embodiments, an O-ring (not illustrated) or other gasket or sealing element (not illustrated) may be situated along ledge feature 3112 and/or otherwise between each front assembly housing 2930 and dome 2030. Once seated, a nut 3120 may mate with from within the dome 2030 to a threaded feature 2955 formed on the front assembly housing 2930 such that the front assembly housing 2930 is held securely in place within its imaging module opening 3110 on the dome 2030. In assembly, each of the front assembly housings 2930 of the imaging modules may be seated in the dome so that they do not protrude beyond the outer surface of the front camera half housing 2030.

Returning to FIG. 29, the lens module assembly 2920 of an exemplary embodiment may also be largely cylindrical in shape and dimensioned such that an outward oriented portion of the lens module assembly 2920 fits within the front assembly housing 2930 of the front imaging module assembly 2910. Lens module assembly 2920 may include a shoe retainer piece 2960 with a series of shoe arm retaining features 2962. A retaining ring 2970 may seat above the shoe retainer piece 2960 with an O-ring 2980 positioned in between.

As illustrated in FIG. 31, a series of arm features 3132 formed on imaging module connector shoe 3130 may be seated within shoe arm retaining features 2962 on shoe retainer piece 2960 to hold the imaging module connector shoe 3130 properly in place in assembly. The arm features 3132 may further clip into the top of retaining ring 2970 (as shown in FIG. 29) and, in some embodiments, key thereto (not illustrated). On a rigid flex circuit end portion 3140 above the imaging module connector shoe 3130, an imaging sensor 3150 may be connected. In an exemplary embodiment the imaging sensor 3150 may be a dual pixel high dynamic range imaging sensor such as an OV10640 made by Omnivision or another comparable imaging sensor. In various embodiments herein, exposure, gain and color-balance and/or other imaging parameters may be synchronized at each imaging sensor via interconnecting each imaging sensor and/or simultaneously controlled at a processing element such as an FPGA or other processor or programmable computing device.

A gasket 3160 may seat atop the imaging sensor 3150 to protect the imaging sensor 3150 from dust and/or other harmful external materials. In assembly, the O-ring 2980 (as shown in FIG. 29) may be compressed when arm features 3132 are clipped into place onto the top of retaining ring 2970, thus allowing imaging module connector shoe 3130 and imaging sensor 3150 to seat securely about the back of lens module assembly 2920. Manufacturing tolerances of flex circuit end portion 3140 may result in slight differences in thickness of the circuit board material. These slight differences in thickness may be compensated for by the compression of O-ring 2980.

Figure 30:
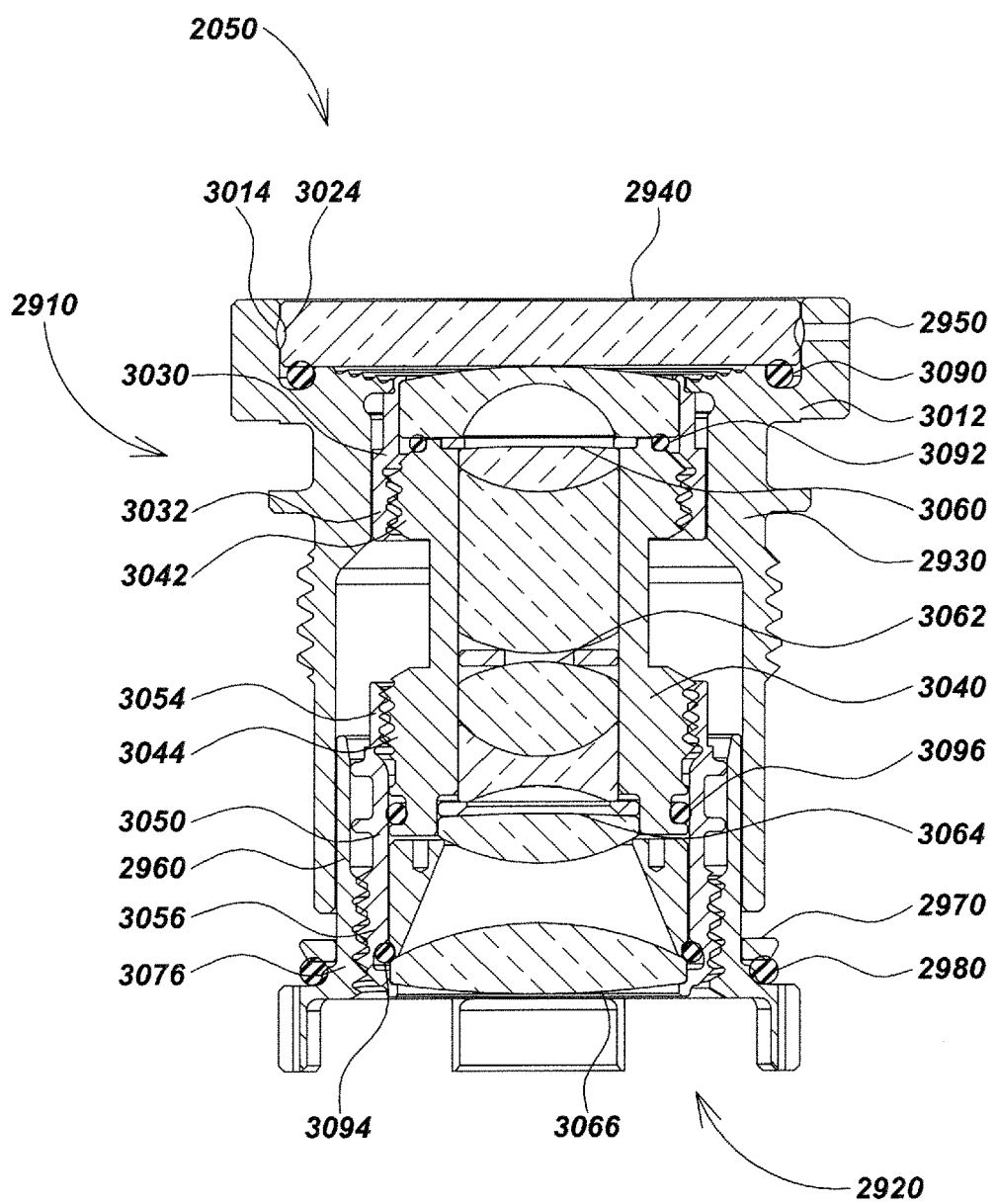
FIG. 30 is a sectional view of the imaging module embodiment of FIG. 29 along line 30-30.

As illustrated in FIG. 30, the window 2940 may be secured in place via method 500 as illustrated in FIGS. 5 and 6 and described previously herein. For example, the front assembly housing 2930 of front imaging module assembly 2910 may be formed with a shelf feature 3012 onto which window 2940 is seated during assembly. When seated, a window annular groove feature 3024 may align with a housing annular groove feature 3014 formed within the front assembly housing 2930 where window 2940 is seated. Alignment of window annular groove feature 3024 and housing annular groove feature 3014 may allow provided adhesive (not illustrated) to flow through adhesive access port feature 2950 through the front assembly housing 2930 to fill the cavity formed by the alignment of window annular groove feature 3024 and housing annular groove feature 3014 during assembly.

Still referring to FIG. 30, lens module assembly 2920 may include a front lens module housing piece 3030, a middle lens module housing piece 3040, and a rear lens module housing piece 3050 within which a series of lenses 3060, 3062, 3064 and 3066 may be secured. In some imaging module embodiments, one or more of the lenses, such as lenses 3060-3066, may be wide angle lenses. In assembly, threaded feature 3032 formed within a bottom portion of front lens module housing piece 3030 may be mated with threaded feature 3042 formed along a top portion of middle lens module housing piece 3040, and threaded feature 3044 formed along a bottom portion of middle lens module housing piece 3040 may be mated with threaded feature 3054 formed within a top portion of the rear lens module housing piece 3050, thereby securing front lens module housing piece 3030, middle lens module housing piece 3040 and rear lens module housing piece 3050 together with lenses 3060, 3062, 3064 and 3066 secured within. Additional external threaded feature 3056 formed about the rear lens module housing piece 3050 may allow the shoe retainer piece 2960 to secure to the rear lens module housing piece 3050 via mating to internal threaded feature 3076 formed within the shoe retainer piece 2960.

Still referring to FIG. 30, a series of additional O-rings and/or other gaskets or sealing elements may be positioned within and about imaging module 2050 to aid in protecting the imaging module 2050 from potentially harmful external materials. For example, an O-ring 3090 may be positioned on shelf feature 3012 of the front assembly housing 2930 between the front assembly housing 2930 and window 2940. An O-ring 3092 may seat between the foremost lens 3060 and front lens module housing piece 3030. Similarly, an O-ring 3094 may seat above the bottommost lens 3066 and rear lens module housing piece 3050. An additional O-ring 3096 may be positioned between the middle lens module housing piece 3040 and rear lens module housing piece 3050 behind where middle lens module housing piece 3040 and rear lens module housing piece 3050 secure together via threaded features 3044 and 3054. Other O-rings and/or other gaskets or sealing elements may further be used in some embodiments in various locations throughout and about imaging module 2050.

In one or more exemplary embodiments, certain functions, methods and processes described herein related to control of and/or data communication to or from imaging modules, illumination modules, processing elements, and/or other electronic elements of camera heads and associated inspection systems may be implemented in hardware, software, firmware or any combination thereof. If implemented in software, the functions may be stored on or encoded as one or more instructions or code on a non-transitory computer-readable medium. Computer-readable media includes computer storage media. Storage media may be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

It is understood that the specific order or hierarchy of steps or stages in the processes and methods disclosed herein are examples of exemplary approaches. Based upon design preferences, it is understood that the specific order or hierarchy of steps or stages in the processes may be rearranged while remaining within the scope of the present disclosure. Any accompanying method claims present elements of the various steps in a sample order, and are not meant to be limited to the specific order or hierarchy presented unless explicitly noted.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles or any combination thereof.

Those of skill would further appreciate that the various illustrative logical blocks, modules, circuits and algorithm steps described in connection with the embodiments disclosed herein may be implemented as electronic hardware, computer software or combinations of both. To clearly illustrate this interchangeability of hardware and software, various illustrative components, blocks, modules, circuits and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the disclosure.

The various illustrative logical blocks, modules, and circuits described in connection with the embodiments disclosed herein and, for example, in processing elements as described herein may be implemented or performed with a general purpose processor, a digital signal processor (DSP), an application specific integrated circuit (ASIC), a field programmable gate array (FPGA) or other programmable logic device, discrete gate or transistor logic, discrete hardware components or any combination thereof designed to perform the functions described herein. A general purpose processor may be a microprocessor, but in the alternative, the processor may be any conventional processor, controller, microcontroller or state machine. A processor may also be implemented as a combination of computing devices, e.g., a combination of a DSP and a microprocessor, a plurality of microprocessors, one or more microprocessors in conjunction with a DSP core or any other such configuration. A processing element may furthering include or be coupled to one or more memory elements for storing instructions, data and/or other information in a non-transitory digital storage format.

The steps or stages of a method, process or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, CD-ROMs or any other form of storage medium known or developed in the art. An exemplary storage medium is coupled to the processor such that the processor can read information from, and write information to the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The scope of the disclosure is not intended to be limited to the aspects shown herein, but is to be accorded the full scope consistent with the language of this specification and accompanying drawings, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c.

The previous description of the disclosed aspects is provided to enable any person skilled in the art to make or use embodiments of the present invention. Various modifications to these aspects will be readily apparent to those skilled in the art, and the generic principles defined herein may be applied to other aspects without departing from the spirit or scope of the invention. Thus, the scope of the invention is not intended to be limited to the aspects shown herein but is to be accorded the widest scope consistent with the appended claims and their equivalents.

We claim:

1. A camera head, comprising:
   a housing, including:
   a front housing element including a section having a rounded, half-spherical shaped section; and;
   a rear housing element coupled to the front housing element, the rear housing element including a substantially cylindrical longitudinal section;
   a plurality of imaging modules disposed on or within the front element about the rounded section so as to capture images from circularly offset angles relative to each other; and
   a plurality of illumination modules disposed on or within the front element between ones of the imaging modules so as the plurality of imaging modules including a first set of one or more imaging modules and a second set of one or more imaging modules;
   wherein the illumination modules are selectively controlled in conjunction with an imaging operation of one or more of the imaging modules, where the operation includes adjusting the level of the light output from the first set of illumination modules so that the light output level from the first set of illumination modules is higher during a first imaging time interval than during non-imaging time intervals and the level of the light output from the second set of illumination modules is maintained at a low output level during the first time interval, and adjusting the light output of the second set of illumination modules so that the light output of the second set of illumination modules is higher during a second imaging time interval, different from the first imaging time interval while the level of the light output from the first set of illumination modules is maintained at a low output level during the second time interval; and
   wherein a plurality of images captured by one or more of the imaging modules at different light output levels are combined to generate a high dynamic range (HDR) image or video.

2. The camera head of claim 1, wherein the front housing element includes ones of a plurality of imaging module openings disposed around the rounded shape section, and wherein ones of the plurality of imaging modules are disposed on or within corresponding ones of the plurality of imaging module openings.

3. The camera head of claim 2, wherein the front housing element further includes ones of a plurality of illumination module openings disposed between ones of the plurality of imaging module openings, and wherein ones of the plurality of illumination modules are disposed on or within corresponding ones of the plurality of illumination module openings.

4. The camera head of claim 1, wherein the illumination modules include:
   a light output window having an inner side and an outer side; and
   a light emitting diode (LED) illumination element positioned in proximity to the inner side.

5. The camera head of claim 4, wherein a cavity is formed on the inner side and wherein the LED is positioned at least partially within the cavity and against the light output window.

6. The camera head of claim 4, wherein the illumination module includes a housing having an annular groove, an adhesive access feature, a window, and an injected adhesive between the window and housing to secure the window to the housing.

7. The camera head of claim 1, wherein the illumination modules include:
   a light output window having an inner side and an outer side; and
   a laser illumination element positioned in proximity to the inner side.

8. The camera head of claim 1, wherein the plurality of imaging modules consists of six imaging modules, wherein a first imaging module is disposed at the front of the housing and the other five imaging modules are arranged on a circumference on the housing behind the first imaging module.

9. The camera head of claim 1, wherein the plurality of illumination modules comprises ten illumination modules distributed along a first and a second circumference of the housing behind the first imaging module.

10. The camera head of claim 1, wherein each of the imaging modules include one or more imaging sensors, optics, and a transparent window.

11. The camera head of claim 10, wherein the imaging modules include a housing having an annular groove, an adhesive access feature, and an injected adhesive between the transparent window and housing to secure the transparent window to the housing.

12. The camera head of claim 10, wherein the field of view of ones of the plurality of imaging modules is about 160 degrees.

13. The camera head of claim 10, wherein each of the imaging modules have a central optical axis that shares a common point or centroid in the camera head.

14. The camera head of claim 10, wherein the field of view covered by the optics is projected entirely on an active imaging area of the imaging sensor.

15. The camera head of claim 10, wherein the field of view covered by the optics is projected in part outside the active imaging area of the imaging sensor so that the projected FOV circumscribes the active imaging area of the imaging sensor.

16. The camera head of claim 1, further comprising a processing element programmed to generate composite image or video output data from ones of outputs of the plurality of imaging modules.

17. The camera head of claim 16, wherein the processing element digitally stitches or tiles imaging from the plurality of imaging modules to generate the composite image or video output.

18. The camera head of claim 16, wherein ones of the plurality of imaging modules are synchronously controlled to generate the output image or video.

19. The camera head of claim 18, wherein the ones of the plurality of imaging modules are synchronously controlled to have one or more of the same: ISO settings, gain settings, exposure settings, color balance settings, aperture settings, shutter timing, and exposure timing.

20. The camera head of claim 16, wherein the light output of one or more of the illumination modules are selectively set to a maximum value during the imaging operations and selectively set to a lower value during the other time interval.

21. The camera head of claim 16, further comprising one or more position, motion, or orientation sensors having outputs communicatively coupled to the processing element, and wherein output data from the one or more position, motion, or orientation sensors is associated and stored with the composite image or video output data in a memory of the camera head.

22. The camera head of claim 16, further comprising a wireless communications module communicatively coupled to the processing element for transmitting the composite image or video data to an electronic computing system.

23. The camera head of claim 1, wherein the illumination modules are LEDs and the light output of the LEDs is selectively controlled by raising the voltage applied to the LEDs.

24. The camera head of claim 23, wherein the light output of the LEDs is periodically raised to a maximum level for at a duty cycle of about ten percent or less.

25. The camera head of claim 1, wherein ones of the plurality of illumination modules are selectively controlled in synchronization.

26. The camera head of claim 1, wherein ones of the plurality of illumination modules are selectively controlled to generate a maximum light output at different time intervals.

27. The camera head of claim 1, wherein each of the illumination modules include a housing and a thermally conductive circuit element positioned in a thermal contact with the housing.

28. The camera head of claim 1, further comprising a sonde integral with or coupled to the camera head housing.

29. The camera head of claim 1, further comprising a mast coupled to the camera head.

\* \* \* \* \*